United States Patent
Miyake et al.

(10) Patent No.: US 11,805,697 B2
(45) Date of Patent: Oct. 31, 2023

(54) ORGANIC ELECTROLUMINESCENCE DEVICE AND MONOAMINE COMPOUND FOR ORGANIC ELECTROLUMINESCENCE DEVICE

(71) Applicant: Samsung Display Co., Ltd., Yongin-si (KR)

(72) Inventors: Hideo Miyake, Yokohama (JP); Masatsugu Ueno, Yokohama (JP); Xiulan Jin, Yokohama (JP); Ichinori Takada, Yokohama (JP); Takuya Uno, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 17/947,056

(22) Filed: Sep. 16, 2022

(65) Prior Publication Data

US 2023/0055036 A1 Feb. 23, 2023

Related U.S. Application Data

(63) Continuation of application No. 16/254,777, filed on Jan. 23, 2019.

(30) Foreign Application Priority Data

Jan. 26, 2018 (KR) .......... 10-2018-0009993
Nov. 20, 2018 (KR) .......... 10-2018-0143745

(51) Int. Cl.
*H01L 51/00* (2006.01)
*C07D 333/76* (2006.01)
(Continued)

(52) U.S. Cl.
CPC .......... *H10K 85/636* (2023.02); *C07C 211/54* (2013.01); *C07C 211/61* (2013.01);
(Continued)

(58) Field of Classification Search
None
See application file for complete search history.

(56) References Cited

U.S. PATENT DOCUMENTS 4,720,432 A 1/1988 VanSlyke et al.
5,061,569 A 10/1991 VanSlyke et al.
(Continued)

FOREIGN PATENT DOCUMENTS

CN 102596907 B 12/2014
CN 106008424 A 10/2016
(Continued)

OTHER PUBLICATIONS

Hwang, Seok-Hwan, et al. "Improved performance of organic light-emitting diodes using advanced hole-transporting materials." Synthetic metals 159.23-24 (2009): 2578-2583. (Year: 2009).
(Continued)

*Primary Examiner* — Jay Yang
(74) *Attorney, Agent, or Firm* — Lewis Roca Rothgerber Christie LLP

(57) ABSTRACT

An organic electroluminescence device includes a first electrode, a hole transport region on the first electrode, an emission layer on the hole transport region, an electron transport region on the emission layer, and a second electrode on the electron transport region. The hole transport region includes a monoamine compound represented by the following Formula 1:

(Continued)

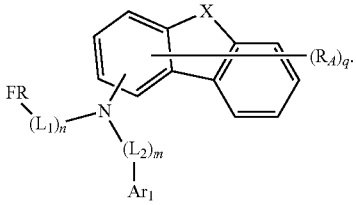

[Formula 1]

17 Claims, 2 Drawing Sheets

(51) Int. Cl.
C07C 211/61 (2006.01)
C07D 409/12 (2006.01)
C07D 307/91 (2006.01)
C09K 11/06 (2006.01)
C07D 311/96 (2006.01)
C07C 211/54 (2006.01)
C07D 407/12 (2006.01)
H10K 85/60 (2023.01)
H10K 50/11 (2023.01)
H10K 50/15 (2023.01)
H10K 50/16 (2023.01)
H10K 50/17 (2023.01)
H10K 50/18 (2023.01)

(52) U.S. Cl.
CPC .......... C07D 307/91 (2013.01); C07D 311/96 (2013.01); C07D 333/76 (2013.01); C07D 407/12 (2013.01); C07D 409/12 (2013.01); C09K 11/06 (2013.01); H10K 85/633 (2023.02); H10K 85/6572 (2023.02); H10K 85/6574 (2023.02); H10K 85/6576 (2023.02); C07C 2603/18 (2017.05); C07C 2603/97 (2017.05); C09K 2211/1007 (2013.01); C09K 2211/1011 (2013.01); C09K 2211/1014 (2013.01); C09K 2211/1018 (2013.01); H10K 50/11 (2023.02); H10K 50/15 (2023.02); H10K 50/16 (2023.02); H10K 50/17 (2023.02); H10K 50/171 (2023.02); H10K 50/18 (2023.02); H10K 85/615 (2023.02); H10K 85/624 (2023.02); H10K 85/626 (2023.02)

(56) References Cited

U.S. PATENT DOCUMENTS

| | | | |
|---|---|---|---|
| 6,242,115 B1 | 6/2001 | Thomson et al. |
| 7,507,485 B2 | 3/2009 | Oh et al. |
| 8,129,038 B2 | 3/2012 | Yabunouchi et al. |
| 8,889,268 B2 | 11/2014 | Takada et al. |
| 9,139,522 B2 | 9/2015 | Yabunouchi et al. |
| 9,278,926 B2 | 3/2016 | Kato |
| 9,525,141 B2 | 12/2016 | Kim et al. |
| 9,590,186 B2 | 3/2017 | Itoi et al. |
| 9,842,995 B2 | 12/2017 | Jung et al. |
| 9,972,787 B2 | 5/2018 | Miyake et al. |
| 10,211,406 B2 | 2/2019 | Hwang et al. |
| 10,333,075 B2 | 6/2019 | Miyake et al. |
| 10,923,663 B2 | 2/2021 | Takada et al. |
| 10,941,108 B2 | 3/2021 | Jeong et al. |
| 11,196,008 B2 | 12/2021 | Park et al. |
| 2002/0094452 A1 | 7/2002 | Ueda et al. |
| 2008/0241591 A1 | 10/2008 | Kawamura et al. |
| 2009/0230852 A1 | 9/2009 | Lee et al. |
| 2011/0031877 A1 | 2/2011 | Takada et al. |
| 2012/0199820 A1 | 8/2012 | Ito et al. |
| 2014/0367649 A1 | 12/2014 | Cho et al. |
| 2014/0374711 A1 | 12/2014 | Cho et al. |
| 2015/0179940 A1 | 6/2015 | Mujica-Fernaud et al. |
| 2015/0243891 A1 | 8/2015 | Kato et al. |
| 2016/0093810 A1 | 3/2016 | Miyake |
| 2016/0163982 A1 | 6/2016 | Ishihara et al. |
| 2016/0293843 A1 | 10/2016 | Itoi |
| 2016/0365517 A1 | 12/2016 | Mun et al. |
| 2016/0372665 A1 | 12/2016 | Takada |
| 2016/0372666 A1 | 12/2016 | Ryu et al. |
| 2016/0372677 A1 | 12/2016 | Miyake |
| 2017/0125677 A1 | 5/2017 | Kim et al. |
| 2017/0125689 A1 | 5/2017 | Lee et al. |
| 2018/0083197 A1 | 3/2018 | Park et al. |
| 2018/0182961 A1 | 6/2018 | Kawakami et al. |
| 2018/0226585 A1 | 8/2018 | Park et al. |
| 2018/0269401 A1 | 9/2018 | Cha et al. |
| 2018/0331290 A1 | 11/2018 | Miyake et al. |
| 2019/0039996 A1 | 2/2019 | Takada et al. |
| 2019/0055187 A1 | 2/2019 | Kim et al. |
| 2019/0140177 A1 | 5/2019 | Lee et al. |
| 2019/0237668 A1 | 8/2019 | Miyake et al. |

FOREIGN PATENT DOCUMENTS

| | | |
|---|---|---|
| CN | 106831313 A | 6/2017 |
| CN | 106083606 B | 6/2018 |
| CN | 109749735 A | 5/2019 |
| CN | 111315717 A | 6/2020 |
| JP | 5-303221 A | 11/1993 |
| JP | 6-314594 A | 11/1994 |
| JP | 8-291115 A | 11/1996 |
| JP | 11-144873 A | 5/1999 |
| JP | 2000-302756 A | 10/2000 |
| JP | 2000-309566 A | 11/2000 |
| JP | 2003-201472 A | 7/2003 |
| JP | 2006-151979 A | 6/2006 |
| JP | 2009-029726 A | 2/2009 |
| JP | 2009-267255 A | 11/2009 |
| JP | 2009-283899 A | 12/2009 |
| JP | 2010-186983 A | 8/2010 |
| JP | 5739815 B2 | 6/2015 |
| JP | 2016-66723 A | 4/2016 |
| JP | 5919427 B2 | 5/2016 |
| JP | 6085354 B2 | 2/2017 |
| JP | 2018-65806 A | 4/2018 |
| KR | 10-2013-0101726 A | 9/2013 |
| KR | 10-1373587 B1 | 3/2014 |
| KR | 10-2014-0043224 A | 4/2014 |
| KR | 10-2015-0006374 A | 1/2015 |
| KR | 10-2015-0024735 A | 3/2015 |
| KR | 10-1530266 B1 | 12/2015 |
| KR | 10-1580074 B1 | 12/2015 |
| KR | 10-2016-0054855 A | 5/2016 |
| KR | 10-2016-0054866 A | 5/2016 |
| KR | 10-2016-0059609 A | 5/2016 |
| KR | 10-2016-0061571 A | 6/2016 |
| KR | 10-1638072 B1 | 7/2016 |
| KR | 10-1639867 B1 | 7/2016 |
| KR | 10-2016-0113783 A | 10/2016 |
| KR | 10-2016-0120609 A | 10/2016 |
| KR | 10-2016-0132344 A | 11/2016 |
| KR | 10-2016-0149977 A | 12/2016 |
| KR | 10-2016-0149987 A | 12/2016 |
| KR | 10-2017-0011947 A | 2/2017 |
| KR | 10-1730275 B1 | 4/2017 |
| KR | 10-2017-0061727 A | 6/2017 |
| KR | 10-2017-0094708 A | 8/2017 |
| KR | 2017-0094665 A | 8/2017 |
| KR | 2017-0127099 A | 11/2017 |
| KR | 10-2018-0078177 A | 7/2018 |
| KR | 10-1881645 A1 | 7/2018 |
| KR | 10-2018-0124728 | 11/2018 |
| KR | 10-2019-0020275 A | 2/2019 |
| KR | 10-2019-0050525 A | 5/2019 |
| KR | 10-2019-0052505 A | 5/2019 |
| KR | 10-2019-0091410 A | 8/2019 |

(56) References Cited

FOREIGN PATENT DOCUMENTS

| WO | WO 2010/044130 A1 | 4/2010 |
|----|---|---|
| WO | WO 2011/163610 A2 | 12/2011 |
| WO | WO 2012/018120 A1 | 2/2012 |
| WO | WO 2012/091471 A2 | 7/2012 |
| WO | WO 2012/148127 A2 | 11/2012 |
| WO | WO 2013/002514 A2 | 1/2013 |
| WO | WO 2014/034795 A1 | 3/2014 |
| WO | WO 2015/130069 A1 | 9/2015 |
| WO | WO 2015/194791 A2 | 12/2015 |
| WO | WO 2016/178544 A2 | 11/2016 |
| WO | WO 2016/208862 A1 | 12/2016 |
| WO | WO 2017/014357 A1 | 1/2017 |
| WO | WO 2017/100967 A1 | 6/2017 |
| WO | WO 2017/116167 A1 | 7/2017 |
| WO | WO 2007/125714 A1 | 11/2017 |
| WO | WO 2018/038544 A1 | 3/2018 |
| WO | WO 2019/088517 A1 | 5/2019 |

OTHER PUBLICATIONS

U.S. Final Office Action dated Oct. 14, 2022, issued in U.S. Appl. No. 16/256,225 (17 pages).
U.S. Office Action dated Oct. 24, 2022, issued in U.S. Appl. No. 16/590,214 (8 pages).
U.S. Office Action dated Nov. 4, 2022, issued in U.S. Appl. No. 16/254,777 (6 pages).
Chinese Office Action dated Oct. 13, 2022, issued in corresponding Chinese Patent Application No. 201910069905.7 (10 pages).
European Search Report dated May 7, 2019.
Extended European Search Report for corresponding European Patent Application No. 19153603.6, dated May 7, 2019, 9 pages.
Machine English translation of Ham et al. (WO 2016/178544 A1). Feb. 16, 2021.
U.S. Office Action dated Feb. 22, 2021, issued in U.S. Appl. No. 16/254,777 (10 pages).
U.S. Office Action dated Jul. 23, 2021, issued in U.S. Appl. No. 16/254,777 (12 pages).
U.S. Advisory Action dated Oct. 8, 2021, issued in U.S. Appl. No. 16/254,777 (5 pages).
U.S. Office Action dated Oct. 29, 2021, issued in U.S. Appl. No. 16/254,777 (9 pages).
Journal of Materials Chemistry C, (2018), vol. 6, pp. 8280-8325 (Year: 2018).
Journal of Power Sources, vol. 425, (2019), pp. 87-93 (Year: 2019).
Machine translation of JP 2018-065806 A (publication date Apr. 2018). (Year: 2018).
Machine translation of WO 2019/088517 A1 (publication date May 2019). (Year: 2019).
U.S. Office Action dated May 11, 2021, issued in U.S. Appl. No. 16/256,225 (11 pages).
U.S. Office Action dated Nov. 17, 2021, issued in U.S. Appl. No. 16/590,214 (10 pages).
Tong et al., "Transport and Luminescence in Naphthyl Phenylamine Model Compounds," Synthetic Metals, 2004, vol. 147, pp. 199-203.
U.S. Office Action dated Apr. 26, 2022, issued in U.S. Appl. No. 16/256,225 (16 pages).
U.S. Office Action dated Mar. 18, 2022, issued in U.S. Appl. No. 16/590,214 (10 pages).
U.S. Office Action dated Nov. 29, 2021, issued in U.S. Appl. No. 16/256,225 (10 pages).
U.S. Advisory Action dated May 26, 2022, issued in U.S. Appl. No. 16/590,214 (4 pages).
Machine translation of WO 2018/038544, translation generated Jun. 2022, 84 pages. (Year: 2022).
U.S. Office Action dated Jul. 13, 2022, issued in U.S. Appl. No. 16/590,214 (10 pages).
U.S. Office Action dated Jul. 27, 2022, issued in U.S. Appl. No. 16/842,556 (16 pages).
Office Action for U.S. Appl. No. 16/256,225 dated May 4, 2023, 10 pages.
Vijaya Sundar, J., et al. "Excited State C—N Bond Dissociation and Cyclization of Tri-aryl Amine-based OLED Materials: A Theoretical Investigation," Physical Chemistry Chemical Physics, 2019, 21(1), pp. 438-447.
Notice of Allowance for U.S. Appl. No. 16/254,777 dated Apr. 4, 2023, 8 pages.
U.S. Final Office Action dated Feb. 1, 2023, issued in U.S. Appl. No. 16/842,556 (16 pages).
U.S. Notice of Allowance dated Feb. 10, 2023, issued in U.S. Appl. No. 16/590,214 (7 pages).
Chinese Office Action dated Jun. 14, 2023, including Search Report dated Jun. 12, 2023, for corresponding Application No. 201910073655.4, 7 pages.
Notice of Allowance for U.S. Appl. No. 16/256,225 dated Aug. 28, 2023, 8 pages.
Office Action for U.S. Appl. No. 16/842,556 dated Aug. 29, 2023, 23 pages.

ORGANIC ELECTROLUMINESCENCE DEVICE AND MONOAMINE COMPOUND FOR ORGANIC ELECTROLUMINESCENCE DEVICE

CROSS-REFERENCE TO RELATED APPLICATION

This application is a continuation of, and claims priority to and the benefit of U.S. patent application Ser. No. 16/254,777, filed on Jan. 23, 2019, which claims priority to and the benefit of Korean Patent Application No. 10-2018-0009993, filed on Jan. 26, 2018, and Korean Patent Application No. 10-2018-0143745, filed on Nov. 20, 2018, in the Korean Intellectual Property Office, and entitled: "Organic Electroluminescence Device and Monoamine Compound for Organic Electroluminescence Device," the entire contents of all of which are incorporated herein by reference.

BACKGROUND

1. Field

Embodiments relate to an organic electroluminescence device and a monoamine compound for an organic electroluminescence device.

2. Description of the Related Art

Development on an organic electroluminescence display as an image display is being actively conducted. An organic electroluminescence display is different from a liquid crystal display and is so called a self-luminescent display that accomplishes display by recombining holes and electrons injected from a first electrode and a second electrode in an emission layer and emitting light from a luminescent material which includes an organic compound in the emission layer.

SUMMARY

Embodiments are directed to an organic electroluminescence device including a first electrode, a hole transport region on the first electrode, an emission layer on the hole transport region, an electron transport region on the emission layer and a second electrode on the electron transport region, in which the hole transport region includes a monoamine compound represented by the following Formula 1.

[Formula 1]

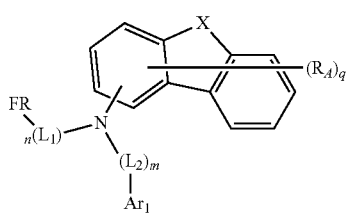

In Formula 1, X is S, O or CRR', R and R' may each independently be a substituted or unsubstituted alkyl group having 1 to 10 carbon atoms, a substituted or unsubstituted aryl group having 6 to 20 ring carbon atoms, or a substituted or unsubstituted heteroaryl group having 2 to 10 ring carbon atoms, and are separate or form a ring by combining adjacent groups with each other, $L_1$ and $L_2$ may each independently be a direct linkage, a substituted or unsubstituted arylene group having 6 to 12 ring carbon atoms, or a substituted or unsubstituted heteroarylene group having 2 to 12 ring carbon atoms, n and m may each independently be an integer of 0 to 2, $R_A$ may be a hydrogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, q may be an integer of 0 to 7, $Ar_1$ may be a substituted or unsubstituted aryl group having 6 to 12 ring carbon atoms, or a substituted or unsubstituted heteroaryl group having 2 to 12 ring carbon atoms, in a case where X is CRR' then $Ar_1$ may not include a heteroaryl group, and FR may be represented by the following Formula 2.

[Formula 2]

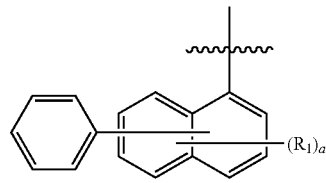

In an embodiment, the hole transport region may have a plurality of layers, and a layer of the plurality of layers contacting with the emission layer may include the monoamine compound according to an example embodiment.

In an embodiment, the hole transport region may include a hole injection layer on the first electrode, a hole transport layer on the hole injection layer, and an electron blocking layer on the hole transport layer, and the electron blocking layer may include the monoamine compound according to an example embodiment.

In an embodiment, the electron transport region may include a hole blocking layer on the emission layer, an electron transport layer on the hole blocking layer, and an electron injection layer on the electron transport layer.

In Formula 2, $R_1$ may be a hydrogen atom, a deuterium atom, or a halogen atom, and a may be an integer of 0 to 6.

In an embodiment, FR may be represented by the following Formula 2-1.

[Formula 2-1]

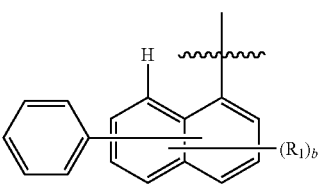

In Formula 2-1, b may be an integer of 0 to and $R_1$ is the same as defined above.

In an embodiment, n may be 1, and $L_1$ may be a substituted or unsubstituted arylene group having 6 to 12 ring carbon atoms.

In an embodiment, $L_1$ may be a substituted or unsubstituted phenylene group.

In an embodiment, FR may be substituted at a para position to the nitrogen atom.

In an embodiment, m may be 1, $L_2$ may be a substituted or unsubstituted arylene group having 6 to 12 ring carbon atoms, and Ar$_1$ may be a substituted or unsubstituted aryl group having 6 to 12 ring carbon atoms.

In an embodiment, L$_2$ may be a substituted or unsubstituted phenylene group, and Ar$_1$ may be a substituted or unsubstituted phenyl group, a substituted or unsubstituted biphenyl group, or a substituted or unsubstituted naphthyl group.

In an embodiment, m may be 0, and Ar$_1$ may be a substituted or unsubstituted heteroaryl group having 5 to 12 ring carbon atoms.

In an embodiment, Ar$_1$ may be a substituted or unsubstituted dibenzofuran group, or a substituted or unsubstituted dibenzothiophene group.

Embodiments are also directed to a monoamine compound represented by the above Formula 1.

BRIEF DESCRIPTION OF THE DRAWINGS

Features will become apparent to those of skill in the art by describing in detail example embodiments with reference to the attached drawings in which.

DETAILED DESCRIPTION

Figure 1:
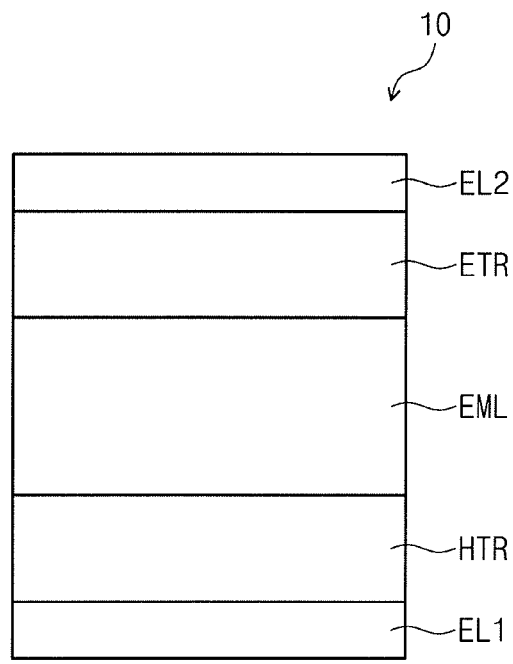
FIG. 1 illustrates a schematic cross-sectional view of an organic electroluminescence device according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprise" or "have," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening layers may also be present. On the other hand, when a layer, a film, a region, a plate, etc. is referred to as being "under" another part, it can be "directly under" the other part, or intervening layers may also be present.

First, an organic electroluminescence device according to an example embodiment will be explained referring to FIGS. 1 to 3.

FIG. 1 is a schematic cross-sectional view illustrating an organic electroluminescence device according to an example embodiment. FIG. 2 is a schematic cross-sectional view illustrating an organic electroluminescence device according to an example embodiment. FIG. 3 is a schematic cross-sectional view illustrating an organic electroluminescence device according to an example embodiment.

Figure 2:
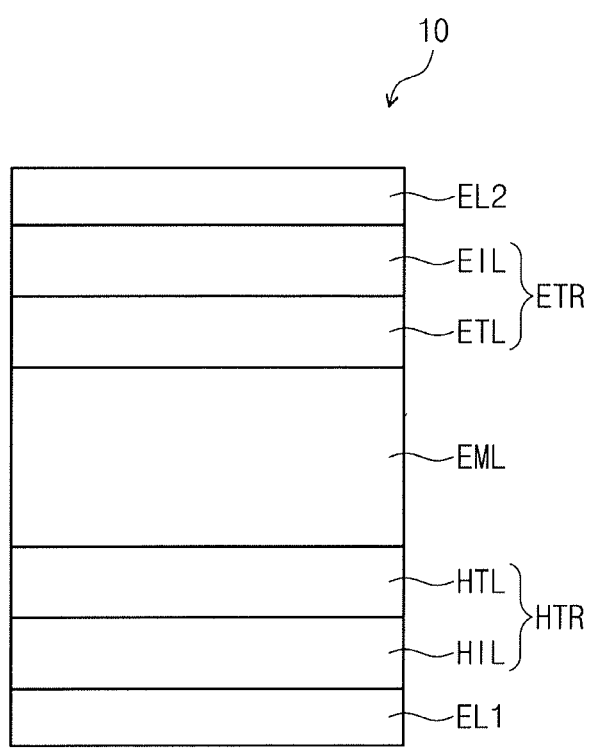
FIG. 2 illustrates a schematic cross-sectional view of an organic electroluminescence device according to an example embodiment.
Figure 3:
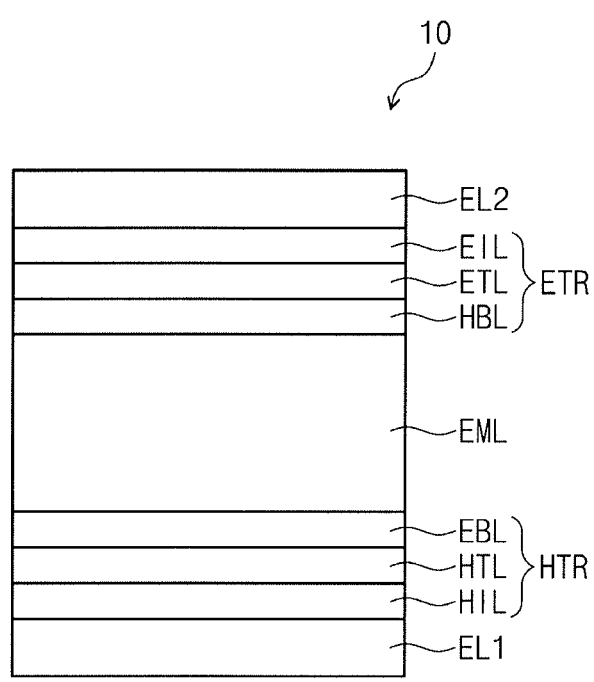
FIG. 3 illustrates a schematic cross-sectional view of an organic electroluminescence device according to an example embodiment.

Referring to FIGS. 1 to 3, an organic electroluminescence device 10 according to an example embodiment includes a first electrode EL1, a hole transport region HTR, an emission layer EML, an electron transport region ETR, and a second electrode EL2.

The hole transport region HTR includes the monoamine compound according to an example embodiment. Hereinafter, the monoamine compound according to an example embodiment will be specifically explained, and then each layer of the organic electroluminescence device 10 will be explained.

In the present disclosure,

means a position to be connected.

In the present disclosure, "substituted or unsubstituted" may mean unsubstituted or substituted with at least one substituent selected from the group of deuterium, halogen, cyano, nitro, silyl, boron, phosphine, alkyl, alkenyl, aryl, and heterocyclic group. In addition, each substituent described above may be substituted or unsubstituted. For example, biphenyl may be interpreted as aryl, or phenyl substituted with phenyl.

In the present disclosure, the term to "form a ring by combining adjacent groups with each other" may mean forming a substituted or unsubstituted hydrocarbon ring, or a substituted or unsubstituted heterocycle by combining adjacent groups with each other. The hydrocarbon ring includes an aliphatic hydrocarbon ring and an aromatic hydrocarbon ring. The heterocycle includes an aliphatic heterocycle and an aromatic heterocycle. The hydrocarbon ring and heterocycle may be a monocycle or a polycycle. In addition, the ring formed by combining adjacent groups may be connected with another ring to form a spiro structure.

In the present disclosure, the term "an adjacent group" may mean a substituent at an atom which is directly connected with another atom at which a corresponding substituent is substituted, another substituent at an atom at which a corresponding substituent is substituted, or a substituent stereoscopically disposed at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, examples of a halogen atom are a fluorine atom, a chlorine atom, a bromine atom, and an iodine atom.

In the present disclosure, the alkyl group may have a linear, branched or cyclic form. The carbon number of the alkyl group may be 1 to 30, 1 to 20, 1 to 10, or 1 to 4. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl. 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc.

In the present disclosure, the aryl group means any functional group or substituent derived from an aromatic hydrocarbon ring. The aryl group may be monocyclic aryl or polycyclic aryl. The carbon number of the aryl group for forming a ring may be 6 to 30, 6 to 20, or 6 to 12. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc.

In the present disclosure, the fluorenyl group may be substituted, and two substituents may be combined with each other to form a spiro structure. Examples of the substituted fluorenyl group may include the following groups:

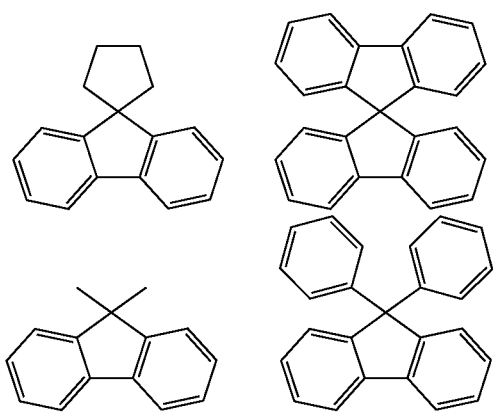

In the present disclosure, the heteroaryl group may be heteroaryl including at least one of O, N, P, Si, or S as a heteroatom. When the heteroaryl group includes two heteroatoms, the two heteroatoms may be the same or different from each other. The carbon number of the heteroaryl group for forming a ring may be 2 to 30, or 5 to 12. The heteroaryl group may be monocyclic heteroaryl or polycyclic heteroaryl. Polycyclic heteroaryl may have bicyclic or tricyclic structure, for example. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-aryl carbazole, N-heteroaryl carbazole, N-alkyl carbazole, benzoxazole, benzoimidazole, benzothiazole, benzocarbazole, benzothiophene, dibenzothiophene, thienothiophene, benzofuran, phenanthroline, thiazole, isoxazole, oxadiazole, thiadiazole, phenothiazine, dibenzosilole, dibenzofuran, etc.

In the present disclosure, the silyl group may include alkyl silyl and aryl silyl. Examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc.

In the present disclosure, the boron group may include alkyl boron and aryl boron. Examples of the boron group may include trimethyl boron, triethyl boron, t-butyl dimethyl boron, triphenyl boron, diphenyl boron, phenyl boron, etc.

In the present disclosure, the alkenyl group may be linear or branched. The carbon number is not specifically limited, and may be 2 to 30, 2 to 20, or 2 to 10. Examples of the alkenyl group may include vinyl, 1-butenyl, 1-pentenyl, 1,3-butadienyl aryl, styrenyl, styrylvinyl, etc.

The above explanation on the aryl group may be applied to the arylene group, except that the arylene group is divalent.

The above explanation on the heteroaryl group may be applied to the heteroarylene group, except that the heteroarylene group is divalent.

A monoamine compound according to an example embodiment is represented by the following Formula 1.

[Formula 1]

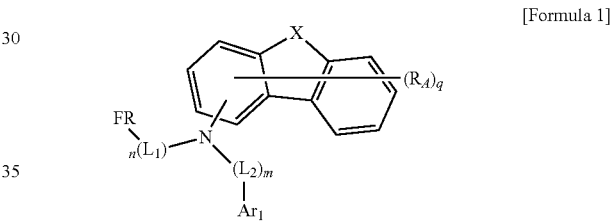

According to the present example embodiment, in Formula 1, X may be S, O or CRR', R and R' may each independently be a substituted or unsubstituted alkyl group having 1 to 10 carbon atoms, a substituted or unsubstituted aryl group having 6 to 20 ring carbon atoms, or a substituted or unsubstituted heteroaryl group having 2 to 10 ring carbon atoms, and are separate or form a ring by combining adjacent groups with each other, $L_1$ and $L_2$ may each independently be a direct linkage, a substituted or unsubstituted arylene group having 6 to 12 ring carbon atoms, or a substituted or unsubstituted heteroarylene group having 2 to 12 ring carbon atoms, n and m may each independently be an integer of 0 to 2, $R_A$ may be a hydrogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, q may be an integer of 0 to 7, $Ar_1$ may be a substituted or unsubstituted aryl group having 6 to 12 ring carbon atoms, or a substituted or unsubstituted heteroaryl group having 2 to 12 ring carbon atoms, and in case X is CRR', $Ar_1$ may not include a heteroaryl group.

When $Ar_1$ is referred to as not including a heteroaryl group, it may include both the case where $Ar_1$ is not a heteroaryl group and the case where $Ar_1$ is not substituted with a heteroaryl group.

In Formula 1, when n is 2, two $L_1$'s may be the same or different from each other, and when m is 2, two $L_2$'s may be the same or different from each other.

In Formula 1, when q is an integer of 2 or more, a plurality of $R_A$ may be the same or different from each other, and when q is 1, $R_A$ may not be a hydrogen atom.

According to the present example embodiment, in Formula 1, FR is a naphthylene group substituted with one phenyl group. Although FR may be additionally substituted, the additional substituents do not include a phenyl group. In an example embodiment, FR is represented by the following Formula 2.

[Formula 2]

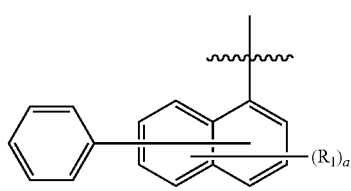

In Formula 2, $R_1$ is a hydrogen atom, a deuterium atom, or a halogen atom, and a is an integer of 0 to 6. When a is an integer of 2 or more, a plurality of $R_1$ may be the same or different from each other. In an example embodiment, when a is 1, $R_1$ may not be a hydrogen atom.

The compound of Formula 1, where FR is represented by Formula 2, may be advantageously applied to an organic electroluminescence device to improve efficiency of the device.

In an example embodiment, FR may be represented by the following Formula 2-1.

[Formula 2-1]

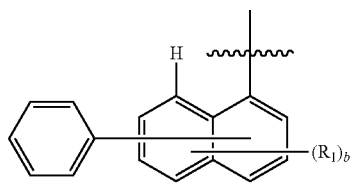

In Formula 2-1, b is an integer of 0 to 5, and $R_1$ is the same as defined above.

FR may be represented by any one of the following formulae, for example.

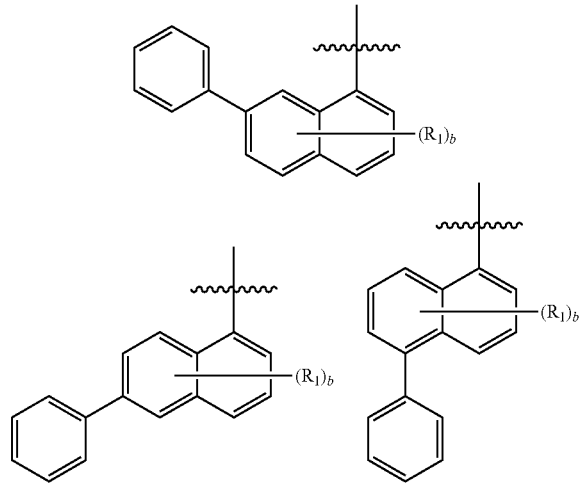

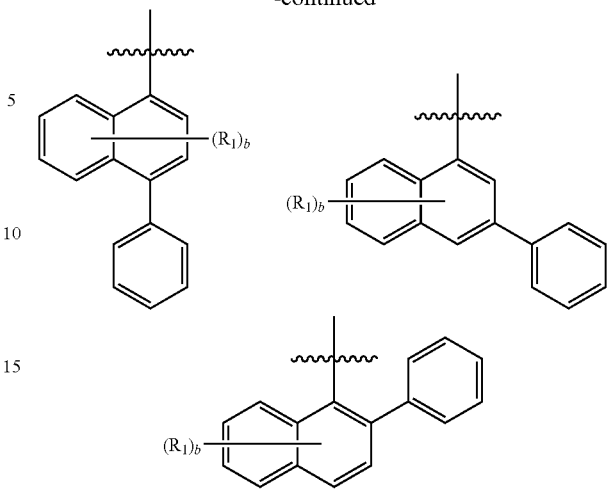

In Formula 2-1, $R_1$ may be, for example, a hydrogen atom or a deuterium atom.

In Formula 2, a may be 0. In another example embodiment, a may be 1, and $R_1$ may be a fluorine atom. In another example embodiment, a may be an integer of 2 or more, and a plurality of $R_1$ may be each independently a deuterium atom.

In Formula 1, n may be 1, and $L_1$ may be a substituted or unsubstituted arylene group having 6 to 12 ring carbon atoms. For example, $L_1$ may be a substituted or unsubstituted phenylene group.

In Formula 1, when $L_1$ is a substituted or unsubstituted phenylene group, FR may be substituted at a para position of the phenylene relative to the nitrogen atom of the monoamine compound as shown, for example, in the following Formula 1-1.

In an example embodiment, Formula 1 may be represented by the following Formula 1-1.

[Formula 1-1]

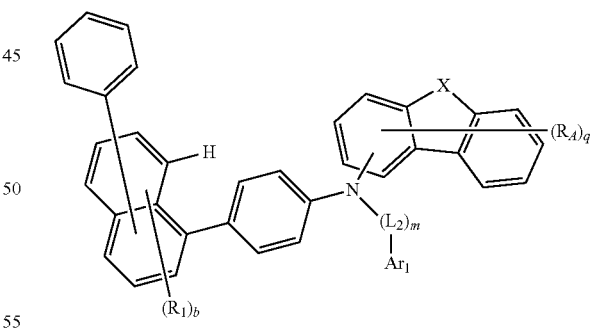

In Formula 1-1, X, $L_2$, $Ar_1$, $R_A$, $R_1$, q, m, and b are the same as defined above.

In Formula 1, $Ar_1$ may be a substituted or unsubstituted phenyl group, a substituted or unsubstituted biphenyl group, or a substituted or unsubstituted naphthyl group.

In Formula 1, when $Ar_1$ is a substituted or unsubstituted aryl group having 6 to 12 ring carbon atoms, m may be 1, and $L_2$ may be a substituted or unsubstituted arylene group having 6 to 12 ring carbon atoms. For example, $Ar_1$ may be a substituted or unsubstituted phenyl group, a substituted or unsubstituted biphenyl group, or a substituted or unsubstituted naphthyl group, and $L_2$ may be a substituted or unsubstituted phenylene group.

In Formula 1, when $Ar_1$ is a substituted or unsubstituted heteroaryl group having 5 to 12 ring carbon atoms, m may be 0. Thus, when $Ar_1$ is a heteroaryl group, $Ar_1$ may be directly connected to the nitrogen atom in Formula 1. For example, m may be 0, and $Ar_1$ may be a substituted or unsubstituted dibenzofuran group, or a substituted or unsubstituted dibenzothiophene group.

In Formula 1, q may be 0. For example, q may be 1, and $R_A$ may be a substituted or unsubstituted aryl group having 6 to 15 ring carbon atoms. In another example, q may be 1, and $R_A$ may be a substituted or unsubstituted phenyl group.

In Formula 1, when X is CRR', R and R' may be each independently a substituted or unsubstituted phenyl group, or a substituted or unsubstituted alkyl group having 1 to 5 carbon atoms. For example, R and R' may be each independently a substituted or unsubstituted phenyl group, or a substituted or unsubstituted methyl group. Furthermore, R and R' may be the same as each other.

The monoamine compound represented by Formula 1 according to an example embodiment may be any one selected from the group of compounds represented in the following Compound Group 1.

[Compound Group 1]

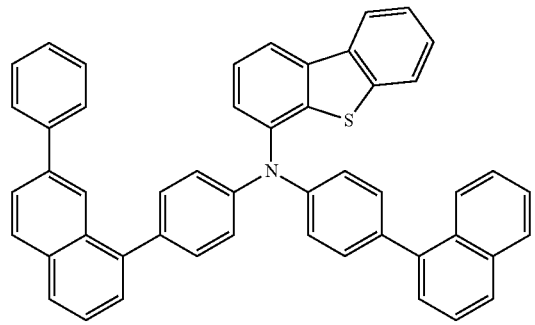

1

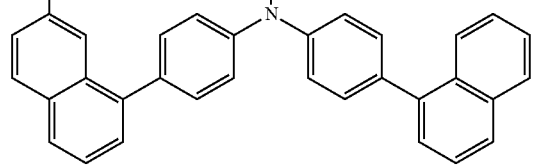

2

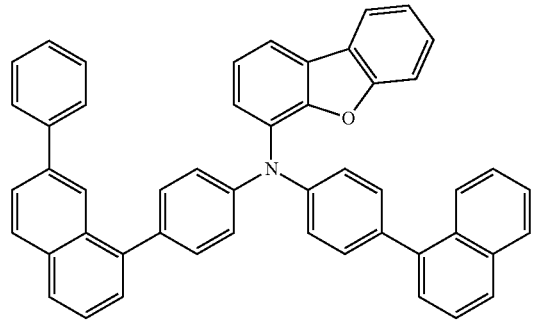

3

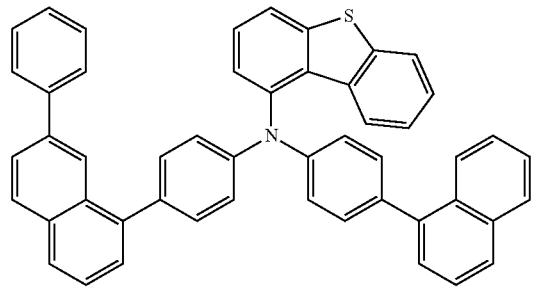

-continued

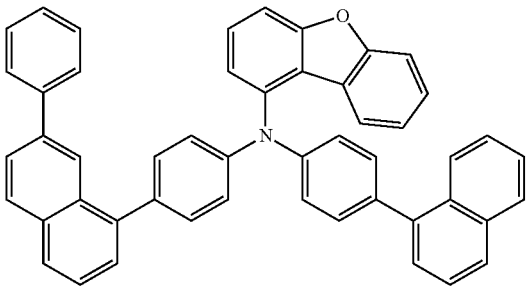

4

5

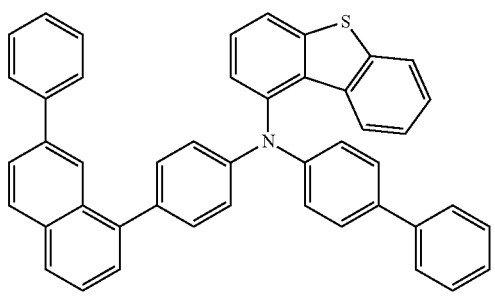

6

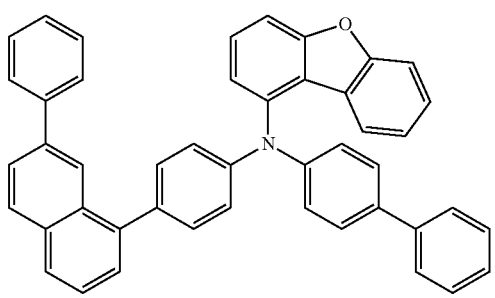

7

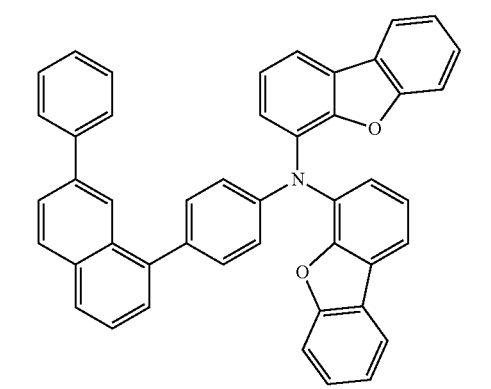

8

9
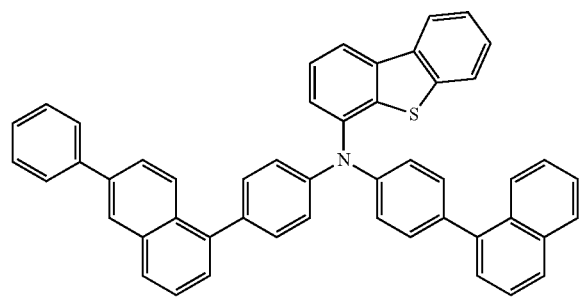
10
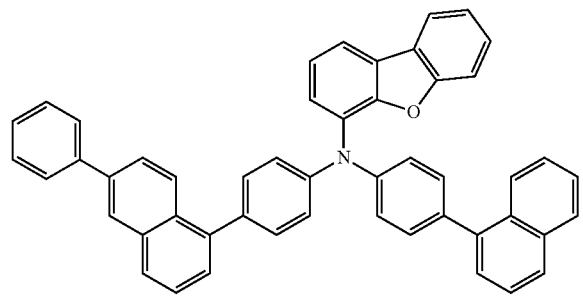
11
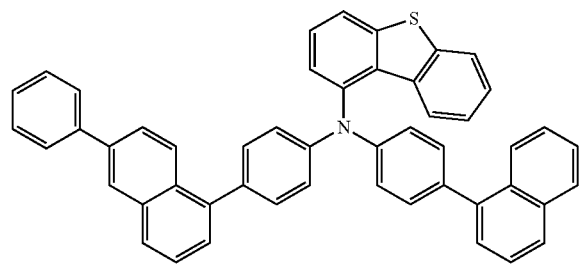
12
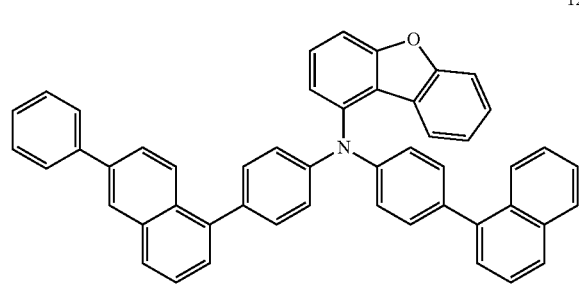
13
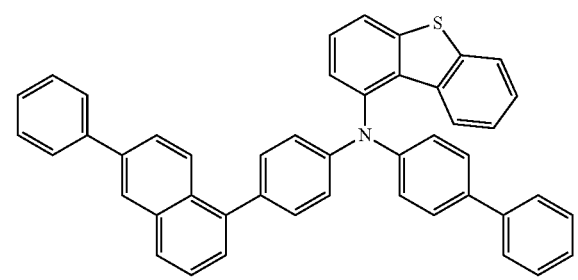
14
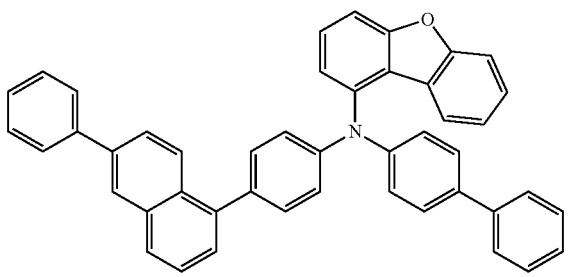
15
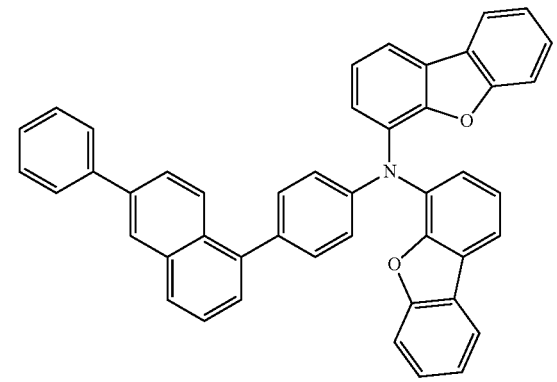
16
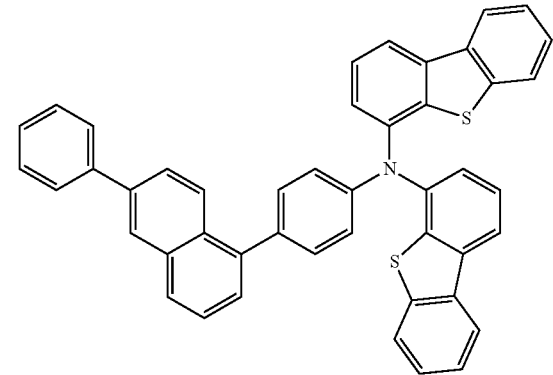
17
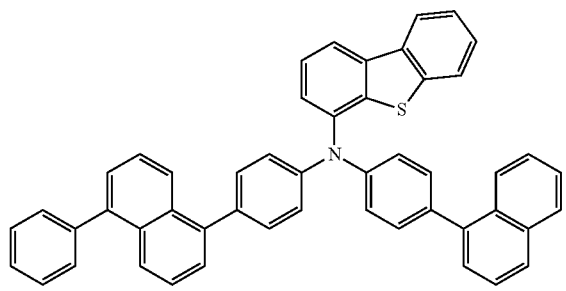

18
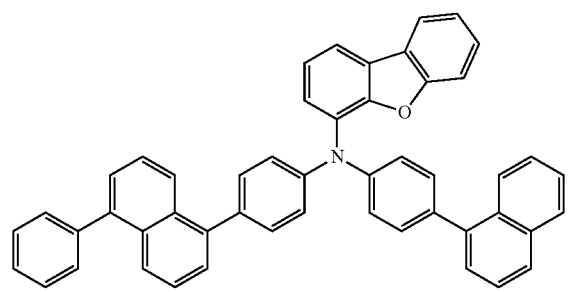
19
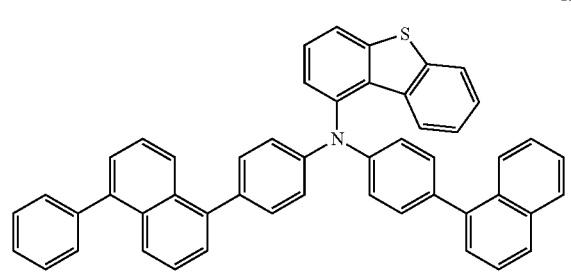
20
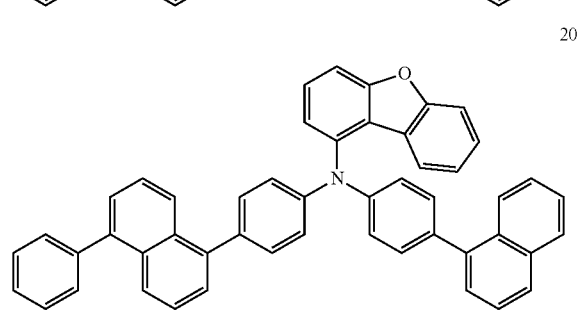
21
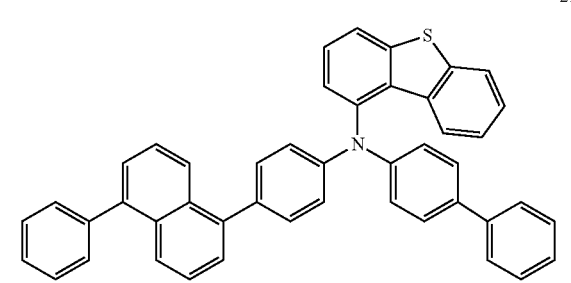
22
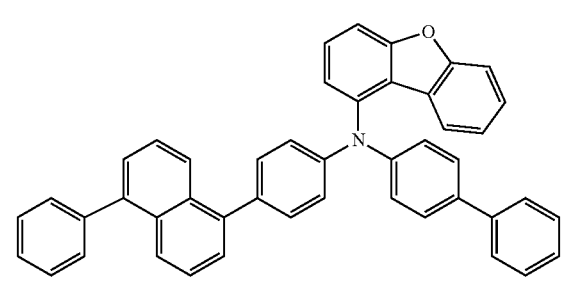
23
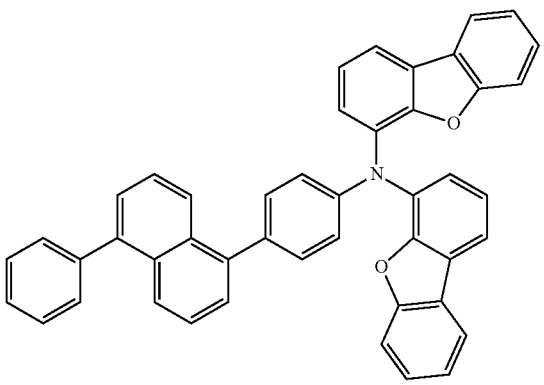
24
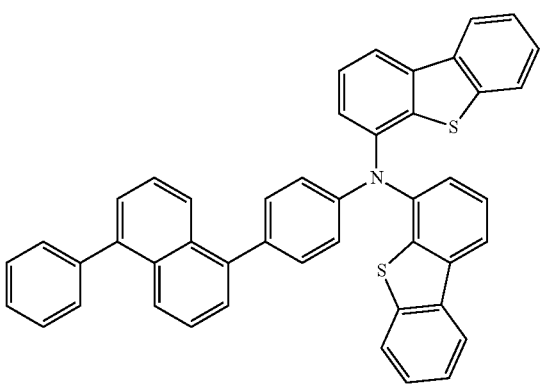
25
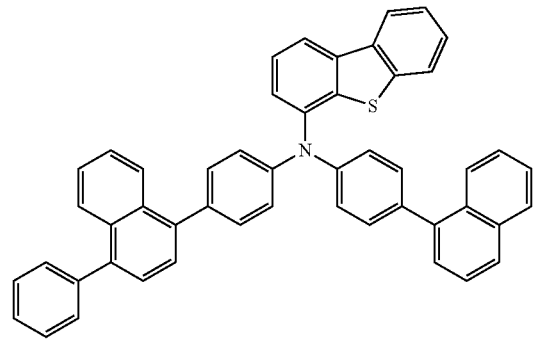
26
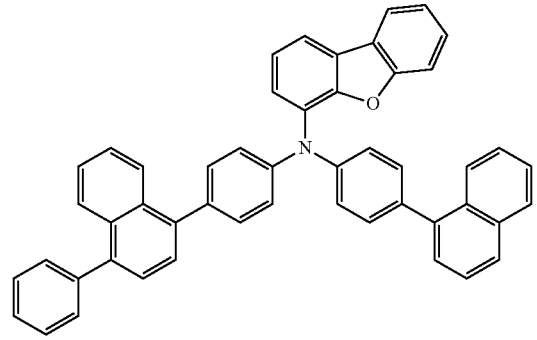

27
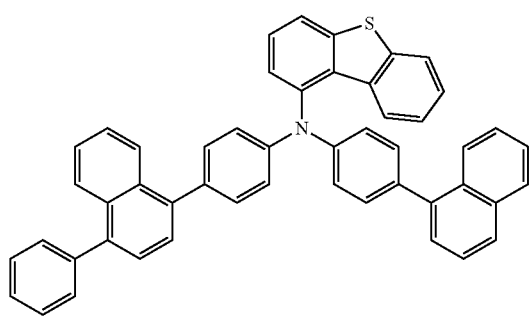
28
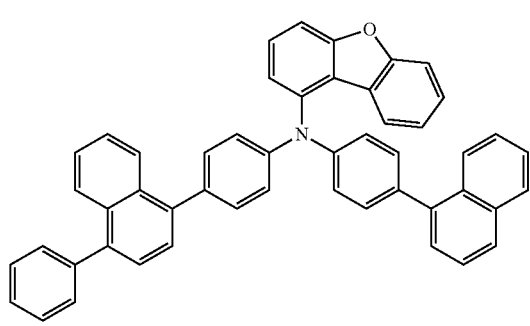
29
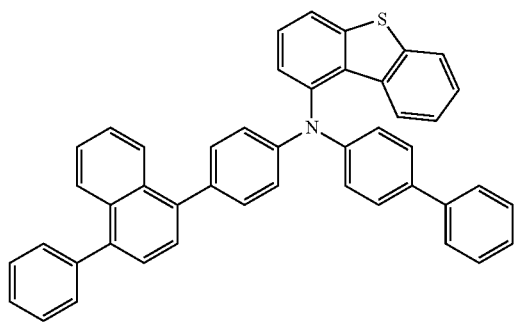
30
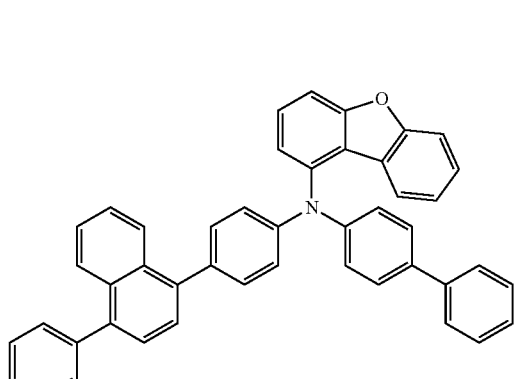
31
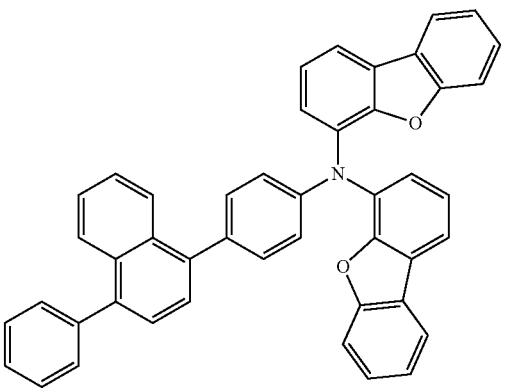
32
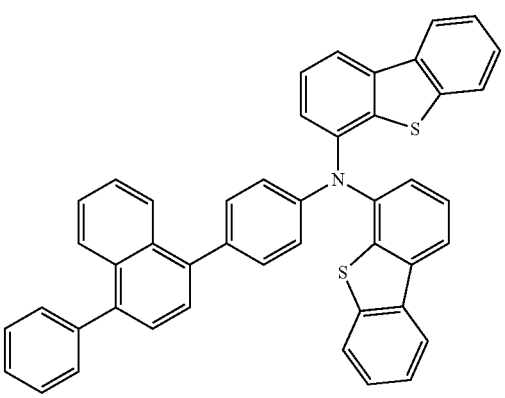
33
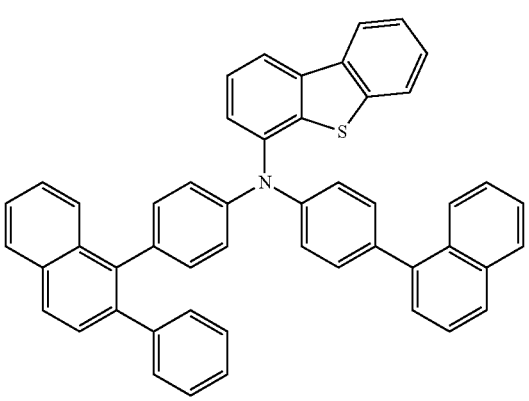
34
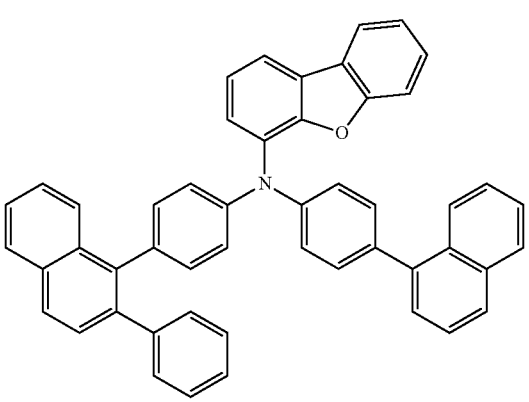

-continued
35
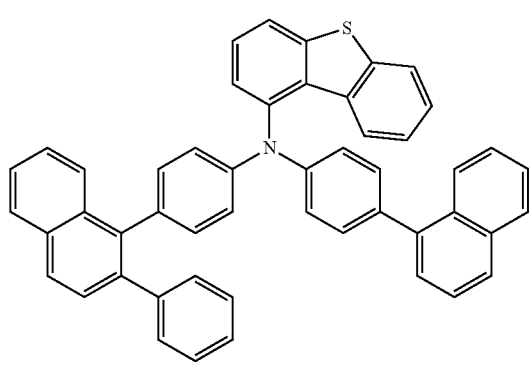
36
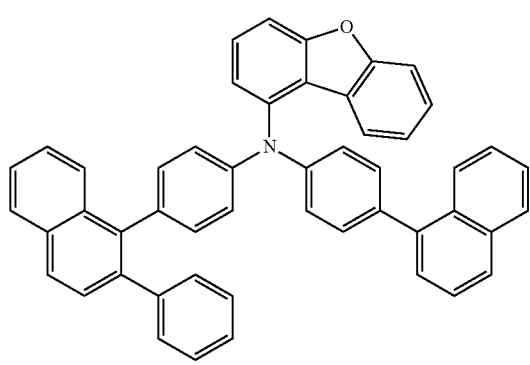
37
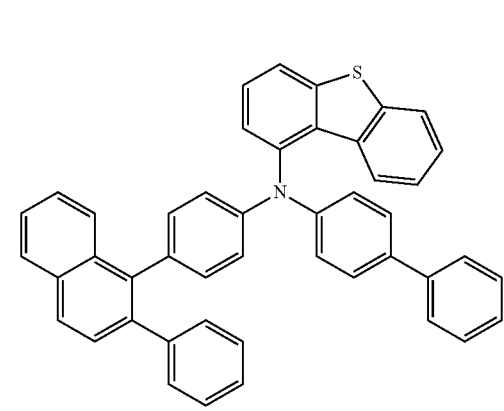
38
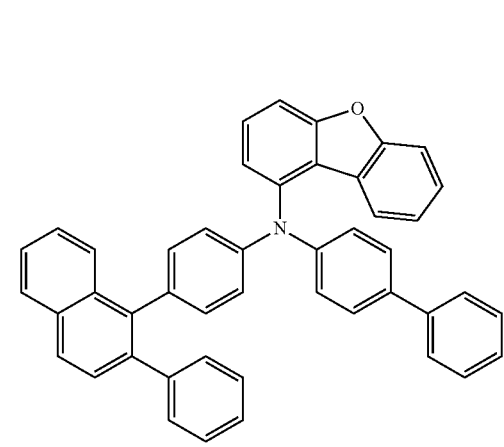
-continued
39
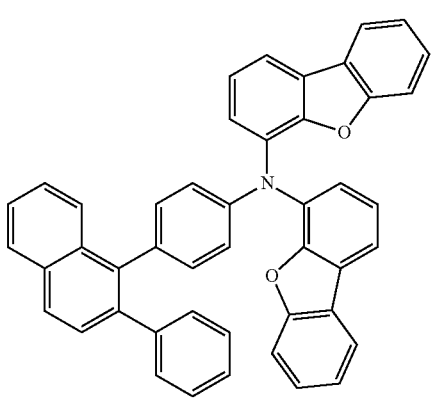
40
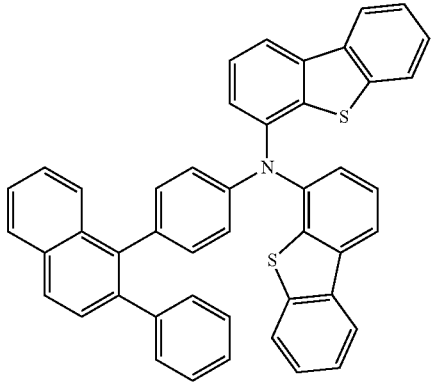
41
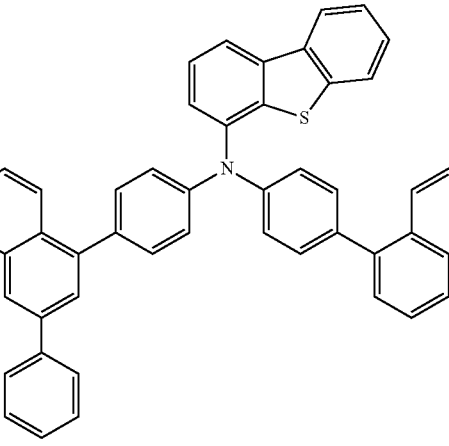

42
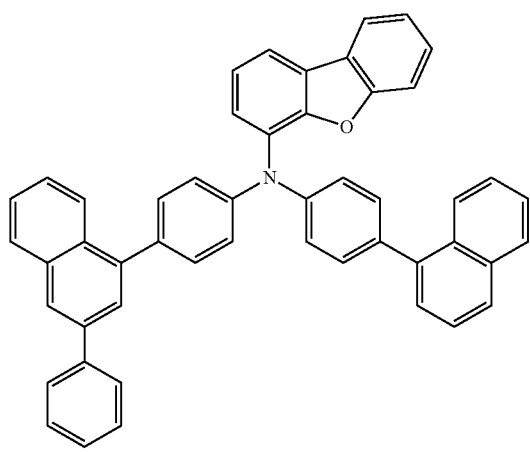
43
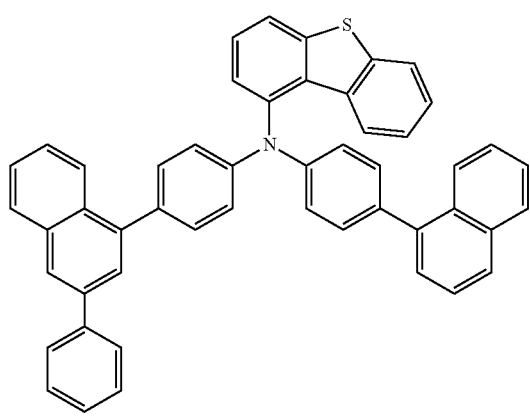
44
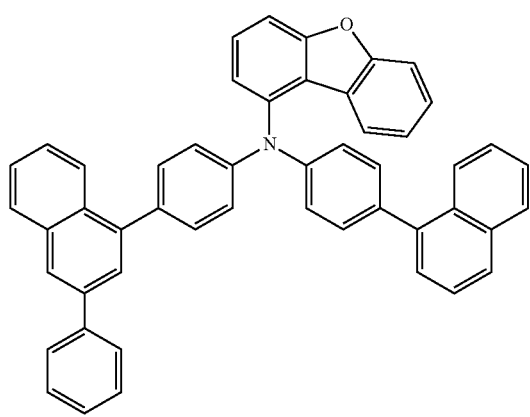
45
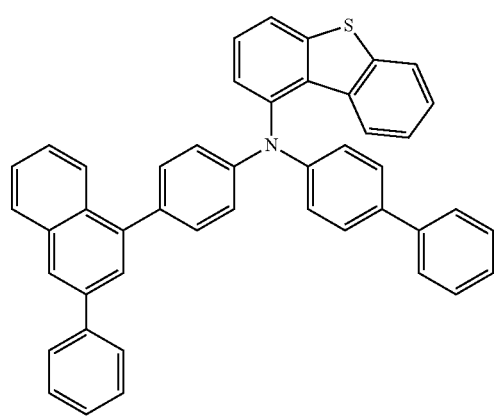
46
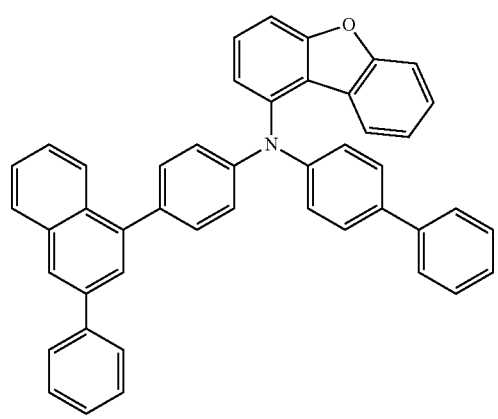
47
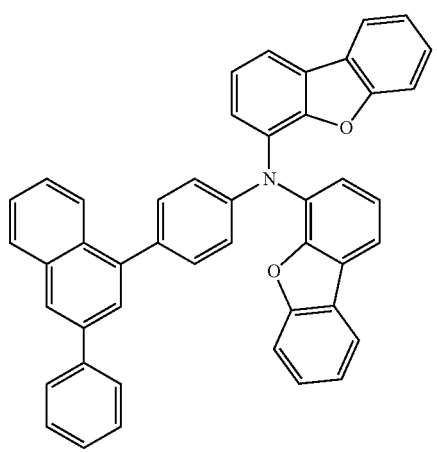

-continued
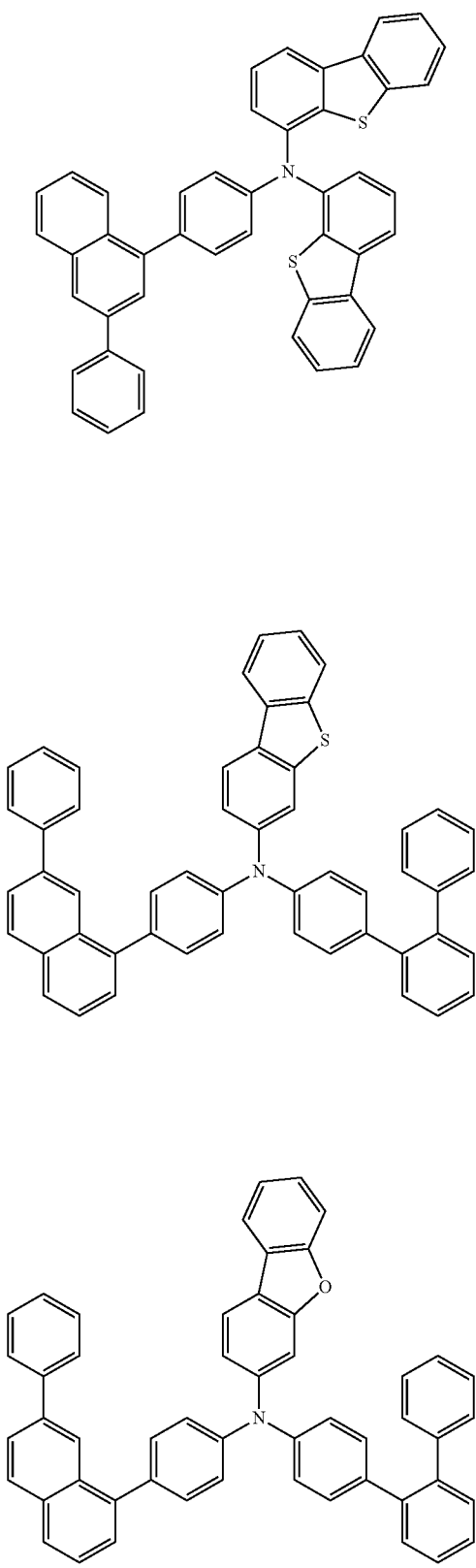
-continued
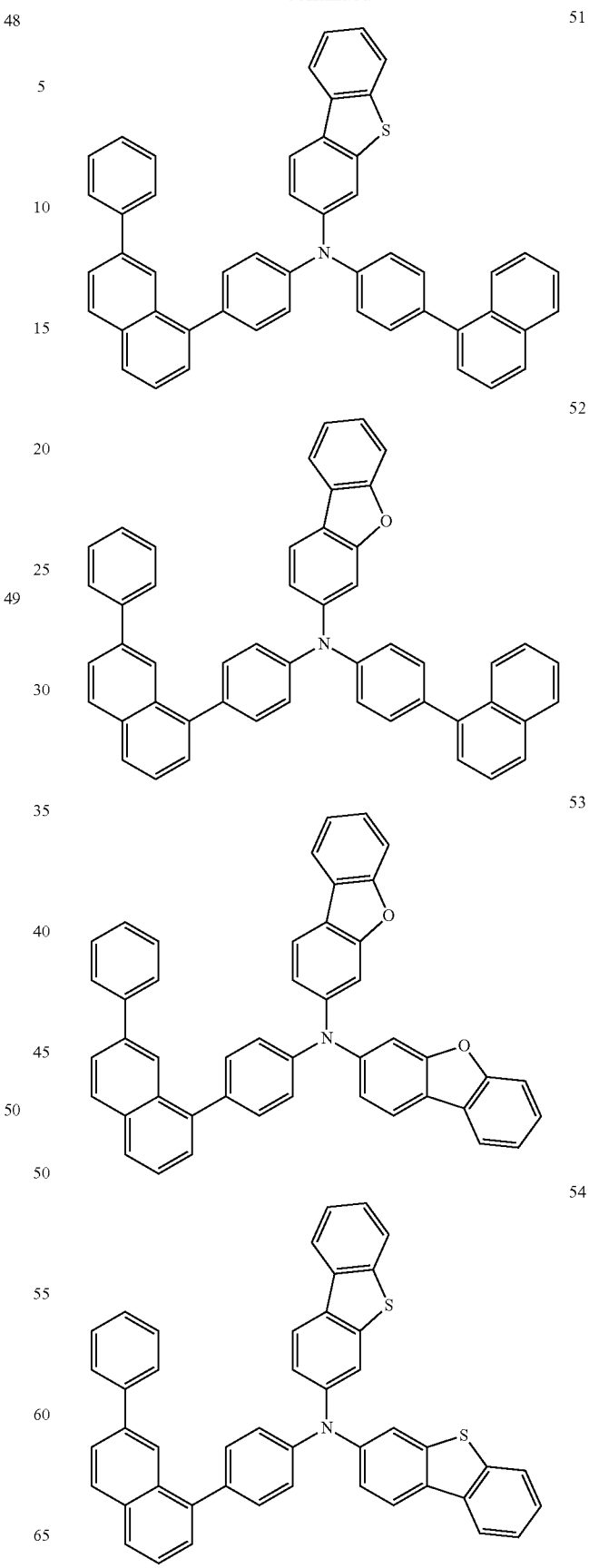

55
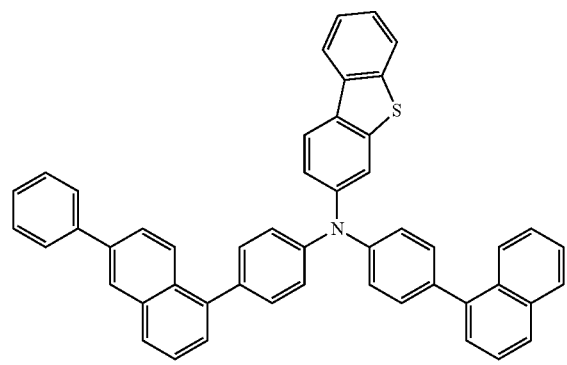
56
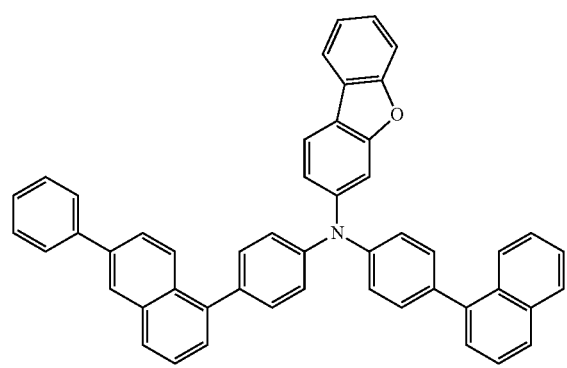
57
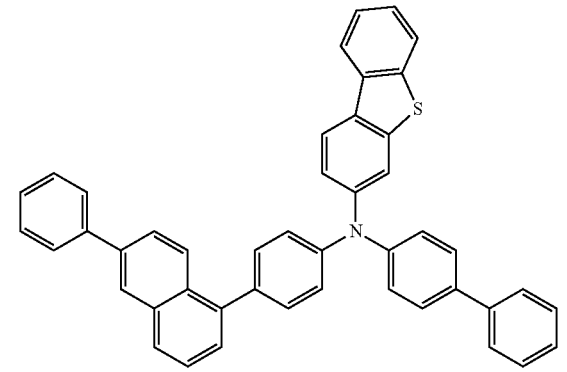
58
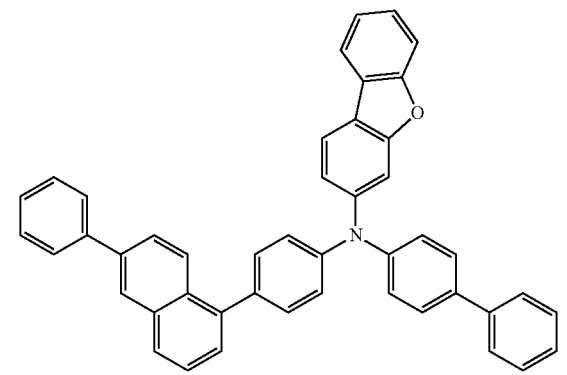
59
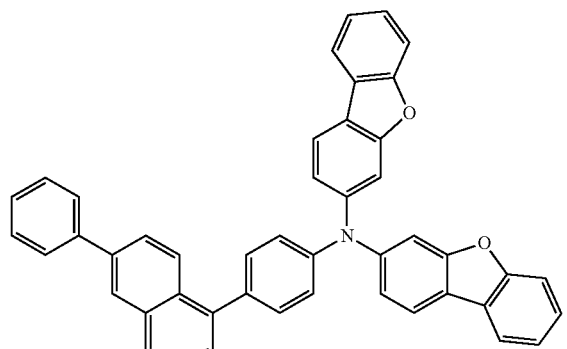
60
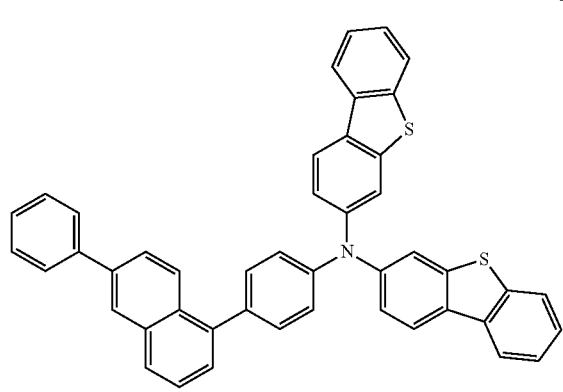
61
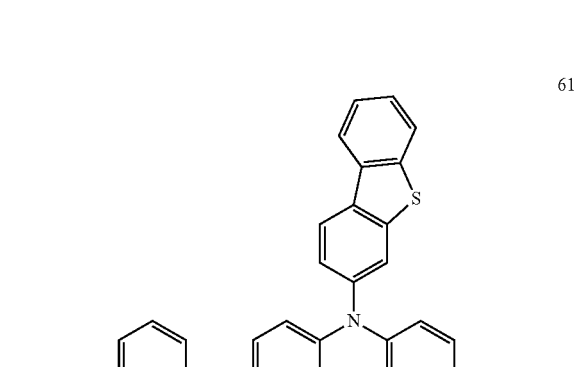
62
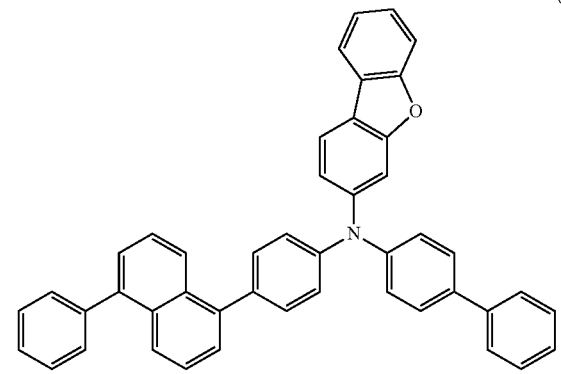

63
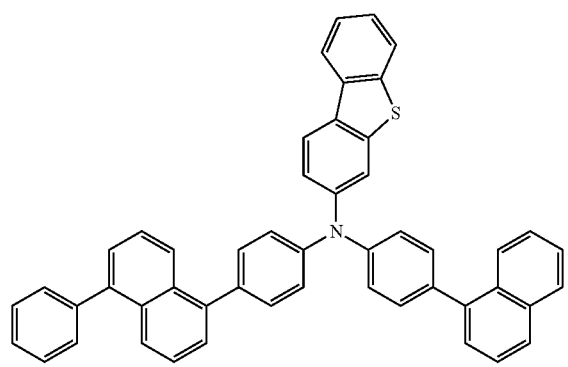
64
65
66
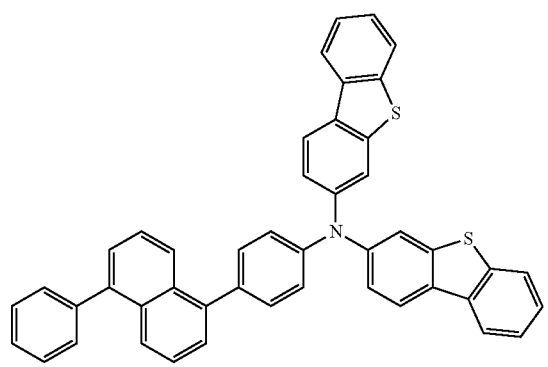
67
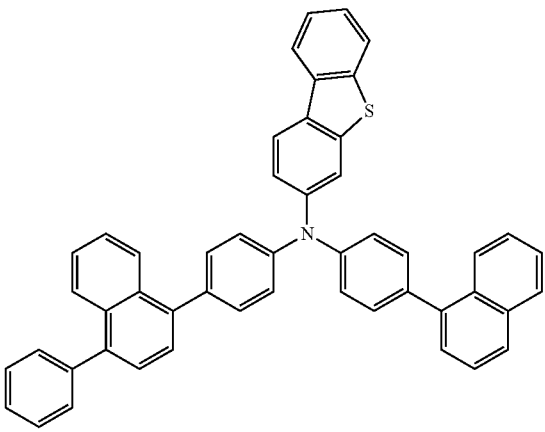
68
69
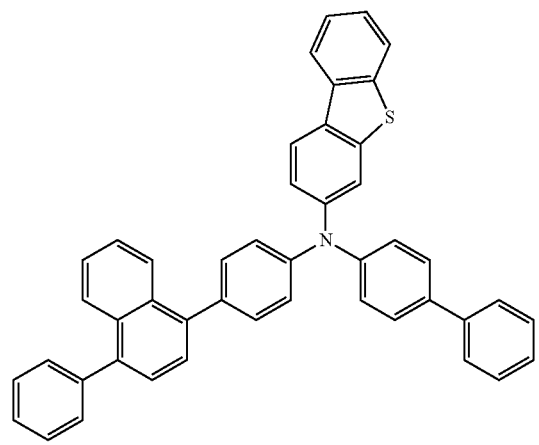

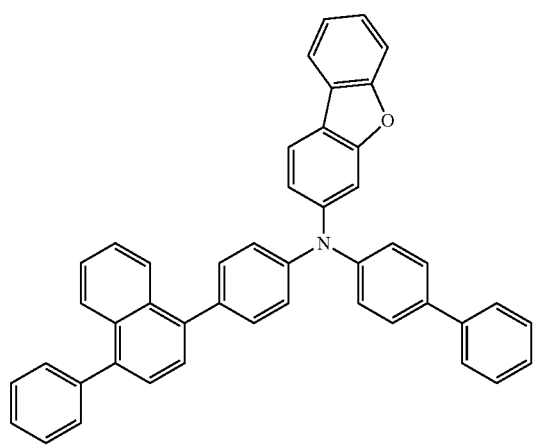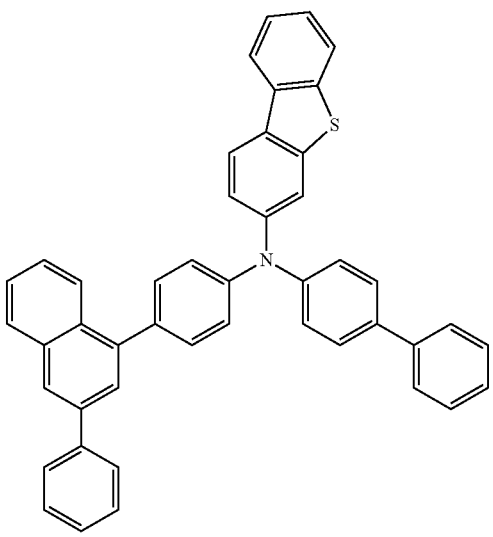

76
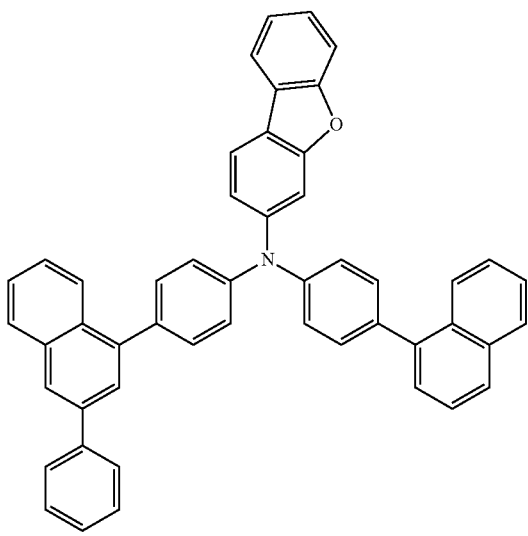
77
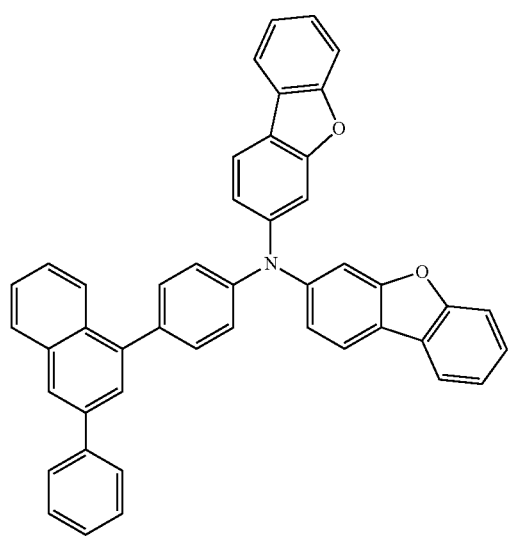
78
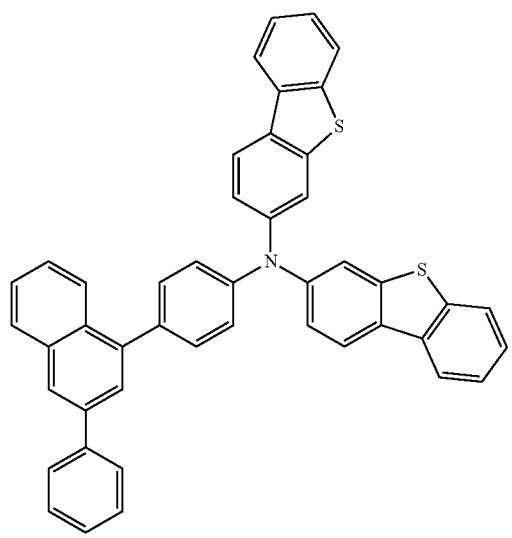
79
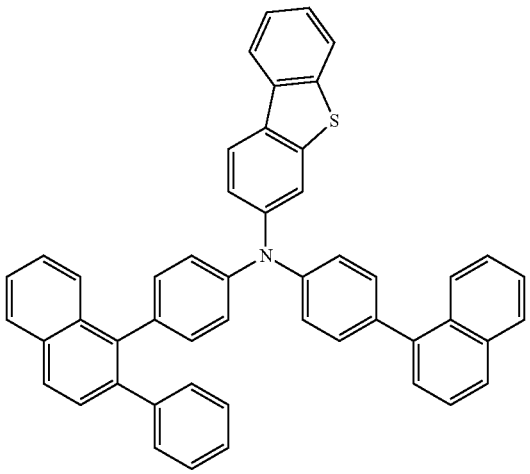
80
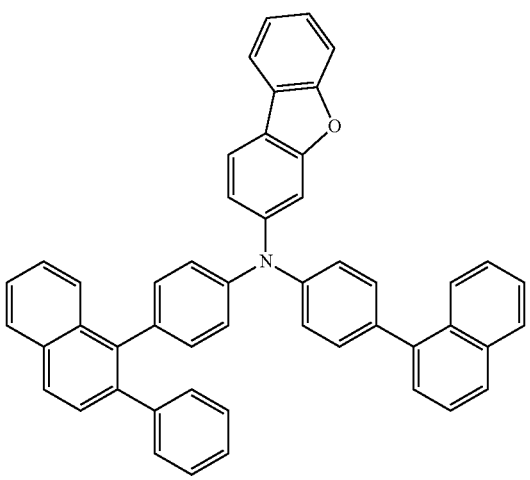
81

82
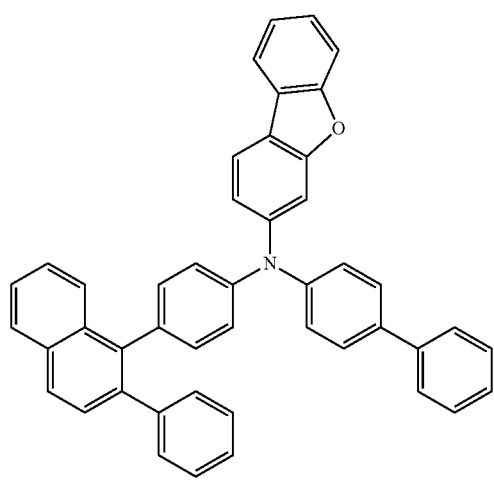
83
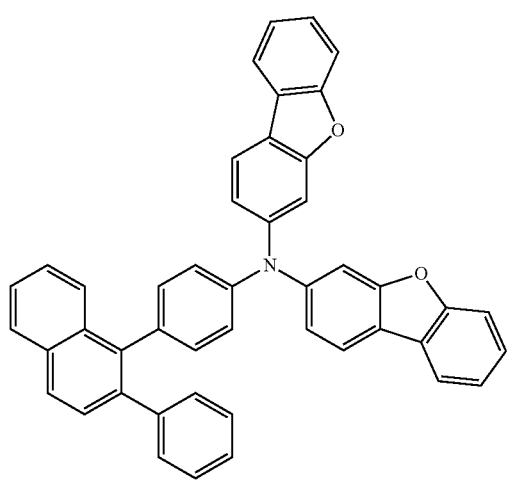
84
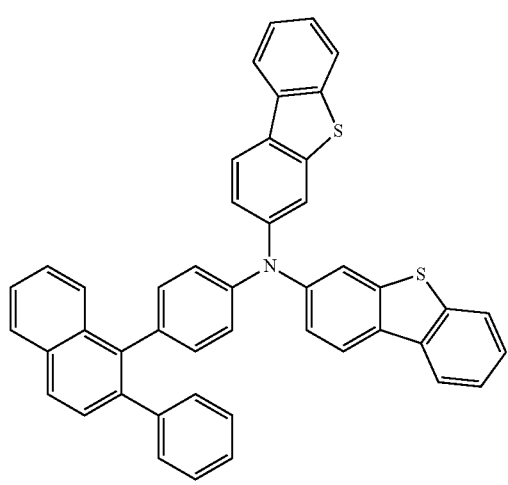
85
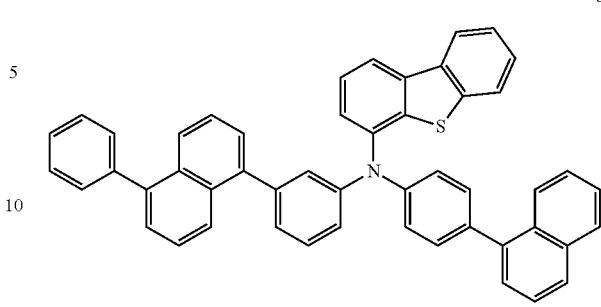
86
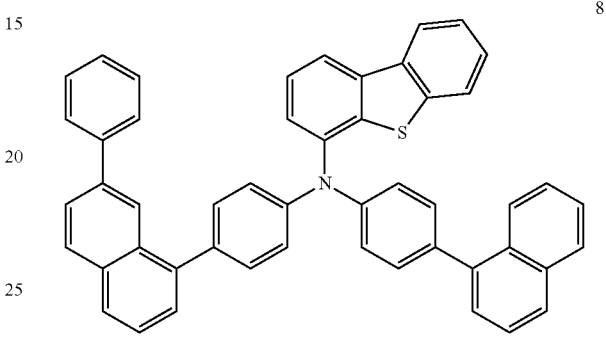
87
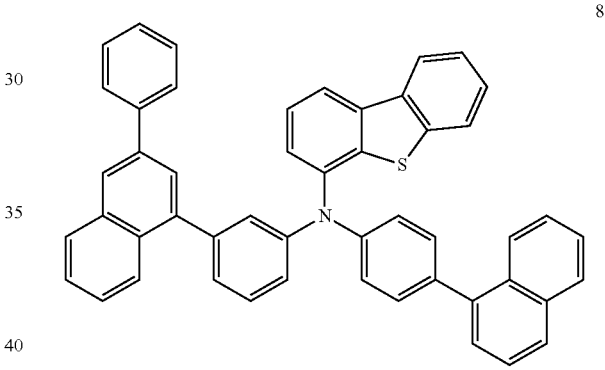
88
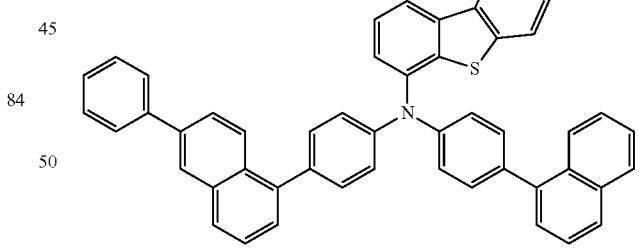
89
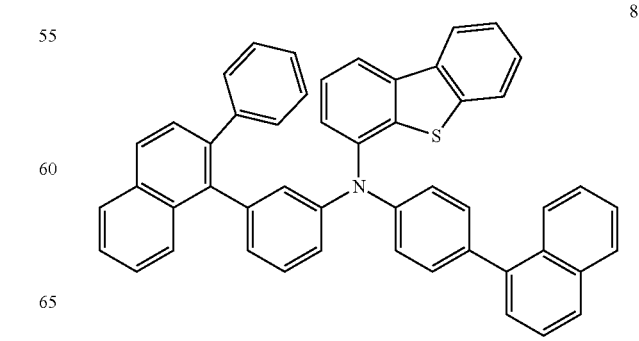

90
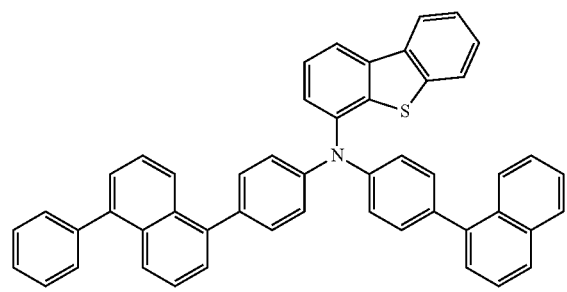
91
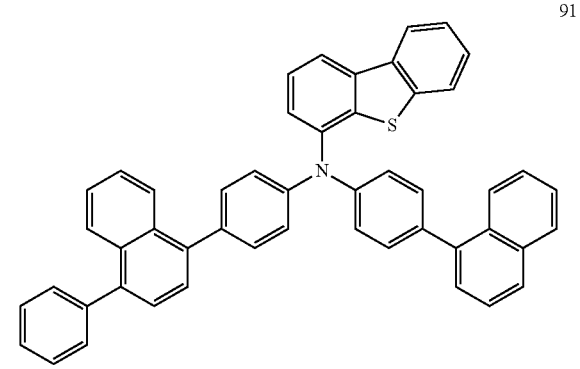
92
93
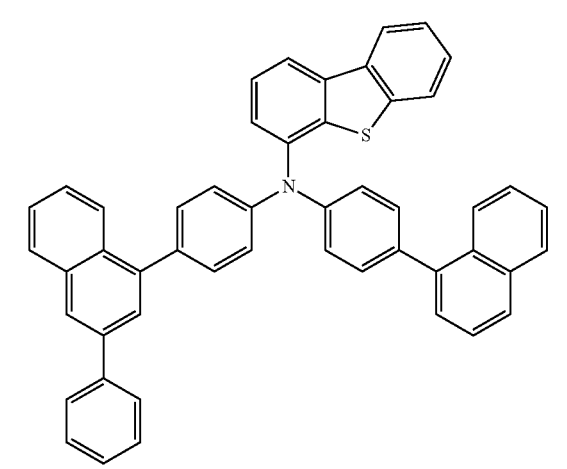
94
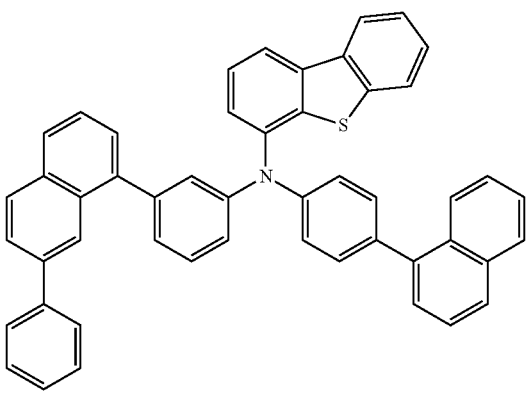
95
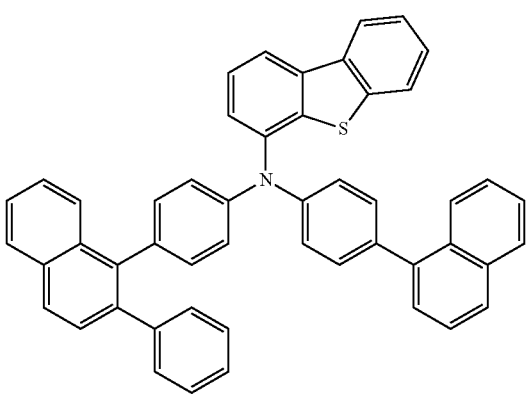
96
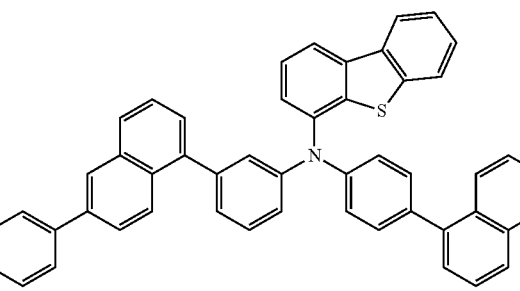
97
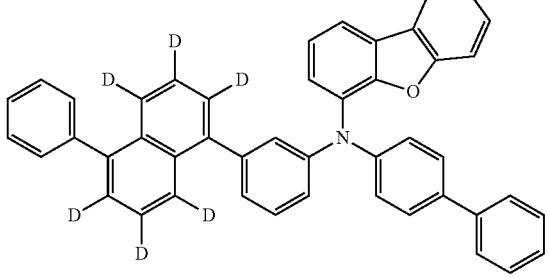

98
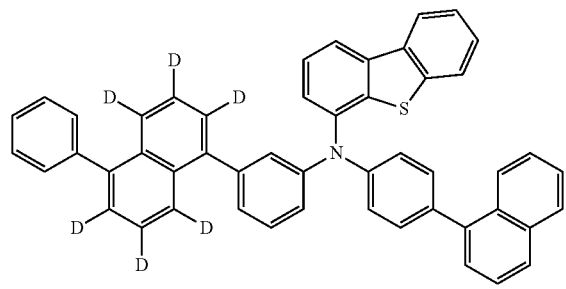
99
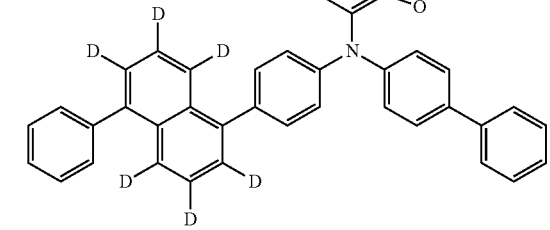
100
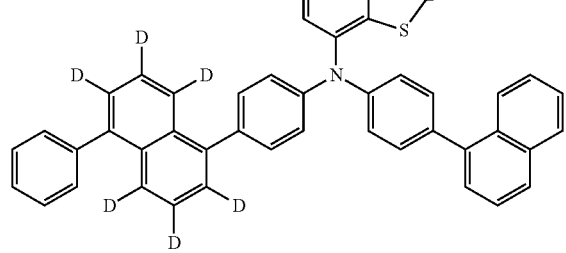
101
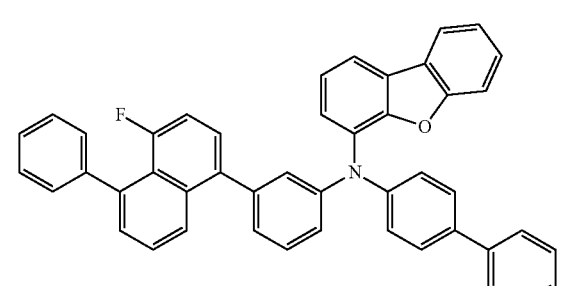
102
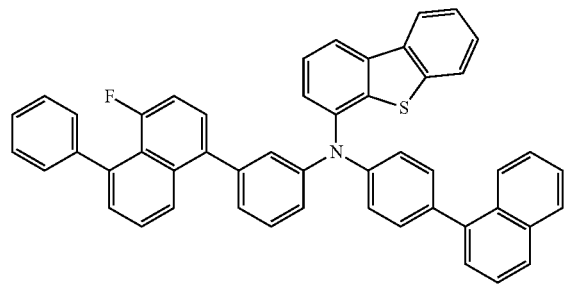
103
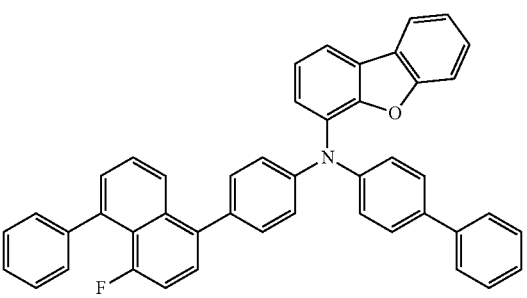
104
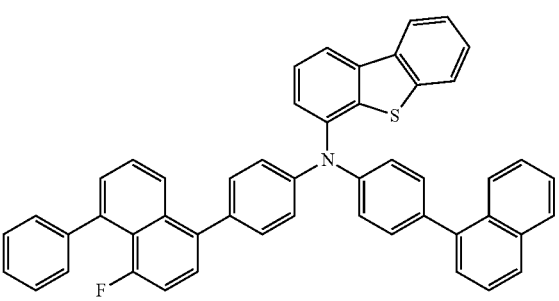
105
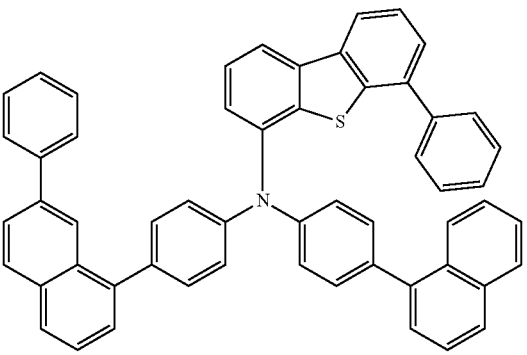
106
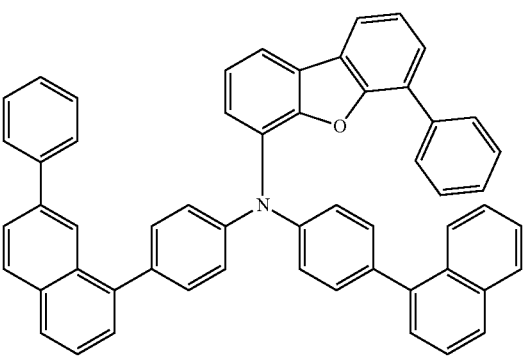

107
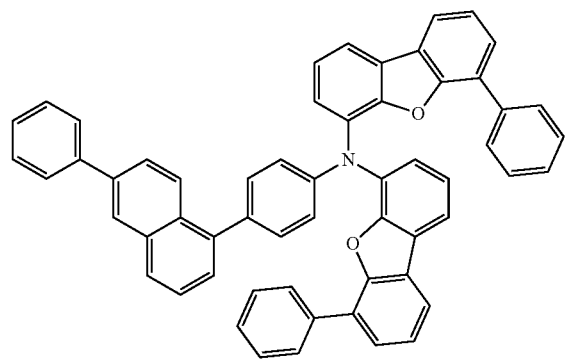
108
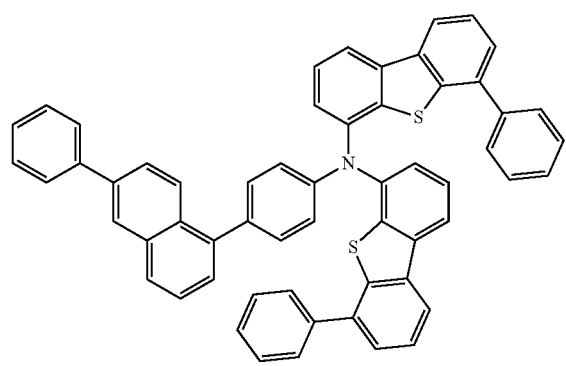
109
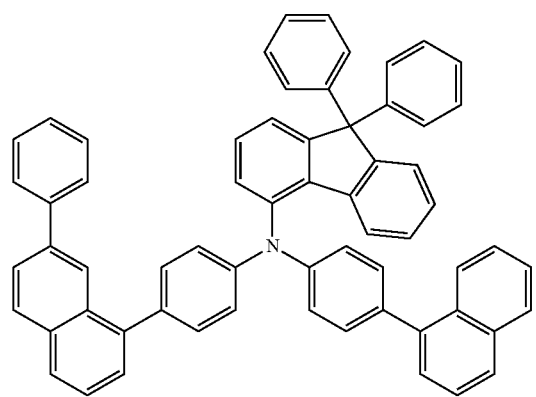
110
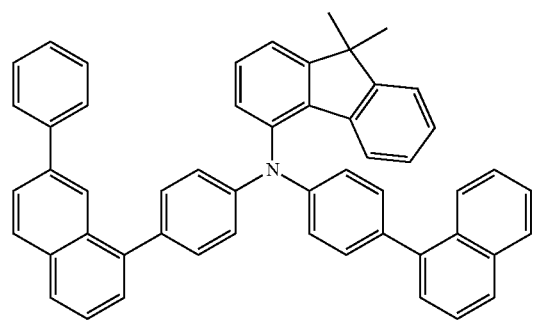
111
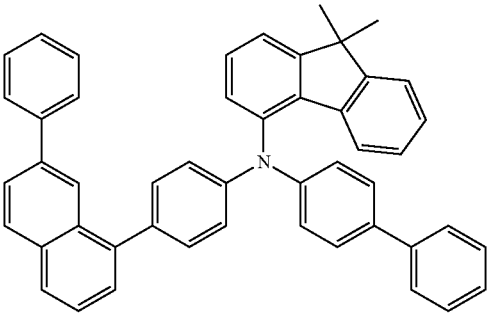
112
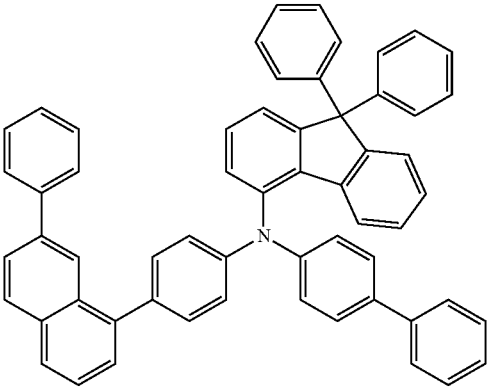
113
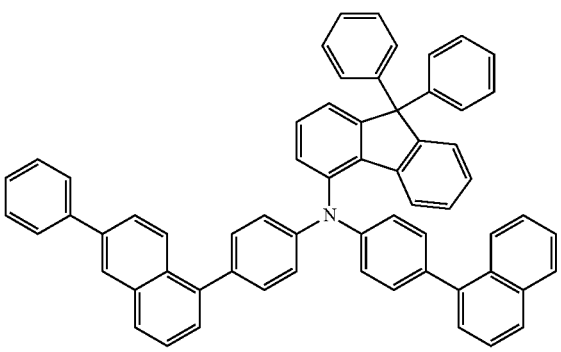
114
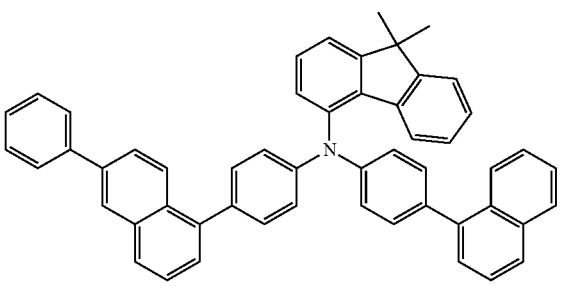

115
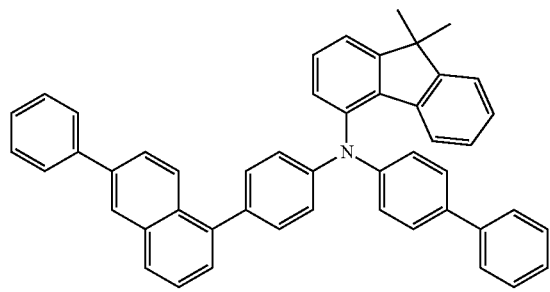
116
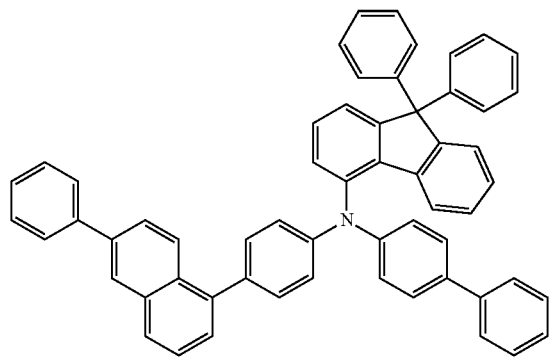
117
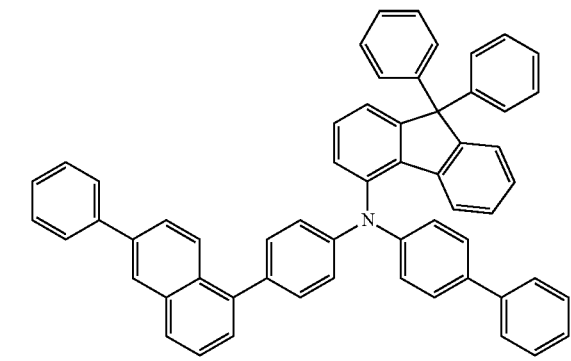
118
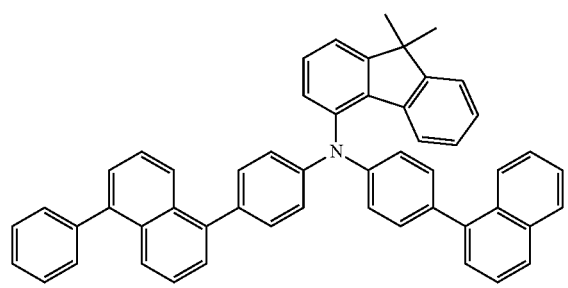
119
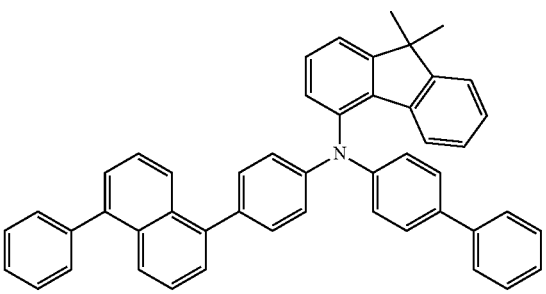
120
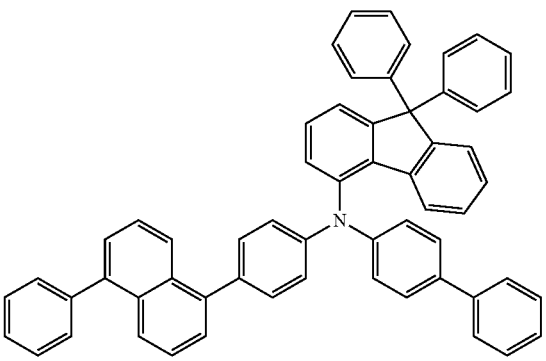
121
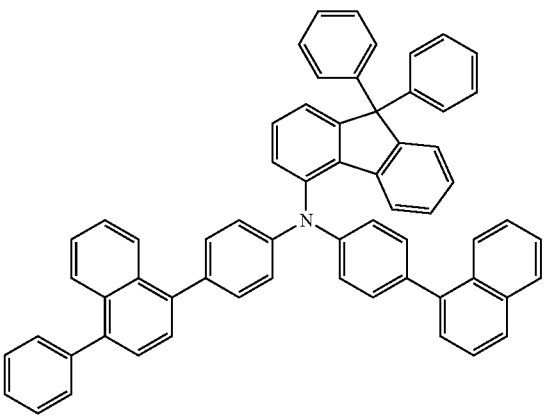
122
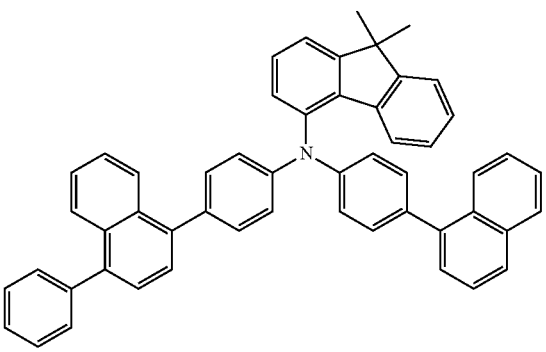

123
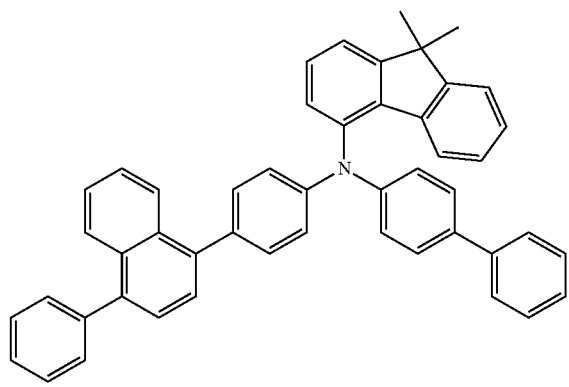
124
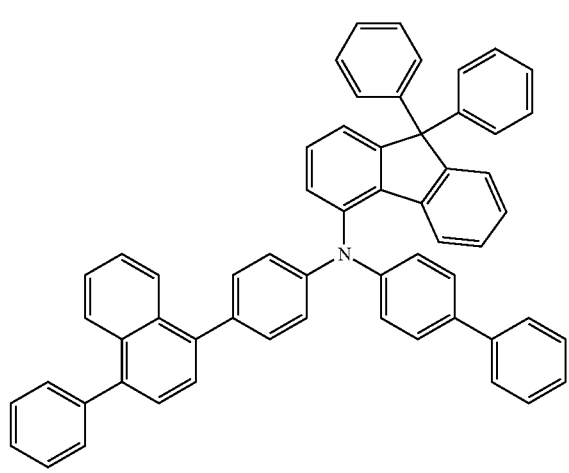
125
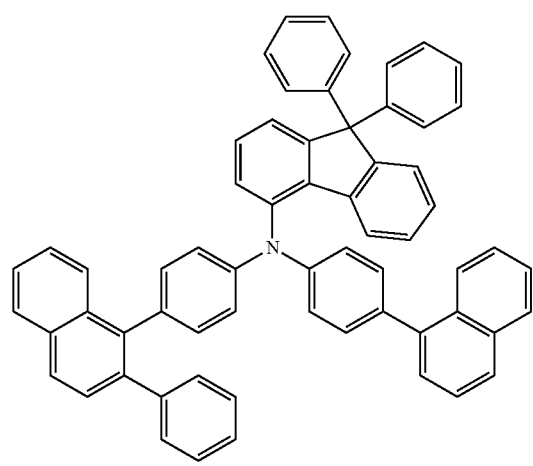
126
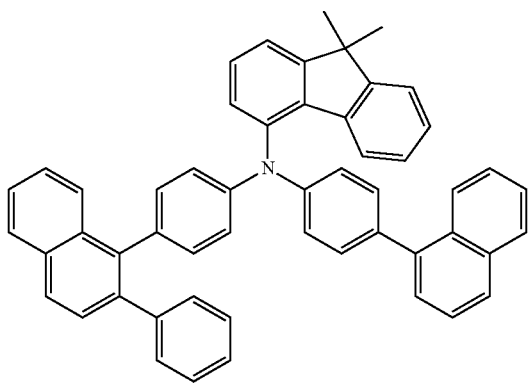
127
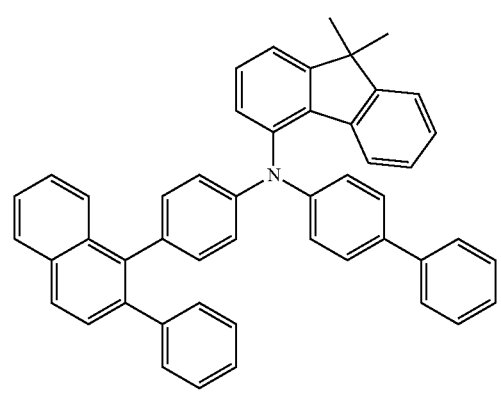
128
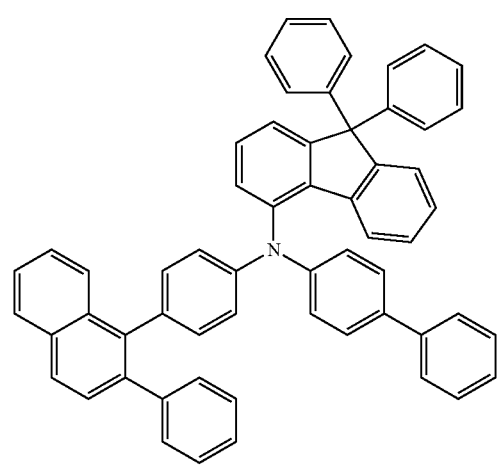

129
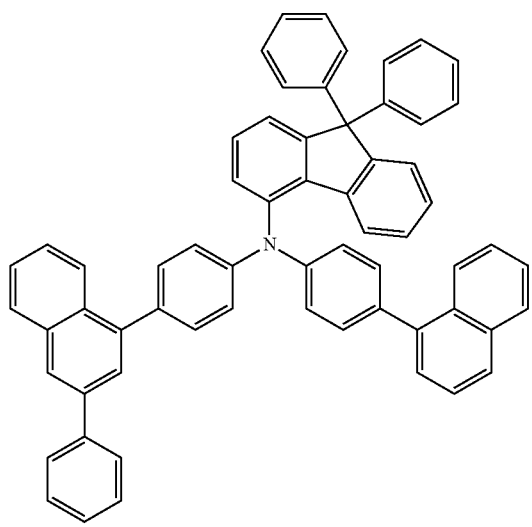
130
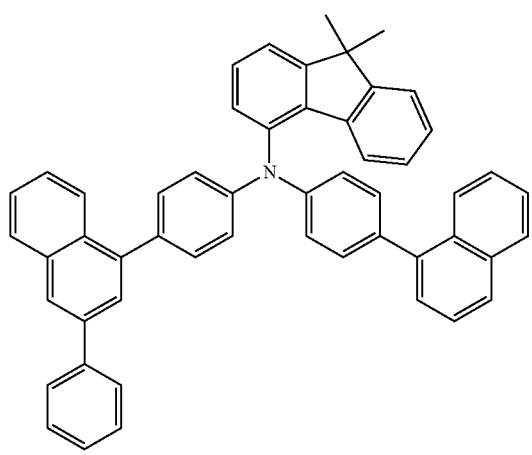
131
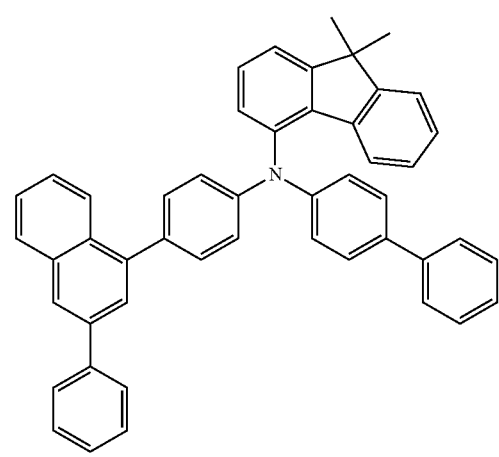
132
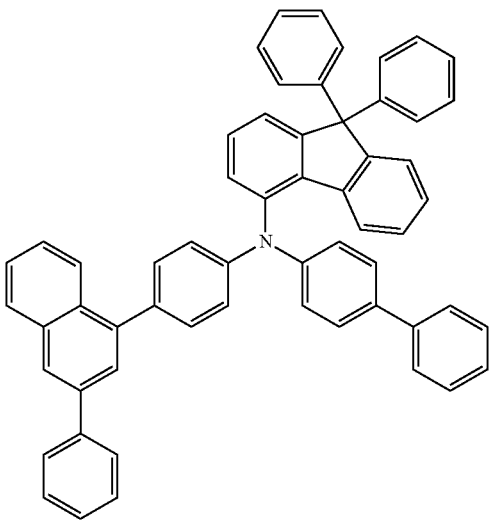
133
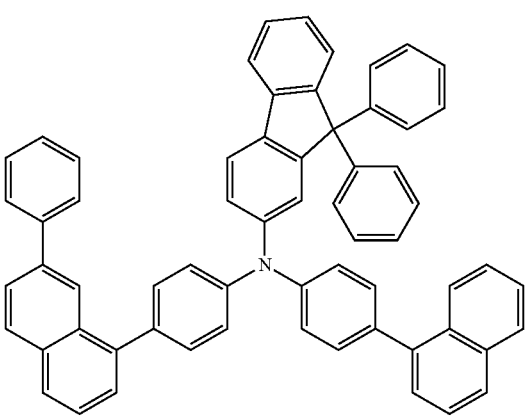
134
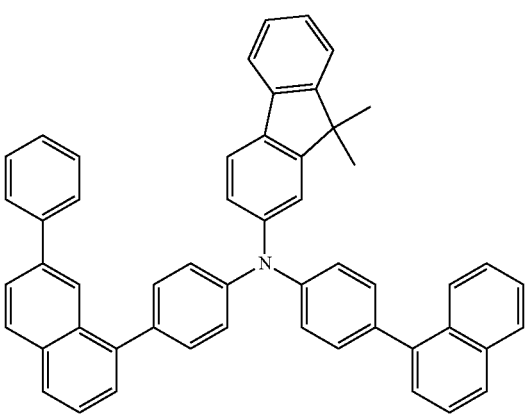

135
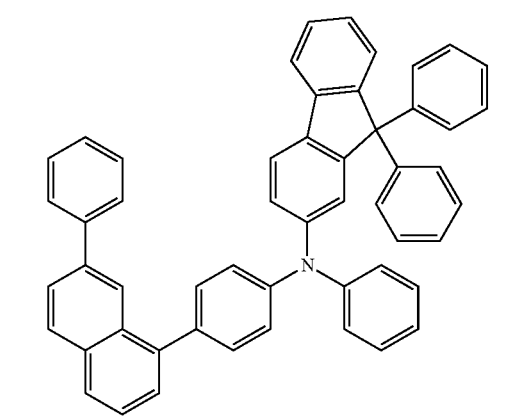
136
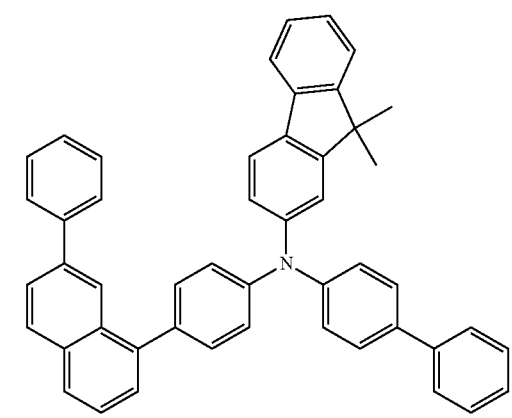
137
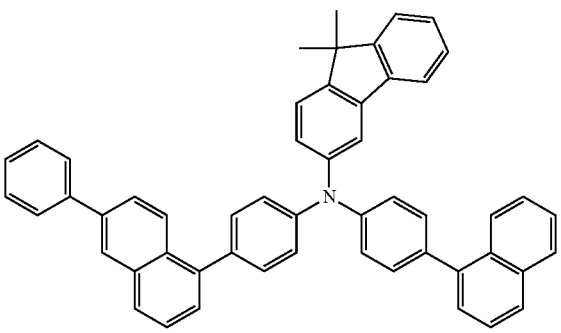
138
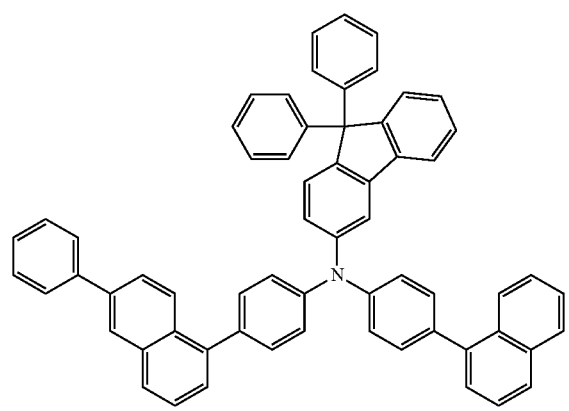
139
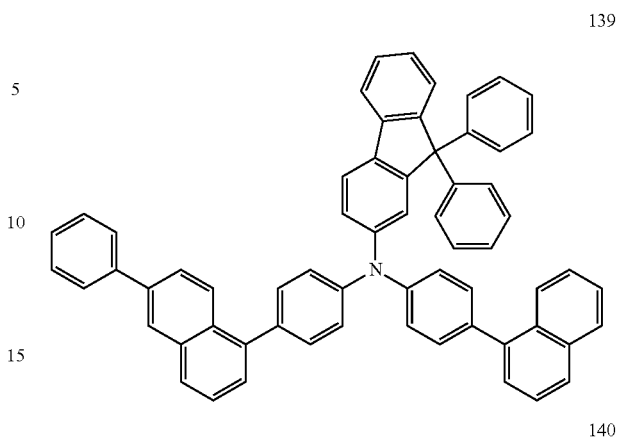
140
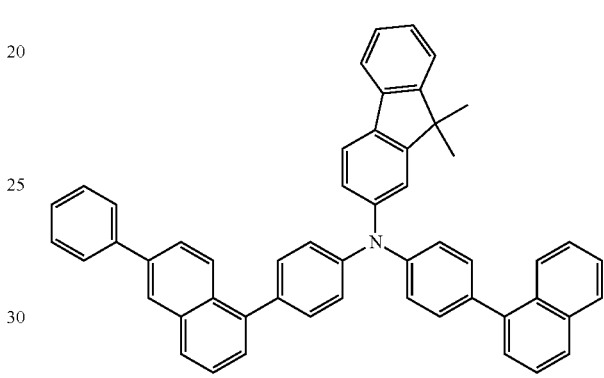
141
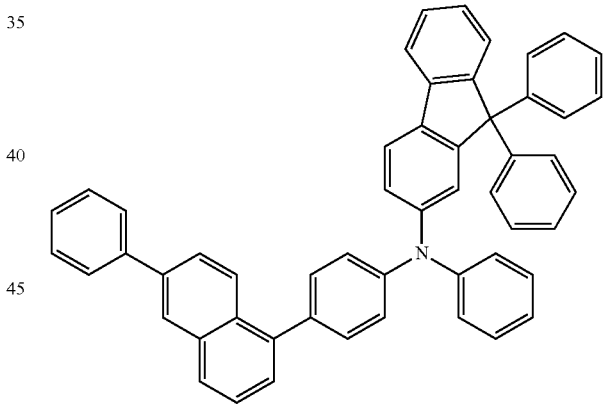
142
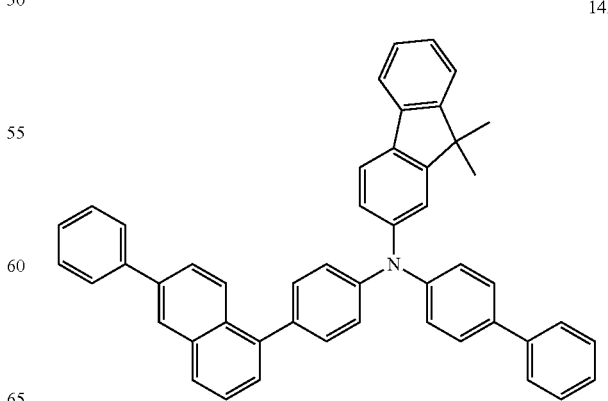

143
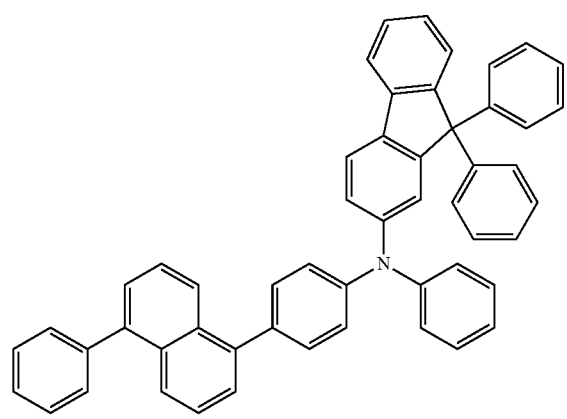
144
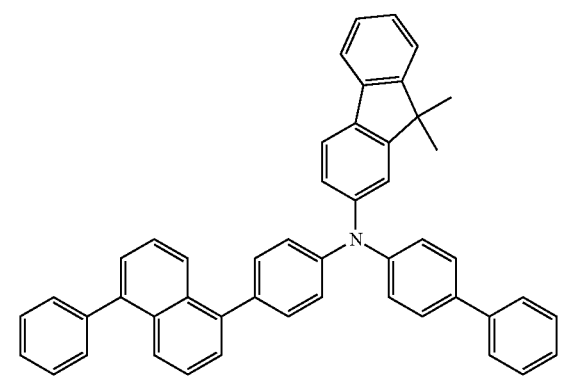
145
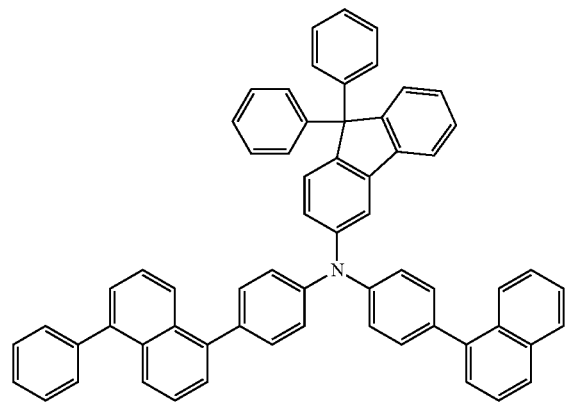
146
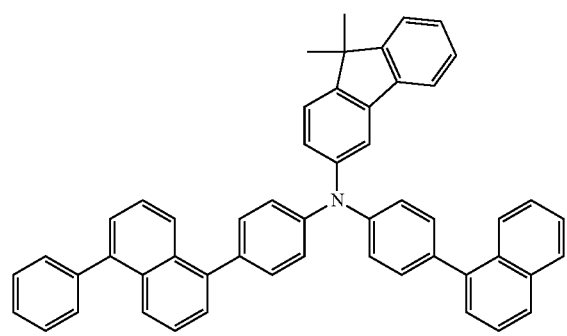
147
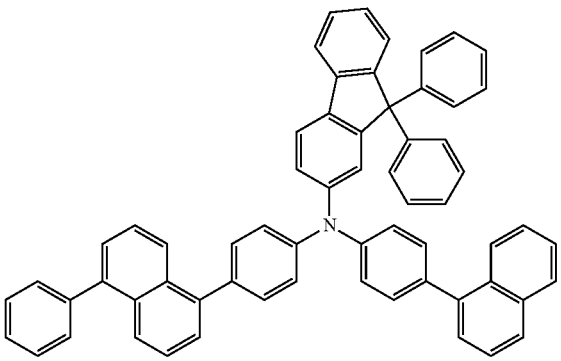
148
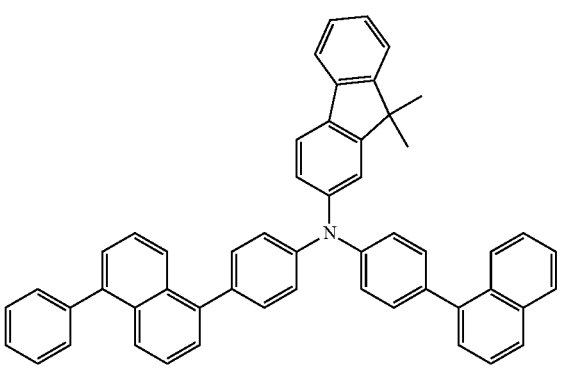
149
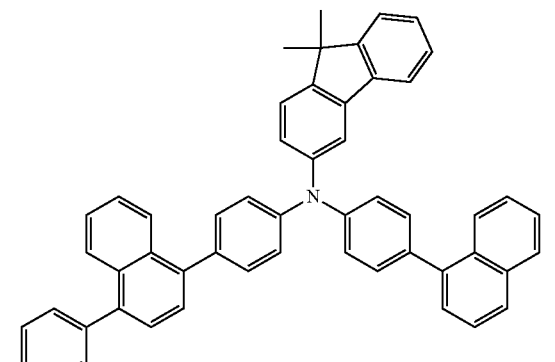
150
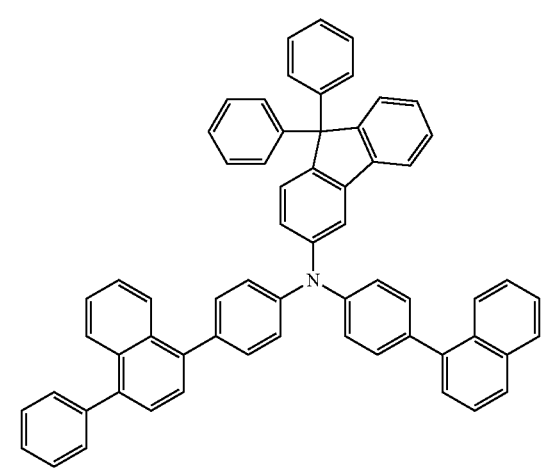

151
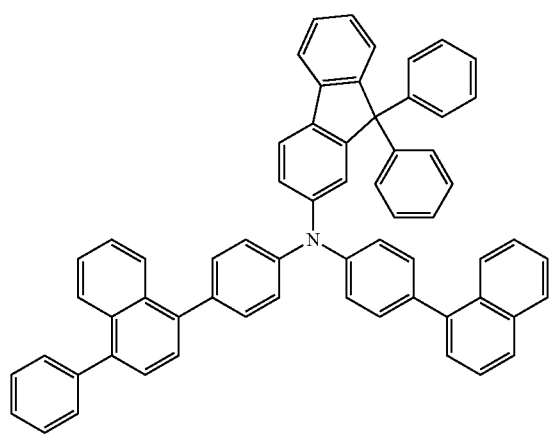
152
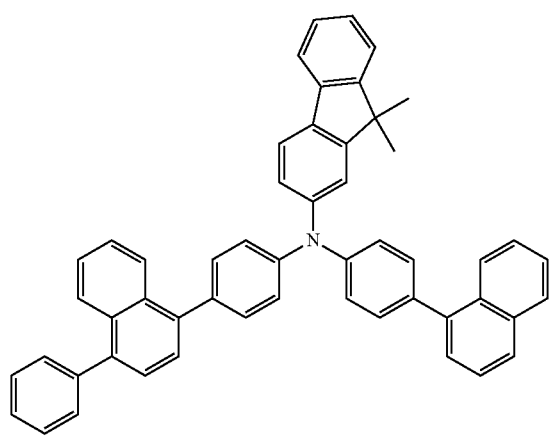
153
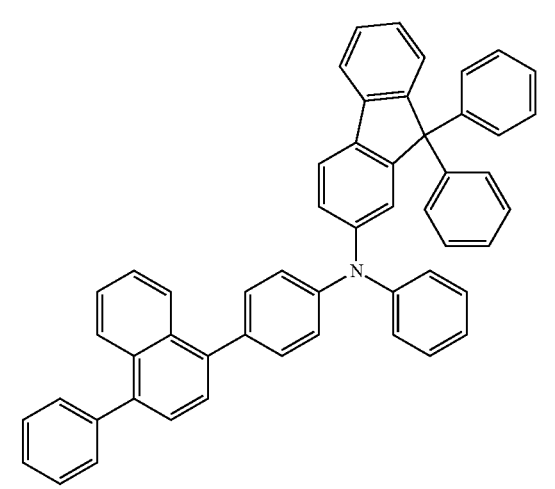
154
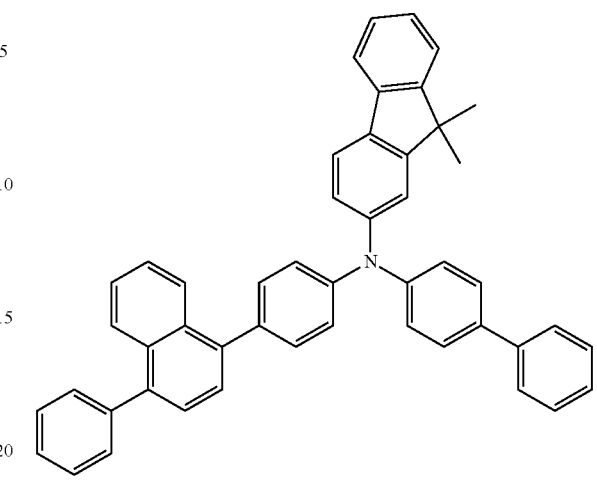
155
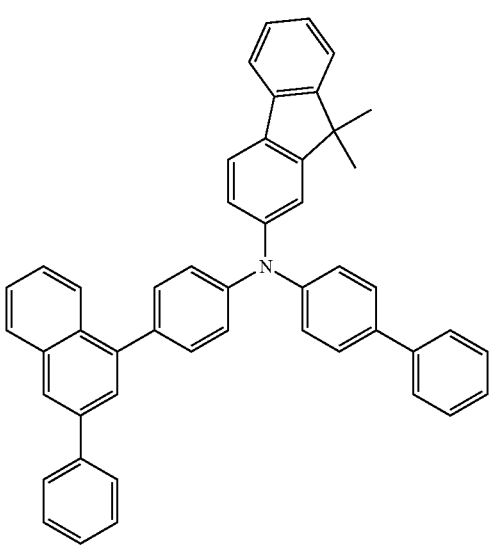
156

-continued
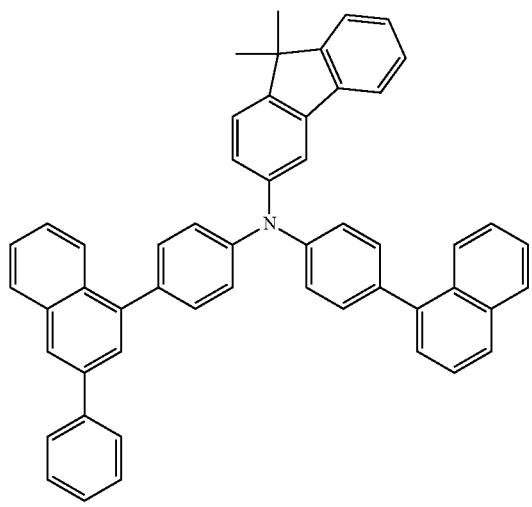
157
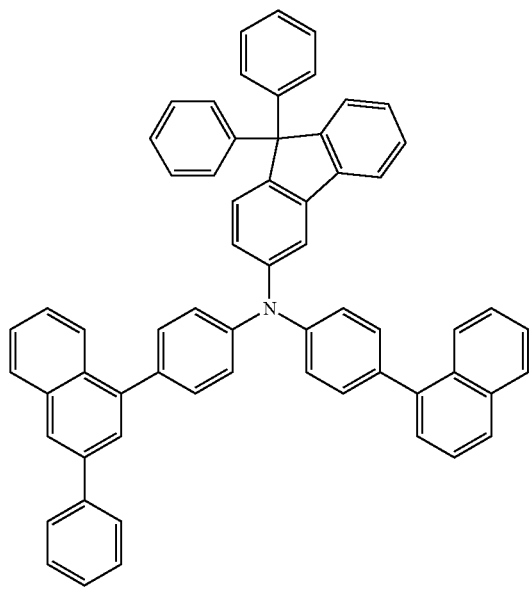
158
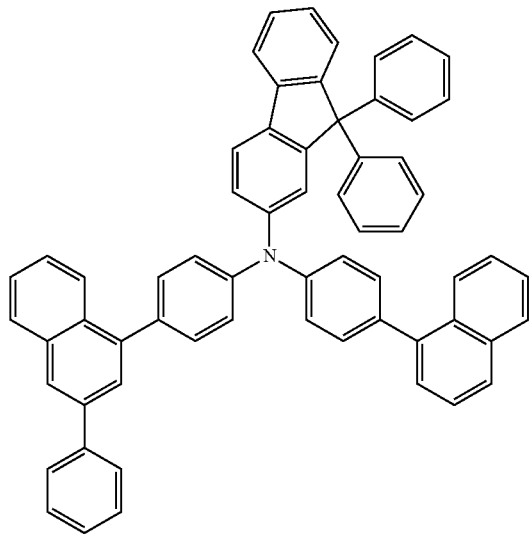
159
-continued
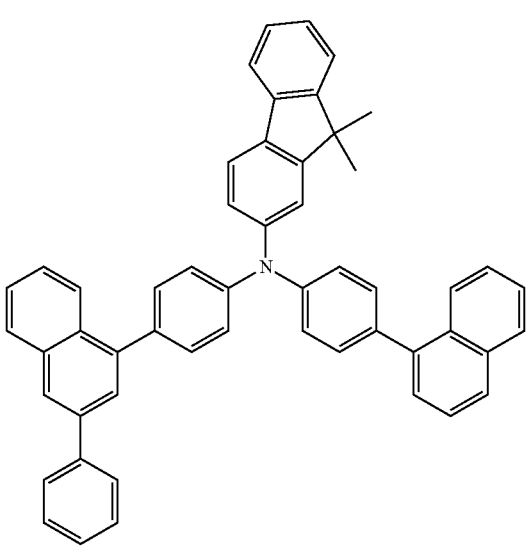
160
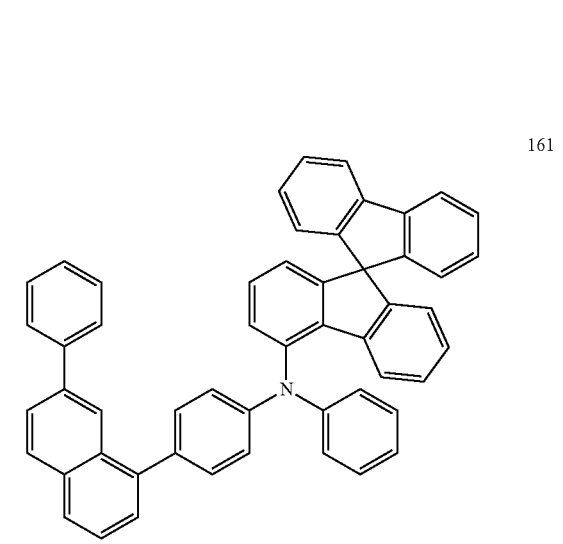
161
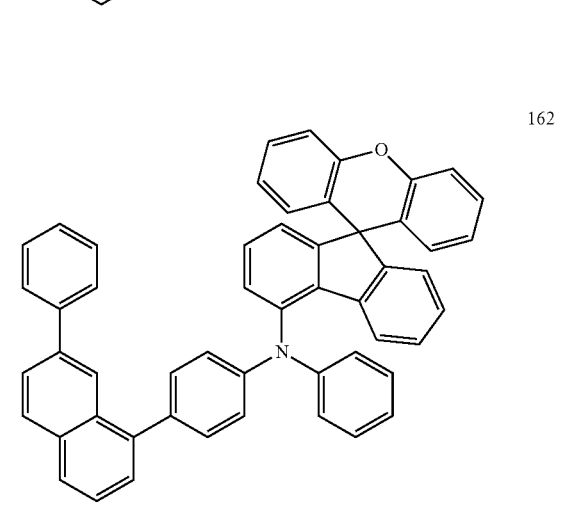
162

163
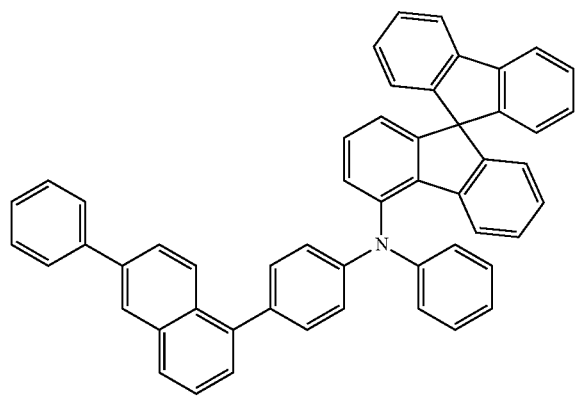
164
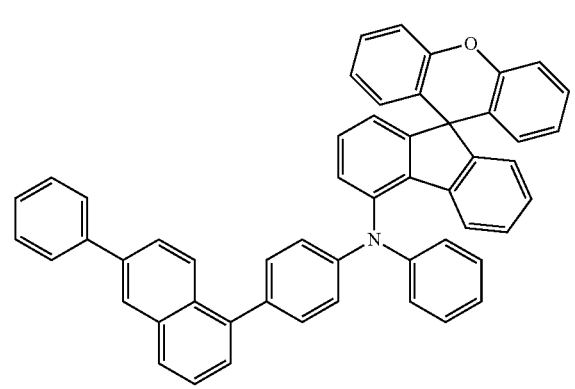
165
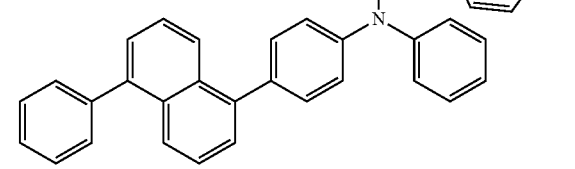
166
167
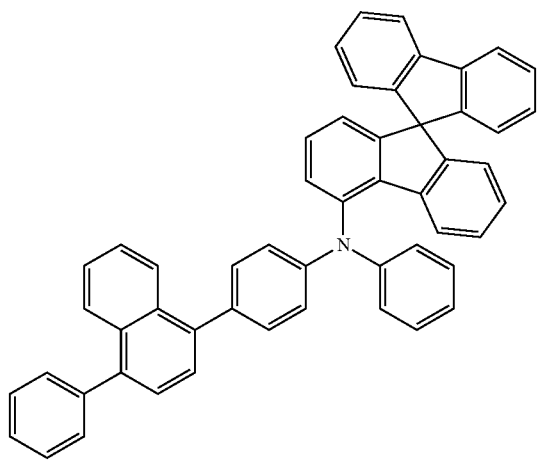
168
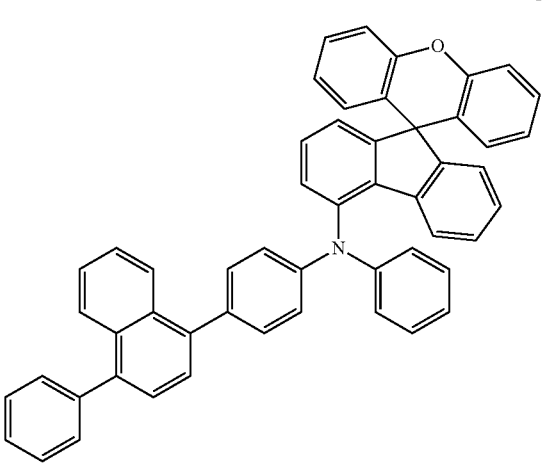
169
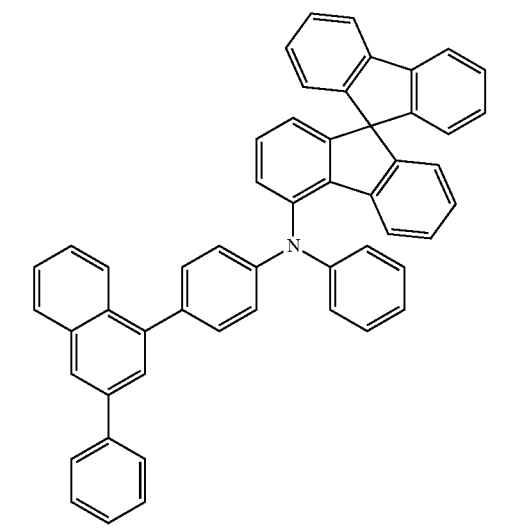

170
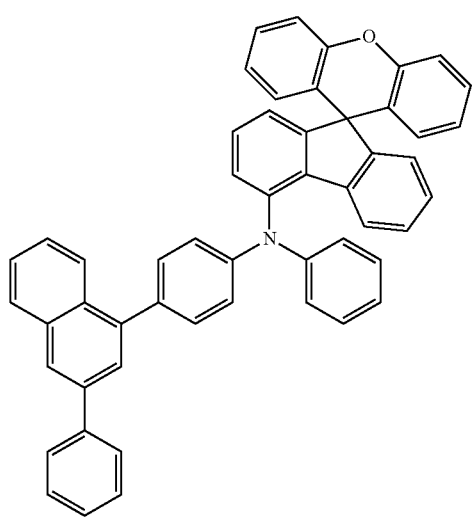
171
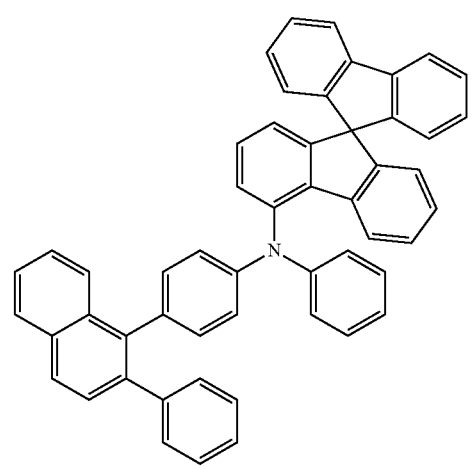
172
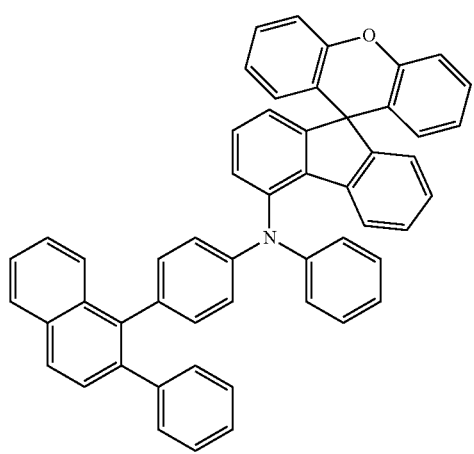
173
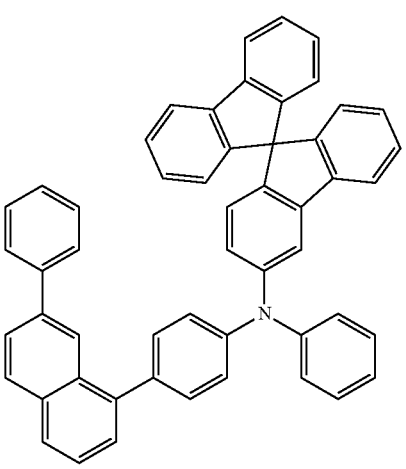
174
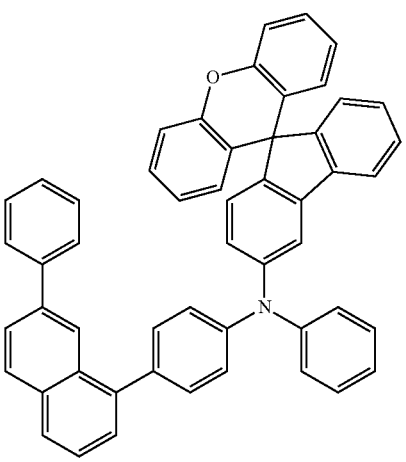
175
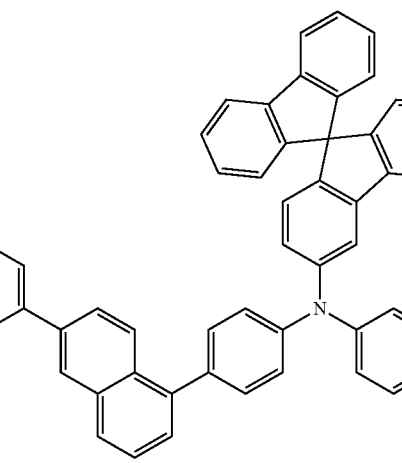

176
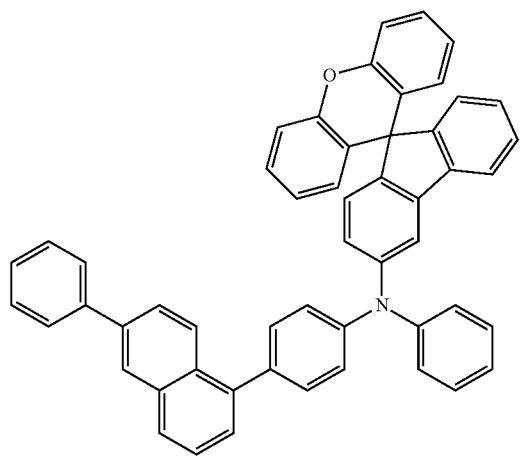
177
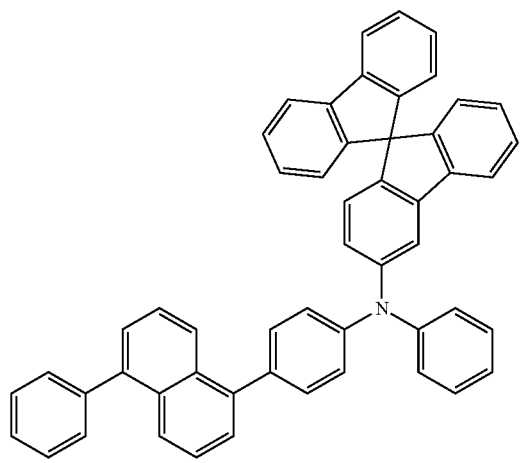
178
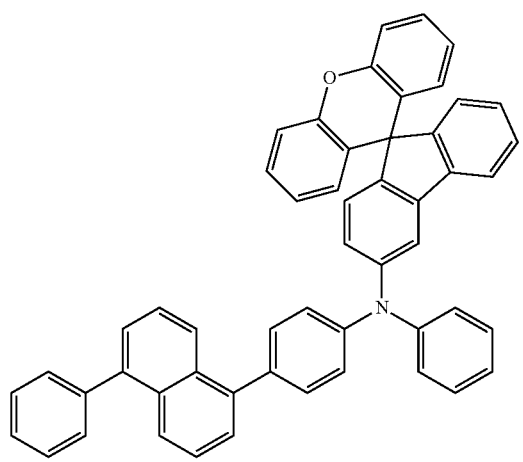
179
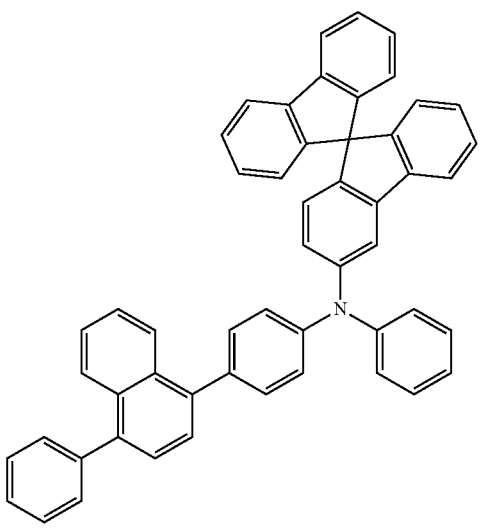
180
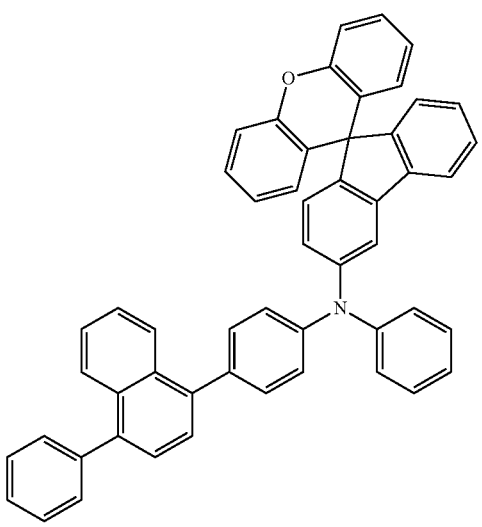

181
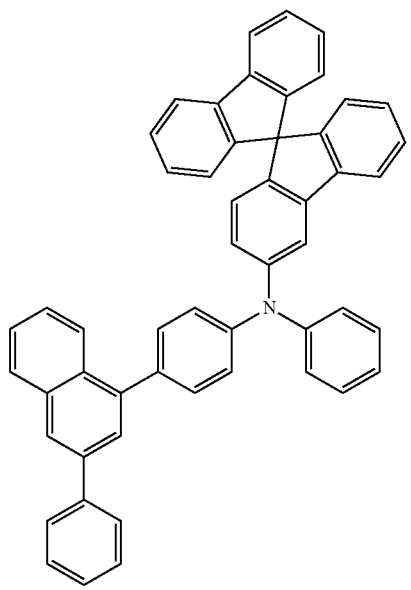
182
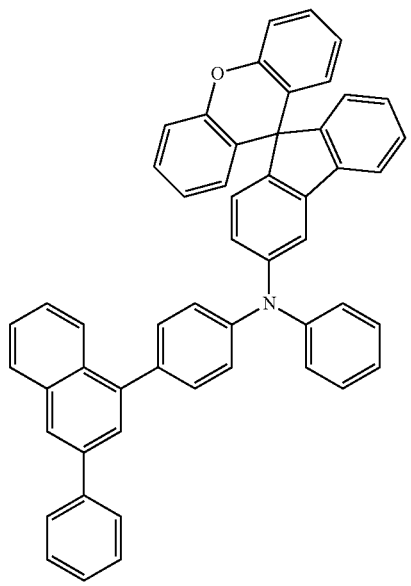
183
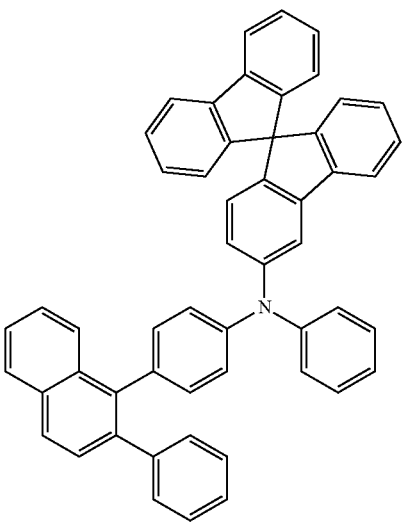
184
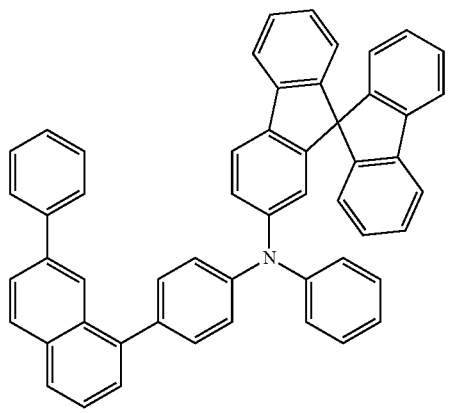
185

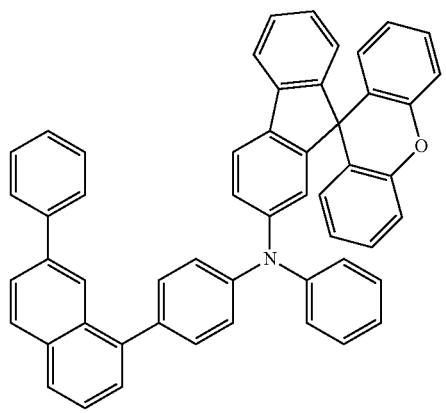
186
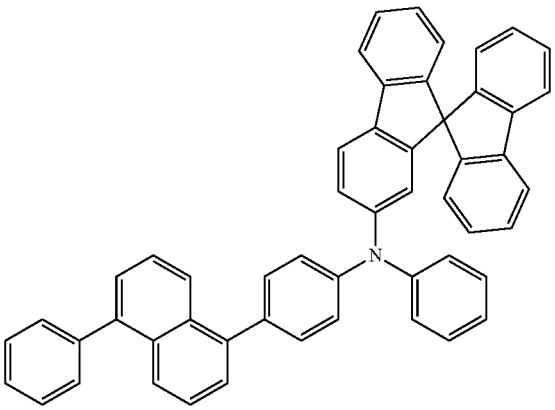
189
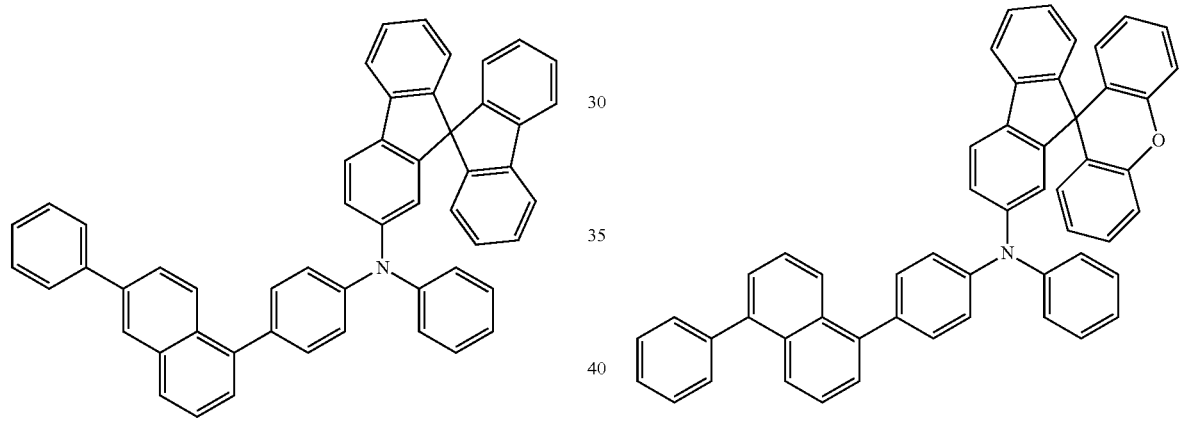
187
190
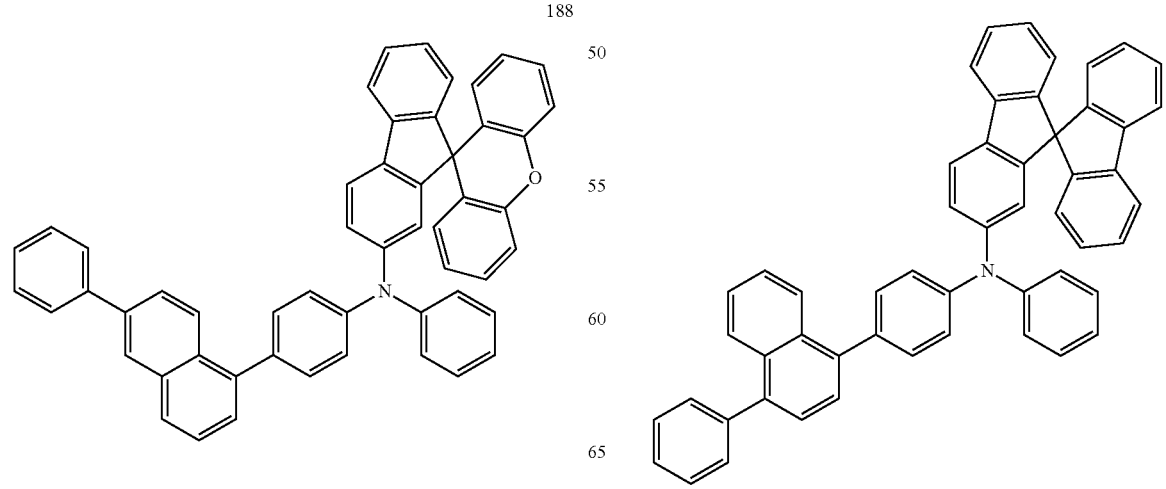
188
191

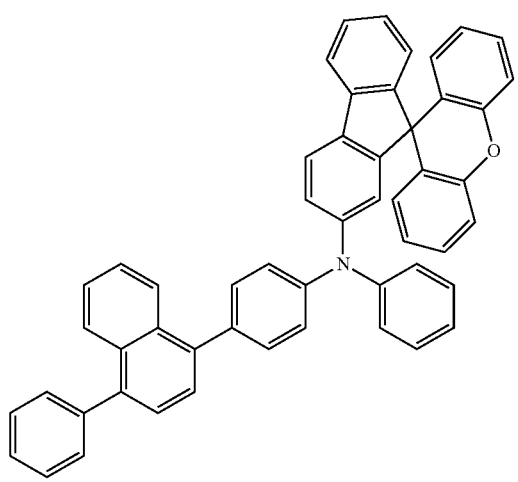
192
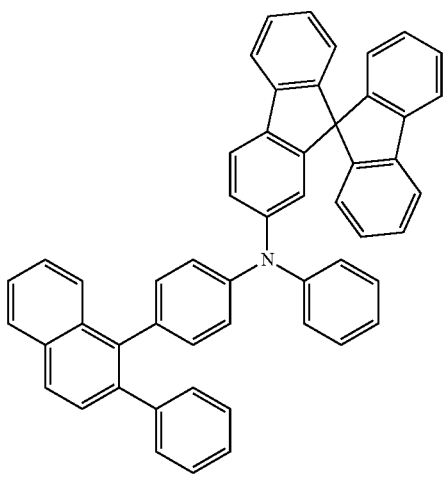
195
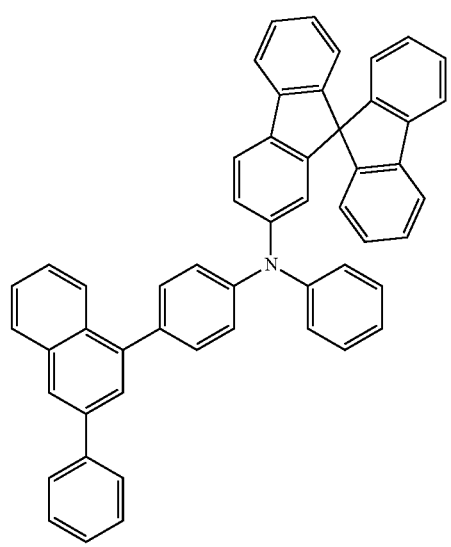
193
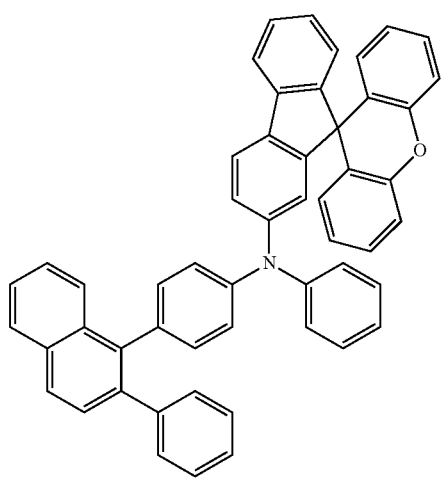
196
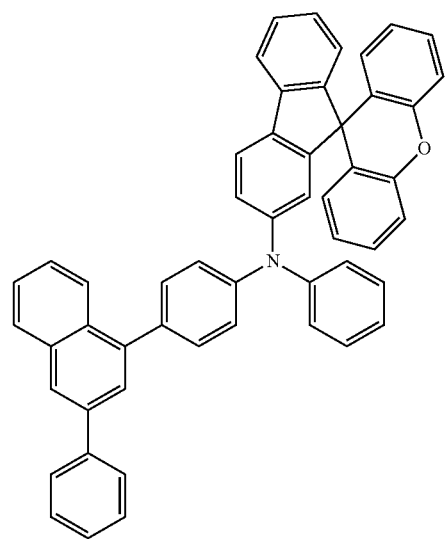
194
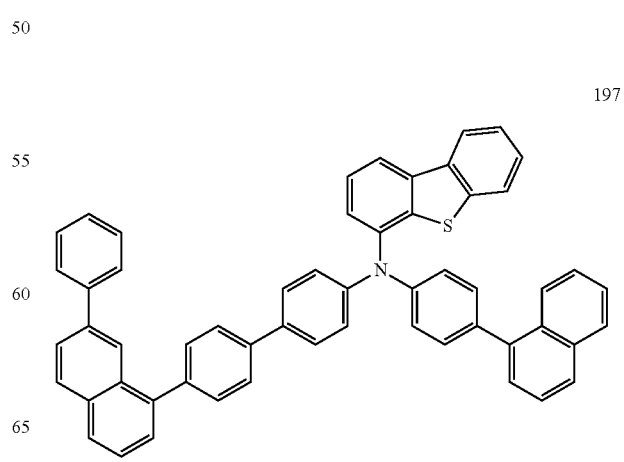
197

198
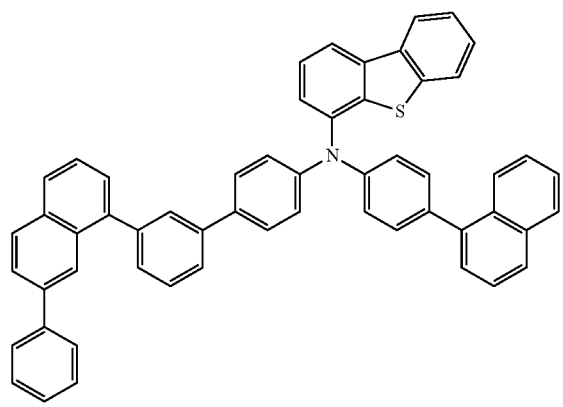
199
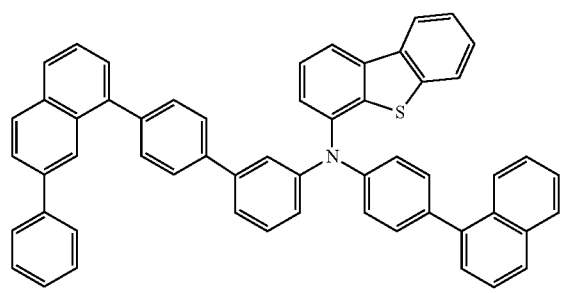
200
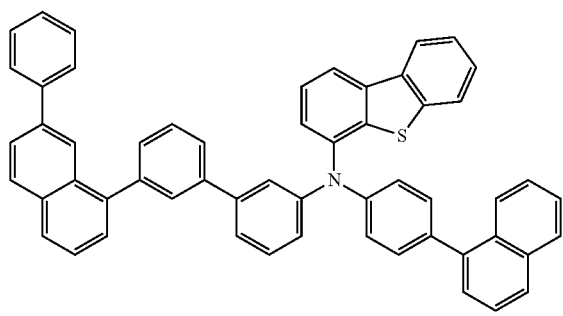
201
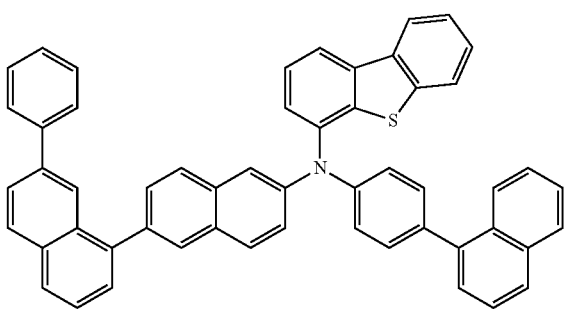
202
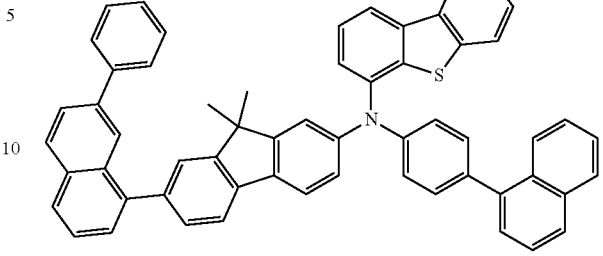
203
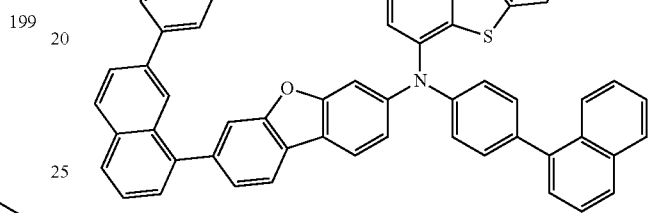
204
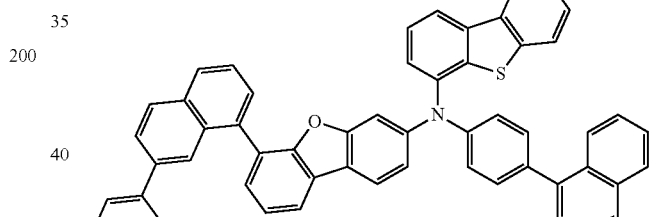
205
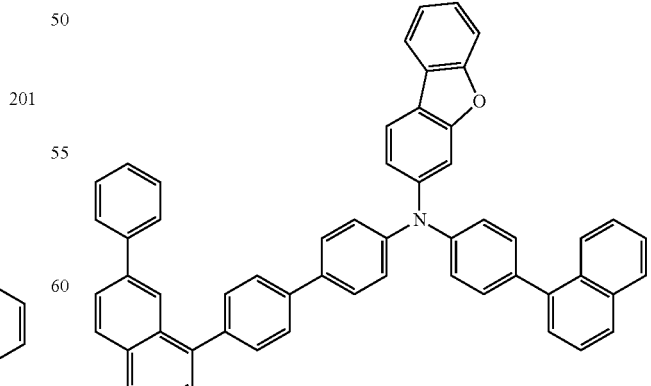

206

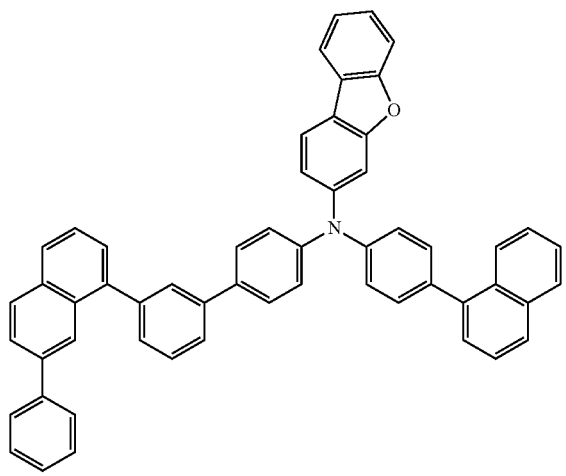

207

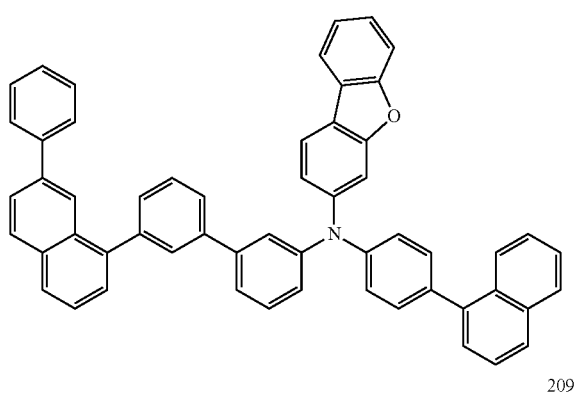

208

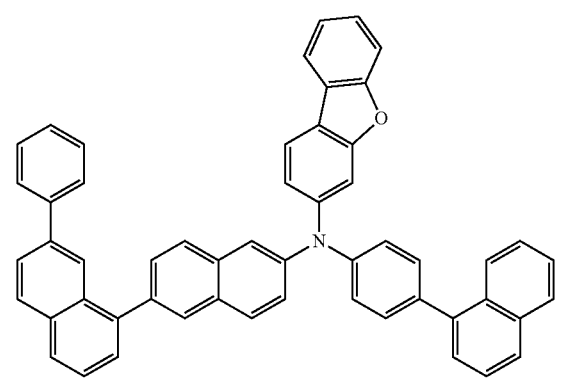

209

210

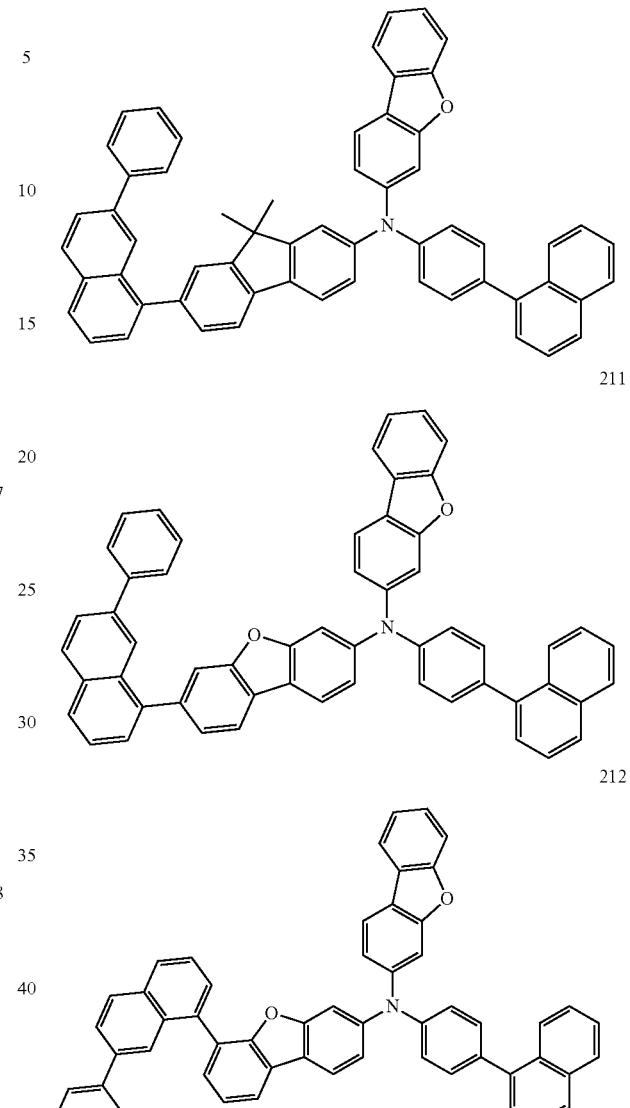

211

212

The monoamine compound according to an example embodiment includes a fused ring and a phenylnaphthyl group with a high thermal resistance and electric charge resistance, and therefore, when used as a material for an organic electroluminescence device it may contribute to extending a device life. When used as a material for an organic electroluminescence device, the monoamine compound may also enhance the quality of layers due to the bulky phenylnaphthyl group which decreases symmetry of molecule and inhibits crystallization, thereby contributing to securing high efficiency.

Hereinafter, an organic electroluminescence device according to an example embodiment will be explained, referring to FIGS. 1 to 3. The organic electroluminescence device according to an example embodiment includes the monoamine compound according to an example embodiment. For example, a hole transport region HTR includes the monoamine compound represented by Formula 1.

The following explanation will be mainly given with features different from the monoamine compound according to an example embodiment, and unexplained parts will follow the above description on the monoamine compound according to an example embodiment.

The first electrode EL1 has conductivity. The first electrode EL1 may be a pixel electrode or an anode. The first electrode EL1 may be a transmissive electrode, a transflective electrode, or a reflective electrode. In case the first electrode EL1 is the transmissive electrode, the first electrode EL1 may include a transparent metal oxide such as indium tin oxide (ITO), indium zinc oxide (IZO), zinc oxide (ZnO), or indium tin zinc oxide (ITZO). In case the first electrode EU is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed using the above materials, and a transparent conductive layer formed using ITO, IZO, ZnO, or ITZO. For example, the first electrode EL1 may have a triple-layer structure of ITO/Ag/ITO.

The thickness of the first electrode EL1 may be from about 1,000 Å to about 10,000 Å, for example, from about 1,000 Å to about 3,000 Å.

The hole transport region HTR is on the first electrode EL1. The hole transport region HTR may include at least one of a hole injection layer HIL, a hole transport layer HTL, a hole buffer layer, or an electron blocking layer EBL.

The hole transport region HTR includes the monoamine compound according to an example embodiment, as described above.

The hole transport region HTR may have a single layer formed using a single material, a single layer formed using a plurality of different materials, or a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In addition, the hole transport region HTR may have a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, laminated in order from the first electrode EL1, without limitation.

As described above, the hole transport region HTR may have a multilayer structure having a plurality of layers, and a layer of the plurality of layers contacting with the emission layer EML may include the monoamine compound represented by Formula 1. For example, the hole transport region HTR may include a hole injection layer HIL on the first electrode EL1, a hole transport layer HTL on the hole injection layer HIL, and an electron blocking layer EBL on the hole transport layer HTL, and the electron blocking layer EBL may include the monoamine compound represented by Formula 1. In another example, the hole transport region HTR may include a hole injection layer HIL and a hole transport layer HTL, and the hole transport layer HTL may include the monoamine compound represented by Formula 1.

The hole transport region HTR may include one or more of the monoamine compound represented by Formula 1. For example, the hole transport region HTR may include at least one selected from the group of compounds represented in the above-described Compound Group 1.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPD), triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL may include, for example, carbazole derivatives such as N-phenyl carbazole, polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl)triphenylamine (TCTA), N,N'-di(naphthalen-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The electron blocking layer EBL may include the monoamine compound represented by Formula 1, as described above. The electron blocking layer EBL may include a suitable material. The electron blocking layer EBL may include, for example, carbazole derivatives such as N-phenyl carbazole, polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl)triphenylamine (TCTA), N,N'-di(naphthalen-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD) or mCP, etc.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. In case the thicknesses of the hole transport region HTR, the hole injection layer HIL, the hole transport layer HTL and the electron blocking layer EBL satisfy the above-described ranges, satisfactory hole transport properties may be obtained without substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, for example, a p-dopant. The p-dopant may be one of quinone derivatives, metal oxides, or cyano group-containing compounds, without limitation.

For example, non-limiting examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide and molybdenum oxide, etc.

As described above, the hole transport region HTR may further include at least one of a hole buffer layer or an electron blocking layer EBL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer EBL is a layer preventing electron injection from the electron transport region ETR into the hole transport region HTR.

The emission layer EML is on the hole transport region HTR. The thickness of the emission layer EML may be, for example, from about 100 Å to about 1,000 Å, or from about 100 Å to about 600 Å. The emission layer EML may have a single layer formed using a single material, a single layer formed using a plurality of different materials, or a multi-layer structure having a plurality of layers formed using a plurality of different materials.

A suitable emission material may be used as a material for the emission layer EML. The material for the emission layer EML may be selected from, for example, fluoranthene derivatives, pyrene derivatives, arylacetylene derivatives, anthracene derivatives, fluorene derivatives, perylene derivatives, chrysene derivatives, or the like, and preferably, from pyrene derivatives, perylene derivatives, or anthracene derivatives. For example, as the host material of the emission layer EML, anthracene derivatives represented by the following Formula 3 may be used.

[Formula 3]

![Formula 3 structure with $(W_1)_{m1}$, $(W_2)_{m2}$, $(W_3)_{m3}$, $(W_4)_{m4}$ substituents on anthracene with two phenyl groups]

In Formula 3, $W_1$ to $W_4$ are each independently a hydrogen atom, a deuterium atom, a halogen atom, a substituted or unsubstituted silyl group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, or may form a ring by combining adjacent groups with each other, $m_1$ and $m_2$ are each independently an integer of 0 to 4, and $m_3$ and $m_4$ are each independently an integer of 0 to 5.

When m1 is 1, $W_1$ may not be a hydrogen atom. When $m_2$ is 1, $W_2$ may not be a hydrogen atom. When $m_3$ is 1, $W_3$ may not be a hydrogen atom. When $m_4$ is 1, $W_4$ may not be a hydrogen atom.

When m1 is an integer of 2 or more, a plurality of $W_1$ may be the same or different from each other. When $m_2$ is an integer of 2 or more, a plurality of $W_2$ may be the same or different from each other. When $m_3$ is an integer of 2 or more, a plurality of $W_3$ may be the same or different from each other. When $m_4$ is an integer of 2 or more, a plurality of $W_4$ may be the same or different from each other.

The compound represented by Formula 3 may include the compounds represented by the following structures, for example.

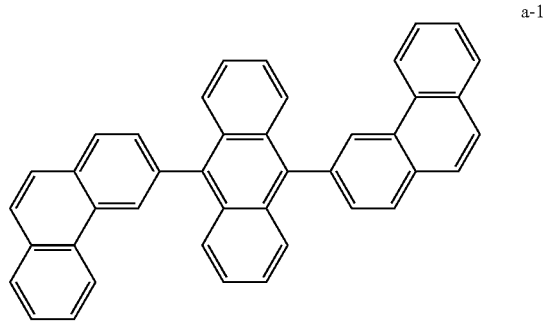

a-1

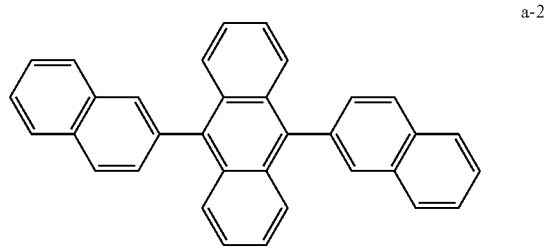

a-2

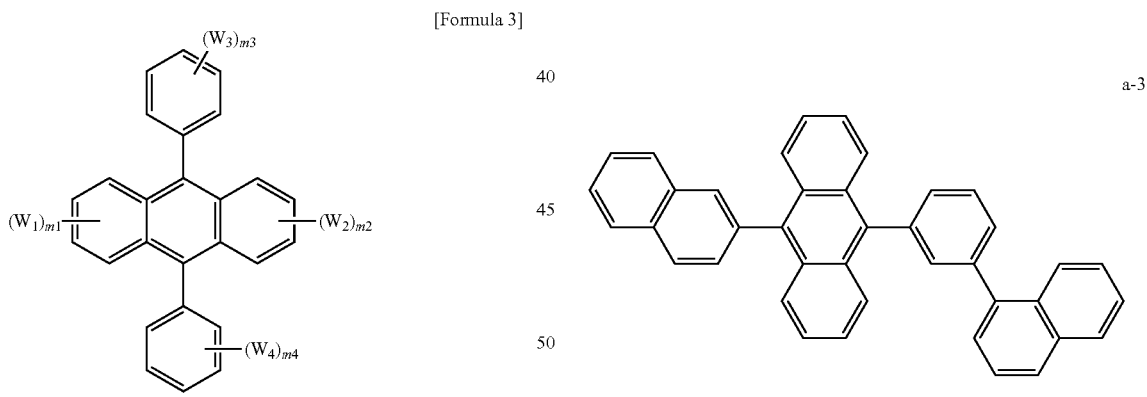

a-3 a-4 a-5 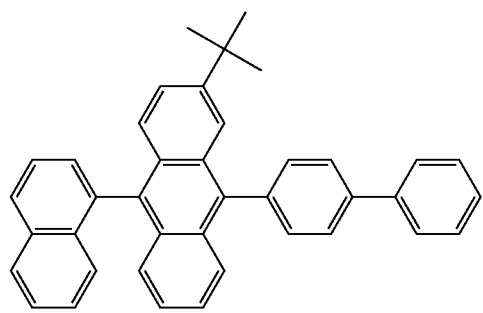

a-6 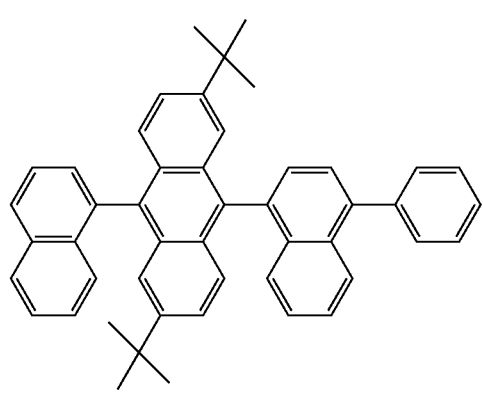

a-7 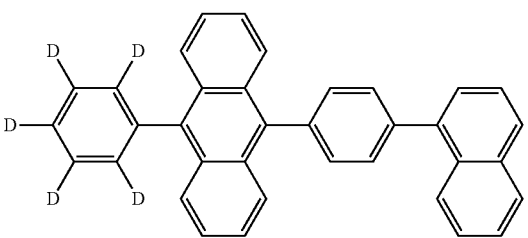

a-8 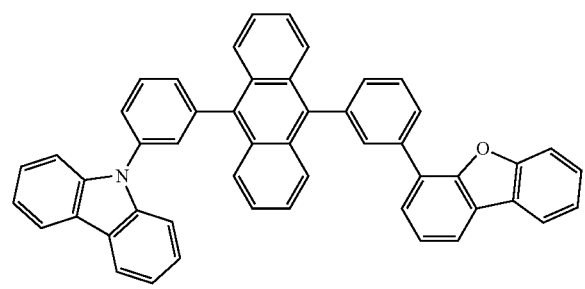

a-9 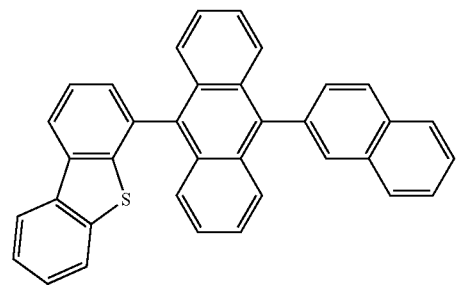

a-10 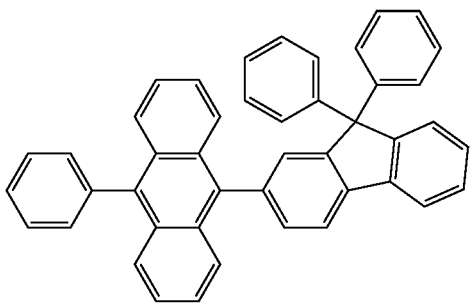

a-11 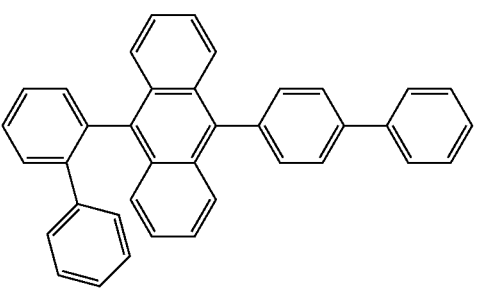

a-12 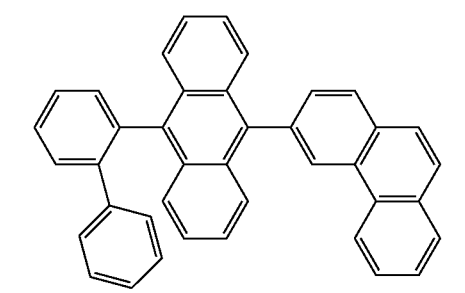

The emission layer EML may include a fluorescent material including any one selected from the group of spiro-DPVBi, 2,2',7,7'-tetrakis(biphenyl-4-yl)-9,9'-spirobifluorene (spiro-sexiphenyl) (spiro-6P), distyryl-benzene (DSB), distyryl-arylene (DSA), polyfluorene (PFO)-based polymer and poly(p-phenylene vinylene) (PPV)-based polymer, for example.

The emission layer EML may further include a dopant, and the dopant may be a suitable material. For example, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi)), perylene and the derivatives thereof (for example, 2,5,8,11-tetra-t-butylperylene (TBPe)), pyrene and the derivatives thereof (for example, 1,1-dipyrene, 1,4-dipyrenylbenzene, 1,4-bis(N,N-diphenylamino)pyrene, 1,6-bis(N,N-diphenylamino)pyrene), 2,5,8,11-tetra-t-butylperylene (TBP), 1,3,5-tris(N-phenylbenzimidazole-2-yl)benzene) (TPBi), etc., may be used as a dopant.

The emission layer EML may include, for example, tris(8-hydroxyquinolino)aluminum (Alq$_3$), 4,4'-bis(N-carbazolyl)-1,1'-biphenyl (CBP), poly(N-vinylcarbazole) (PVK), 9,10-di(naphthalen-2-yl)anthracene (ADN), 4,4',4"-tris(carbazol-9-yl)-triphenylamine (TCTA), 1,3,5-tris(N-phenylbenzimidazol-2-Abenzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), etc.

The electron transport region ETR is provided on the emission layer EML. The electron transport region ETR may include at least one of a hole blocking layer HBL, an electron transport layer ETL or an electron injection layer EIL, for example.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In addition, the electron transport region ETR may have a single layer structure having a plurality of different materials, or a laminated structure of electron transport layer ETL/electron injection layer EIL, or hole blocking layer HBL/electron transport layer ETL/electron injection layer EIL, laminated in order from the emission layer EML, without limitation. The thickness of the electron transport region ETR may be, for example, from about 100 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In case the electron transport region ETR includes the electron transport layer ETL, the electron transport region ETR may include tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl] ether oxide (DPEPO), 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1, O8)-(1,1'-Biphenyl-4-olato) aluminum (BAlq), beryllium bis(benzoquinolin-10-olate) ($Bebq_2$), 9,10-di(naphthalen-2-yl)anthracene (ADN), or a mixture thereof, for example. The thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without substantial increase of a driving voltage.

When the electron transport region ETR includes the electron injection layer EIL, the electron transport region ETR may use LiF, lithium quinolate (LIQ), $Li_2O$, BaO, NaCl, CsF, a metal in lanthanides such as Yb, or a metal halide such as RbCl and RbI, for example. The electron injection layer EIL also may be formed using a mixture material of an electron transport material and an insulating organo metal salt. The organo metal salt may be a material having an energy band gap of about 4 eV or more. The organo metal salt may include, for example, a metal acetate, a metal benzoate, a metal acetoacetate, a metal acetylacetonate, or a metal stearate. The thickness of the electron injection layer EIL may be from about 1 Å to about 100 Å, for example, from about 3 Å to about 90 Å. In case the thickness of the electron injection layer EIL satisfies the above described range, satisfactory electron injection properties may be obtained without inducing the substantial increase of a driving voltage.

The electron transport region ETR may include a hole blocking layer HBL, as described above. The hole blocking layer HBL may include, for example, 2,9-dimethyl-4,7-diphenyl-1,10-phenanthroline (BCP), 4,7-diphenyl-1,10-phenanthroline (Bphen), or bis[2-(diphenylphosphino)phenyl]ether oxide (DPEPO), etc.

The second electrode EL2 is on the electron transport region ETR. The second electrode EL2 may be a common electrode or a cathode. The second electrode EL2 may be a transmissive electrode, a transflective electrode or a reflective electrode. In case the second electrode EL2 is the transmissive electrode, the second electrode EL2 may be formed using transparent metal oxides, for example, ITO, IZO, ZnO, ITZO, etc.

In case the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayer structure including a reflective layer or a transflective layer formed using the above-described materials and a transparent conductive layer formed using ITO, IZO, ZnO, ITZO, etc.

The second electrode EL2 may be connected with an auxiliary electrode. In case the second electrode EL2 is connected with the auxiliary electrode, the resistance of the second electrode EL2 may decrease.

In the organic electroluminescence device 10, according to the application of a voltage to each of the first electrode EL1 and the second electrode EL2, holes injected from the first electrode EU may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

In case the organic electroluminescence device 10 is a top emission type, the first electrode EL1 may be a reflective electrode, and the second electrode EL2 may be a transmissive electrode or a transflective electrode. In case the organic electroluminescence device 10 is a bottom emission type, the first electrode EL1 may be a transmissive electrode or a transflective electrode, and the second electrode EL2 may be a reflective electrode.

The organic electroluminescence device 10 according to an example embodiment includes the monoamine compound represented by Formula 1, thereby securing high efficiency and a long device life, as well as a decreased driving voltage.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS EXAMPLES

The monoamine compound according to an example embodiment may be synthesized, for example, as follows.

1. Synthesis of Compound 1

Compound 1, a monoamine compound according to an example embodiment, may be synthesized, for example, as follows.

(Synthesis of Intermediate A)

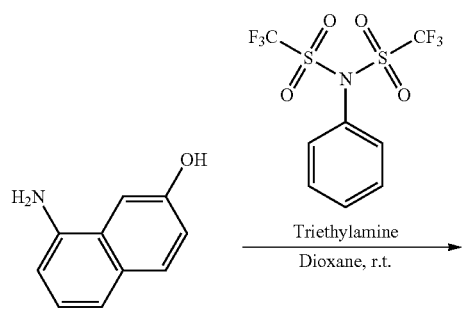

Under an argon (Ar) atmosphere, N-phenyltrifluoromethane sulfonamide (25.1 g) dissolved in dioxane (80 mL) was added dropwisely to a solution of 8-amino-2-naphthol (10.0 g) and triethylamine (12 mL) dissolved in dioxane (200 mL) in an 1 L three-neck flask, at about 0° C. for about 30 minutes, and the mixture was heated and stirred at room temperature for about 4 hours. Hexane was added to the reaction solution, and the precipitated solid was filtered by using a suction system to obtain 15.9 g (yield 87%) of Intermediate A as a brown solid.

The molecular weight of Intermediate A measured by FAB-MS was 291.

(Synthesis of Intermediate B)

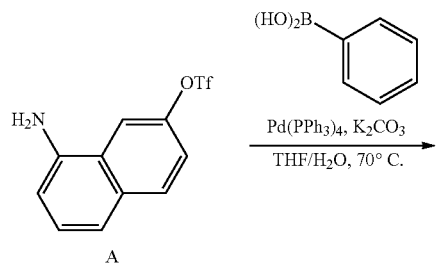

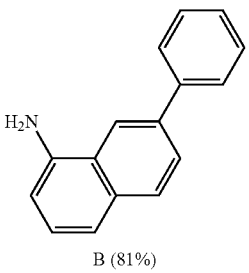

Under an argon (Ar) atmosphere, Intermediate A (3.00 g), Pd(PPh$_3$)$_4$ (0.361 g), K$_2$CO$_3$ (2.85 g), and phenylboronic acid (1.67 g) were dissolved in a mixture solution of THF/water (8:2) (110 mL) in a 300 mL three neck flask, and the resultant was heated and stirred at about 70° C. for about 5 hours. After cooling in air, dichloromethane was added, an organic layer was separated and taken, and solvents were evaporated. The crude product thus obtained was purified by silica gel column chromatography (hexane/toluene) to obtain 1.83 g (yield 81%) of Intermediate B as a pale yellow solid.

The molecular weight of Intermediate B measured by FAB-MS was 219.

(Synthesis of Intermediate C)

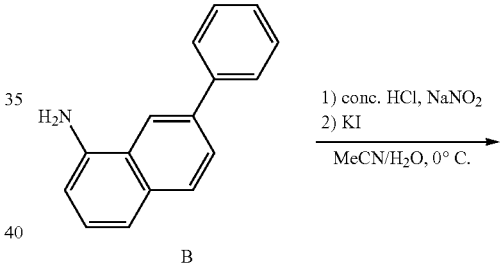

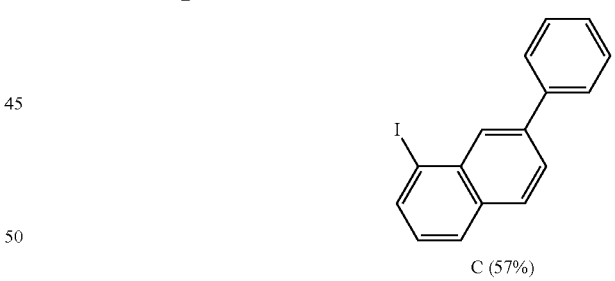

Under an atmospheric condition, Intermediate B (1.50 g), conc. HCl (5.20 mL), and NaNO$_2$ (0.78 g) were dissolved in a mixture solution of MeCN/water (1:1) (13 mL) in an 100 mL three neck flask, and the resultant was stirred at about 0° C. for about 15 minutes. After that, KI (9.38 g) dissolved in water (26 mL) was added slowly, followed by stirring at about 0° C. for about 2 hours. After that, dichloromethane was added, an organic layer was separated and taken, and solvents were evaporated. The crude product thus obtained was purified by silica gel column chromatography (hexane) to obtain 1.73 g (yield 57%) of Intermediate C as brown oil.

The molecular weight of Intermediate C measured by GC-MS was 330.

(Synthesis of Intermediate D)

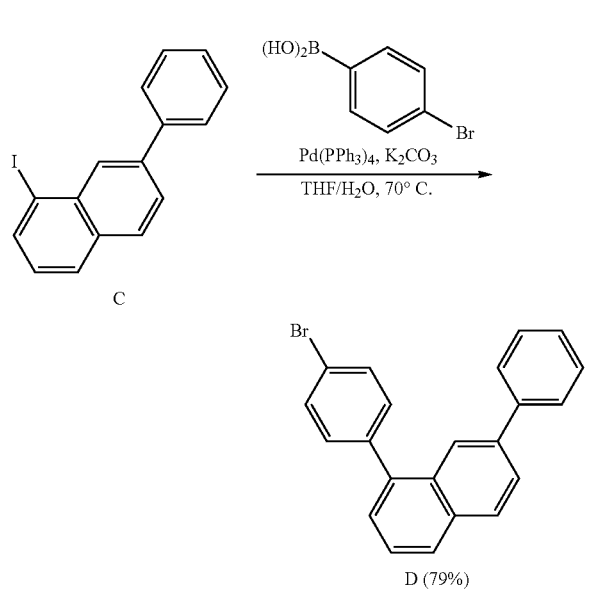

Under an argon (Ar) atmosphere, Intermediate C (2.86 g), Pd(PPh₃)₄ (0.30 g), K₂CO₃ (2.39 g), and 4-bromophenylboronic acid (1.74 g) were dissolved in a mixture solution of THF/water (8:2) (90 mL) in a 300 mL three neck flask, and the resultant was heated and stirred at about 70° C. for about 5 hours. After cooling in air, dichloromethane was added, an organic layer was separated and taken, and solvents were evaporated. The crude product thus obtained was purified by silica gel column chromatography (hexane/toluene) to obtain 2.46 g (yield 79%) of Intermediate D as a white solid.

The molecular weight of Intermediate D measured by GC-MS was 358.

(Synthesis of Compound 1)

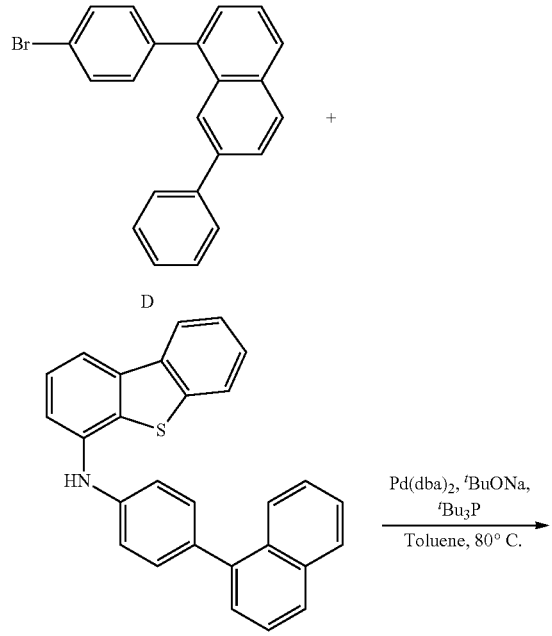

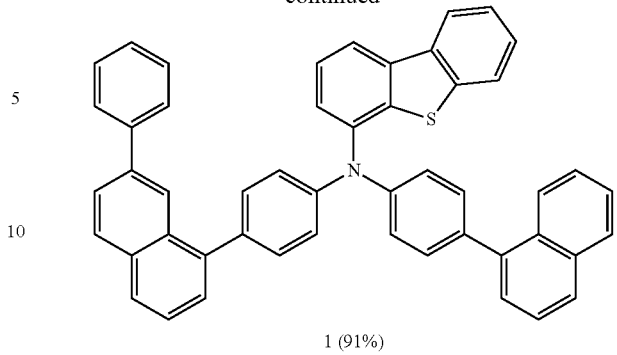

Under an argon (Ar) atmosphere, N-[4-(1-naphthalenyl) phenyl]-4-dibenzothiophenamine (2.80 g), Intermediate D (2.51 g), Pd(dba)₂ (0.14 g), tBu₃P (0.11 g) and tBuONa (1.34 g) were dissolved in dehydrated toluene (93 mL) in a 200 mL three neck flask, and the resultant was heated and stirred at about 80° C. for about 5 hours. After cooling in air, dichloromethane was added, an organic layer was separated and taken, and solvents were evaporated. The crude product thus obtained was purified by silica gel column chromatography (hexane) to obtain 4.31 g (yield 91%) of Compound 1 as a white solid.

The molecular weight of Compound 1 measured by FAB-MS was 679.

[¹H NMR (CDCl₃, 25° C., 300 Hz) δ=8.92-8.36 (m, 12H), 8.33 (d, J=8.5 Hz, 2H), 7.96 (d, J=8.5 Hz, 2H), 7.86-7.70 (m, 6H), 7.55 (d, J=8.5 Hz, 4H), 7.51-7.32 (m, 4H), 7.27-7.14 (m, 3H)]

2. Synthesis of Compound 17

Compound 17, a monoamine compound according to an example embodiment, may be synthesized, for example, as follows.

(Synthesis of Intermediate E)

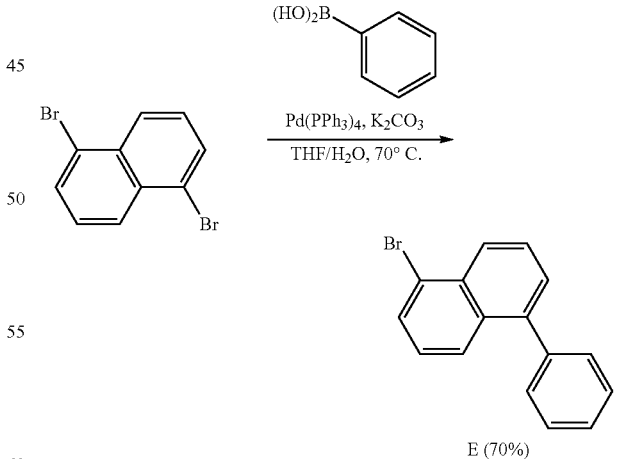

Under an argon (Ar) atmosphere, 1,5-dibromonaphthalene (18.7 g), phenylboronic acid (2.86 g), Pd(PPh₃)₄ (0.813 g), and K₂CO₃ (5.15 g) were dissolved in a mixture solution of THF/water (8:2) (360 mL) in an 1 L three neck flask, and the resultant was heated and stirred at about 70° C. for about 5 hours. After cooling in air, dichloromethane was added, an organic layer was separated and taken, and solvents were evaporated. The crude product thus obtained was purified by silica gel column chromatography (hexane) to obtain 4.65 g (yield 70%) of Intermediate E as a pale yellow solid.

The molecular weight of Intermediate E measured by GC-MS was 282.

(Synthesis of Intermediate F)

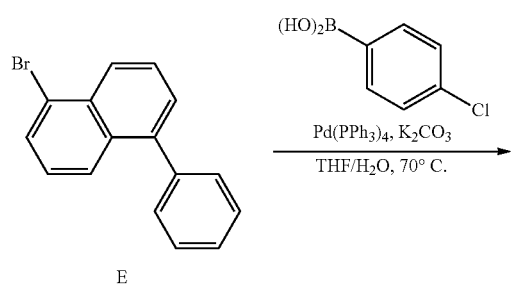

E

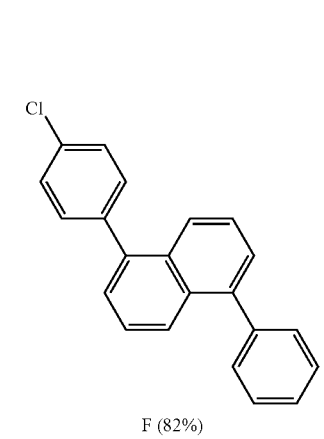

F (82%)

Under an argon (Ar) atmosphere, Intermediate E (2.02 g), 4-chlorophenylboronic acid (1.12 g), Pd(PPh$_3$)$_4$ (0.213 g), and K$_2$CO$_3$ (1.98 g) were dissolved in a mixture solution of THF/water (8:2) (110 mL) in an 1 L three neck flask, and the resultant was heated and stirred at about 70° C. for about 7 hours. After cooling in air, dichloromethane was added, an organic layer was separated and taken, and solvents were evaporated. The crude product thus obtained was purified by silica gel column chromatography (hexane/AcOEt) to obtain 2.25 g (yield 82%) of Intermediate F as a pale yellow solid.

The molecular weight of Intermediate F measured by GC-MS was 314.

(Synthesis of Compound 17)

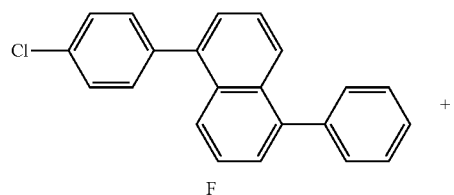

F

+

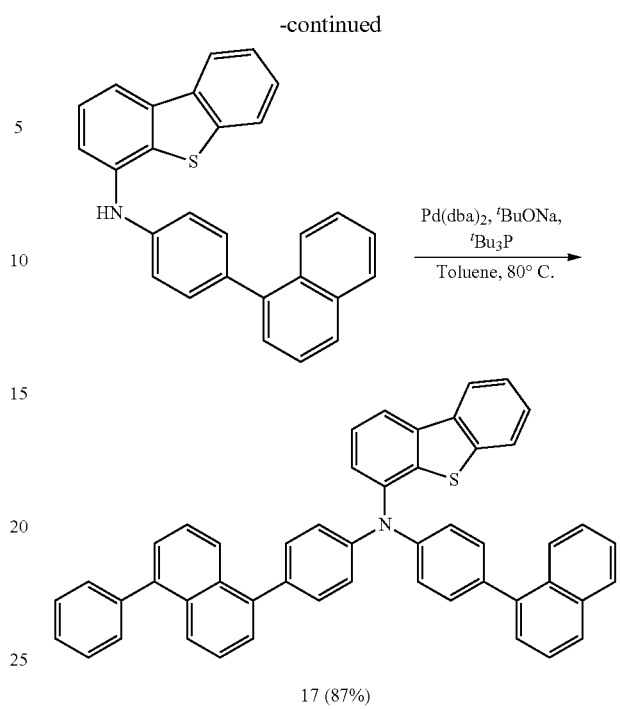

17 (87%)

Under an argon (Ar) atmosphere, N-[4-(1-naphthalenyl) phenyl]-4-dibenzothiophenamine (3.19 g), Intermediate F (2.50 g), Pd(dba)$_2$ (0.14 g), tBu$_3$P (0.14 g) and tBuONa (1.54 g) were dissolved in dehydrated toluene (53 mL) in a 200 mL three neck flask, and the resultant was heated and stirred at about 80° C. for about 8 hours. After cooling in air, dichloromethane was added, an organic layer was separated and taken, and solvents were evaporated. The crude product thus obtained was purified by silica gel column chromatography (hexane/AcOEt) to obtain 4.70 g (yield 87%) of Compound 17 as a white solid.

The molecular weight of Compound 1 measured by FAB-MS was 679.

[$^1$H NMR (CDCl$_3$, 25° C., 300 Hz) δ=9.00 (d, J=7.5 Hz, 2H), 8.82-8.41 (m, 12H), 7.96 (d, J=8.2 Hz, 2H), 7.86-7.71 (m, 6H), 7.55 (d, J=8.8 Hz, 4H), 7.51-7.30 (m, 3H), 7.26-7.14 (m, 4H)]

3. Synthesis of Compound 71

Compound 71, a monoamine compound according to an example embodiment, may be synthesized, for example, as follows.

(Synthesis of Intermediate G)

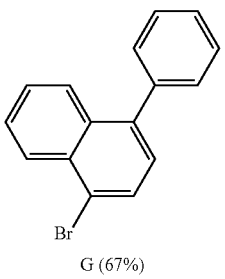

G (67%)

Intermediate G was synthesized by conducting the same synthetic method of Intermediate E except for using 1,4-dibromonaphthalene instead of 1,5-dibromonaphthalene in the synthetic method of Intermediate E.

The molecular weight of Intermediate G measured by FAB-MS was 283.

(Synthesis of Intermediate H)

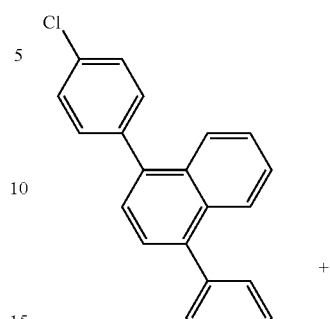

H (76%)

Intermediate H was synthesized by conducting the same synthetic method of Intermediate F except for using Intermediate G instead of Intermediate E in the synthetic method of Intermediate F.

The molecular weight of Intermediate H measured by GC-MS was 314.

(Synthesis of Compound 71)

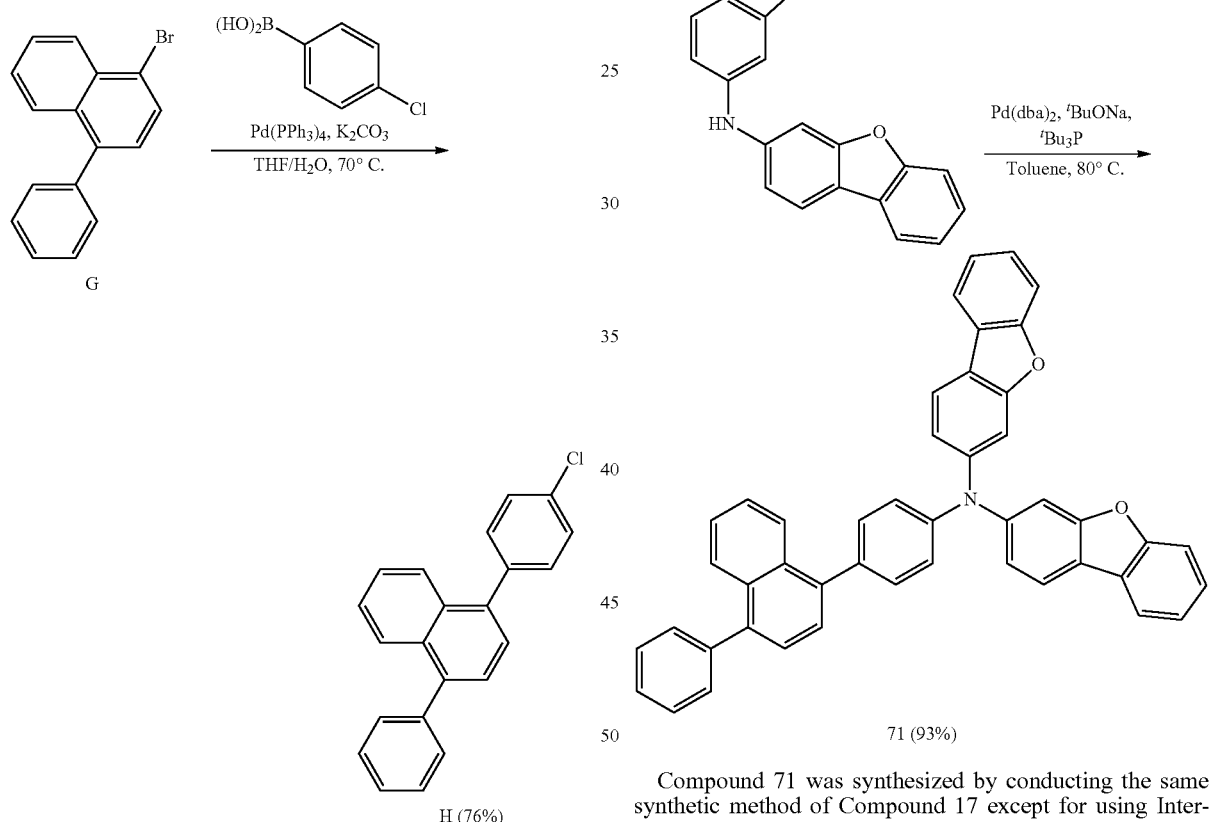

71 (93%)

Compound 71 was synthesized by conducting the same synthetic method of Compound 17 except for using Intermediate H instead of Intermediate F and using N-3-dibenzofuranyl-3-dibenzofuranamine instead of N-[4-(1-naphthalenyl)phenyl]-4-dibenzothiophenamine in the synthetic method of Compound 17.

The molecular weight of Compound 71 measured by FAB-MS was 627.

[$^{1}$H NMR (CDCl$_{3}$, 25° C., 300 Hz) δ=8.22 (d, J=8.5 Hz, 2H), 8.01-7.88 (m, 12H), 7.86 (d, J=8.2 Hz, 2H), 7.77-7.73 (m, 6H), 7.51-7.30 (m, 3H), 7.16-7.07 (m, 4H)]

4. Synthesis of Compound 94

Compound 94, a monoamine compound according to an example embodiment, may be synthesized, for example, as follows.

(Synthesis of Intermediate L)

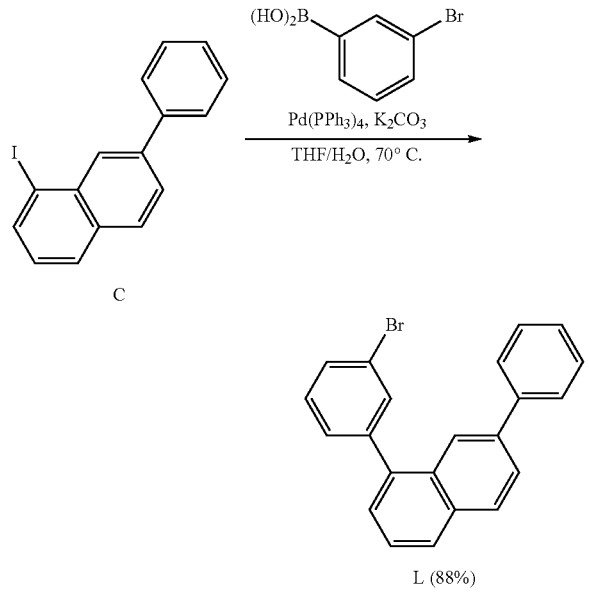

Intermediate L was synthesized by conducting the same synthetic method of Intermediate D except for using 3-bromophenylboronic acid instead of 4-bromophenylboronic acid in the synthetic method of Intermediate D.

The molecular weight of Intermediate L measured by GC-MS was 358.

(Synthesis of Compound 94)

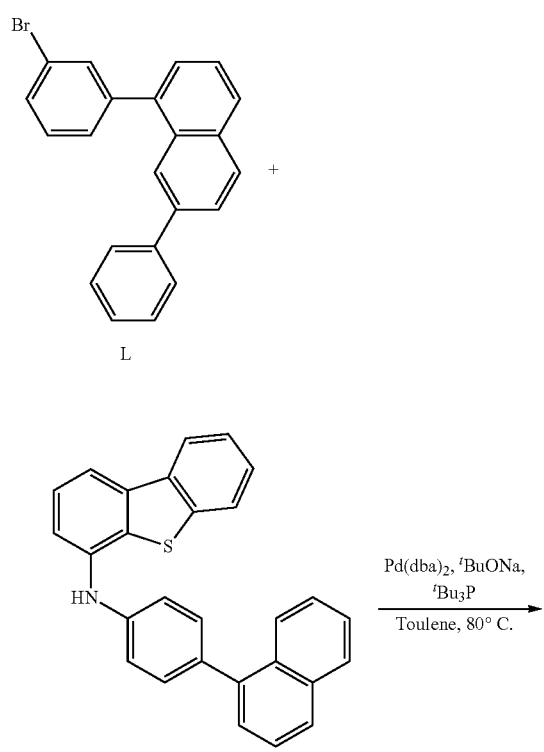

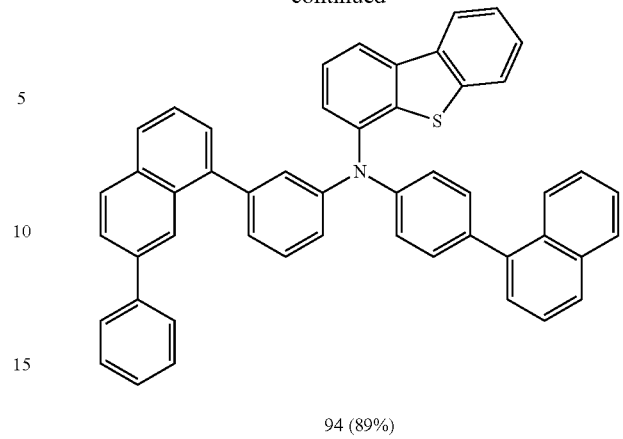

94 (89%)

Compound 94 was synthesized by conducting the same synthetic method of Compound 17 except for using intermediate L instead of Intermediate F in the synthetic method of Compound 17.

The molecular weight of Compound 94 measured by FAB-MS was 679.

[$^1$H NMR (CDCl$_3$, 25° C., 300 Hz) δ=8.77-8.36 (m, 12H), 8.33 (d, J=8.5 Hz, 2H), 8.00 (d, J=8.3 Hz, 2H), 7.85-7.70 (m, 6H); 7.58 (d, J=8.5 Hz, 4H), 7.51-7.42 (m, 4H), 7.34-7.24 (m, 3H)]

5. Synthesis of Compound 80

Compound 80, a monoamine compound according to an example embodiment, may be synthesized, for example, as follows.

(Synthesis of Intermediate N)

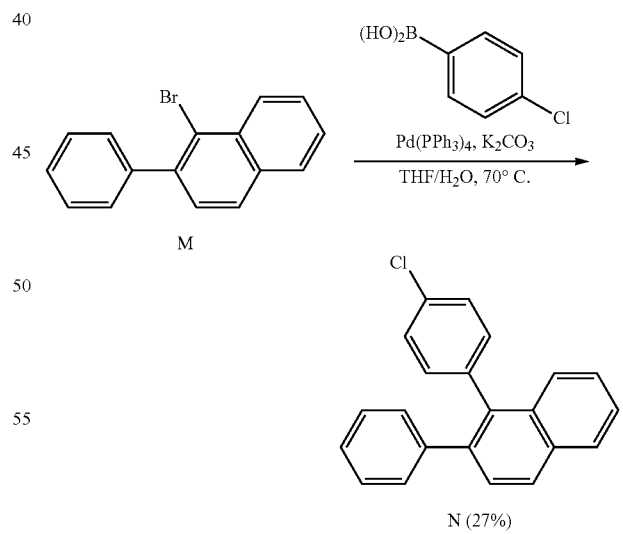

Intermediate N was synthesized by conducting the same synthetic method of Intermediate F except for using Intermediate M instead of Intermediate E in the synthetic method of Intermediate F.

The molecular weight of Intermediate N measured by GC-MS was 314.

87
(Synthesis of Compound 80)

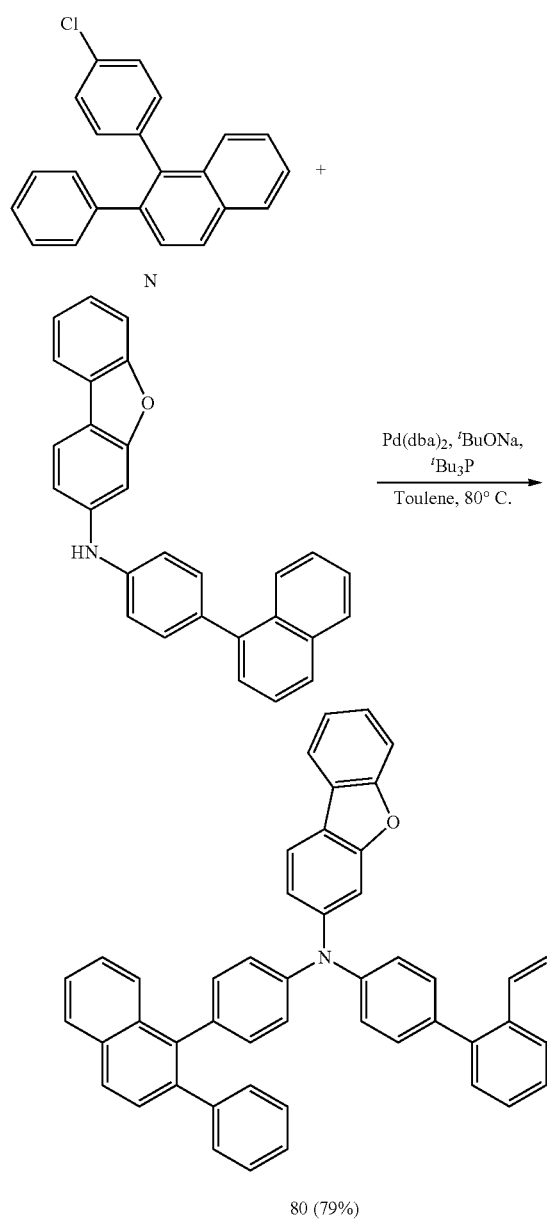

80 (79%)

Compound 80 was synthesized by conducting the same synthetic method of Compound 17 except for using Intermediate N instead of Intermediate F and using N-(4-(naphthalen-1-yl)phenyl)-3-dibenzofuranamine instead of N-[4-(1-naphthalenyl)phenyl]-3-dibenzothiophenamine in the synthetic method of Compound 17 (yield 79%).

The molecular weight of Compound 80 measured by FAB-MS was 663.

[$^1$H NMR (CDCl$_3$, 25° C., 300 Hz) δ=8.97-8.94 (m, 2H), 8.55 (d, J=8.2 Hz, 1H), 8.33-8.00 (m, 6H), 7.73-7.60 (m, 5H), 7.55-7.51 (m, 6H), 7.49-7.46 (m, 6H), 7.44-7.28 (m, 6H), 6.97 (d, J=8.3 Hz, 1H)]

88

6. Synthesis of Compound 105

(Synthesis of Intermediate O)

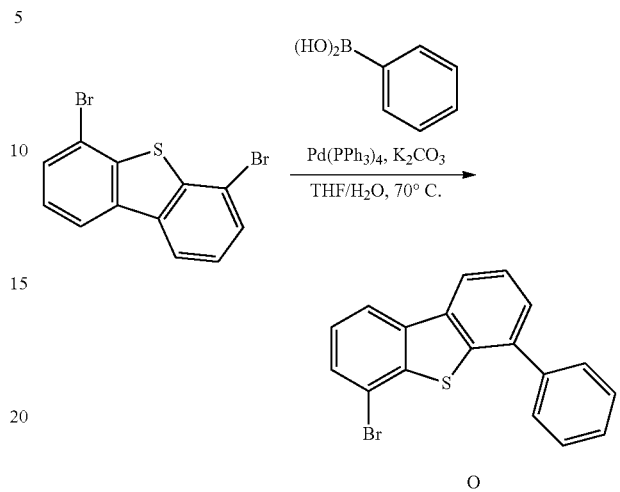

Intermediate O synthesized by conducting the same synthetic method of Intermediate E except for using 4,6-dibromodibenzothiophene (22.4 g) instead of 1,5-dibmmonaphthalene in the synthetic method of Intermediate E (yield 66%).

(Synthesis of Intermediate P)

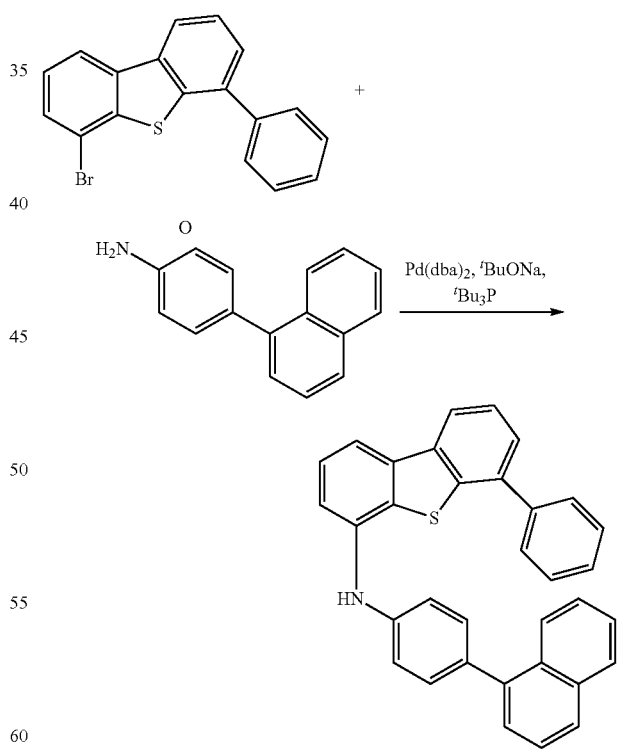

P (78%)

Intermediate P was synthesized by conducting the same synthetic method of Compound 1 except for using Intermediate O instead of Intermediate D and using N-[4-(1-naphthalenyl)phenyl]amine instead of N-[4-(1-naphthalenyl)phenyl]-4-dibenzothiophenamine in the synthetic method of Compound 1.

The molecular weight of Intermediate P measured by FAB-MS was 477.

(Synthesis of Compound 105)

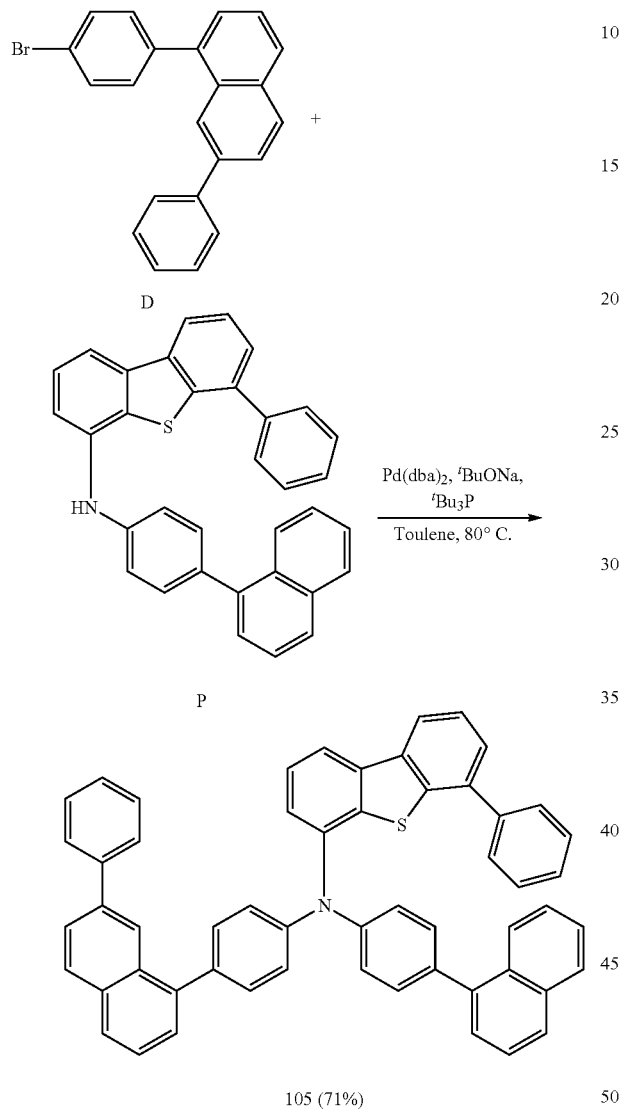

P 105 (71%)

Compound 105 was synthesized by conducting the same synthetic method of Compound 1 except for using Intermediate P instead of N-[4-(1-naphthalenyl)phenyl]-4-dibenzothiophenamine in the synthetic method of Compound 1 (yield 71%).

The molecular weight of Compound 105 measured by FAB-MS was 755.

[$^1$H NMR (CDCl$_3$, 25° C., 300 Hz) δ=8.85 (d, J=8.2 Hz, 1H), 8.55-8.52 (m, 3H), 8.44 (d, J=8.1 Hz, 1H), 8.35 (d, J=7.9 Hz, 1H), 8.21-8.08 (m, 4H), 8.01 (s, 1H), 7.80-7.69 (m, 5H), 7.64-7.54 (m, 6H), 7.50-7.40 (m, 6H), 7.38-7.33 (m, 7H)]

7. Synthesis of Compound 117

(Synthesis of Intermediate R)

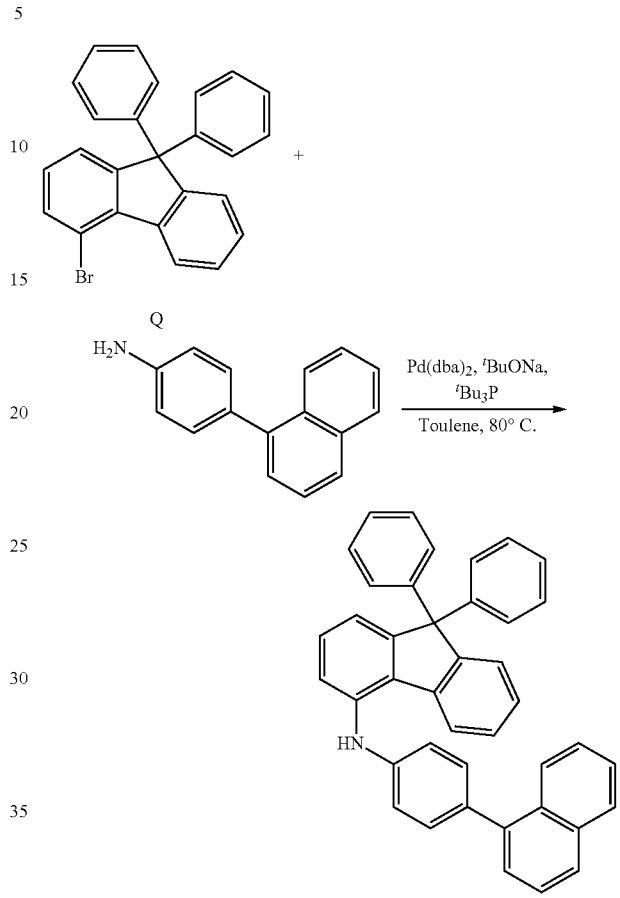

R (75%)

Intermediate R was synthesized by conducting the same synthetic method of Compound 1 except for using Intermediate Q instead of Intermediate D and using N-[4-(1-naphthalenyl)phenyl]amine instead of N-[4-(1-naphthalenyl)phenyl]-4-dibenzothiophenamine in the synthetic method of Compound 1.

The molecular weight of Intermediate R measured by FAB-MS was 535.

(Synthesis of Compound 117)

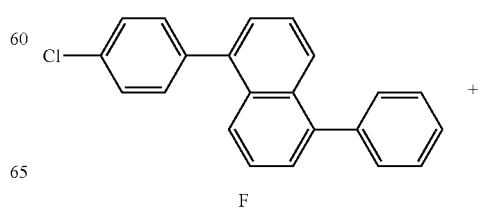

F

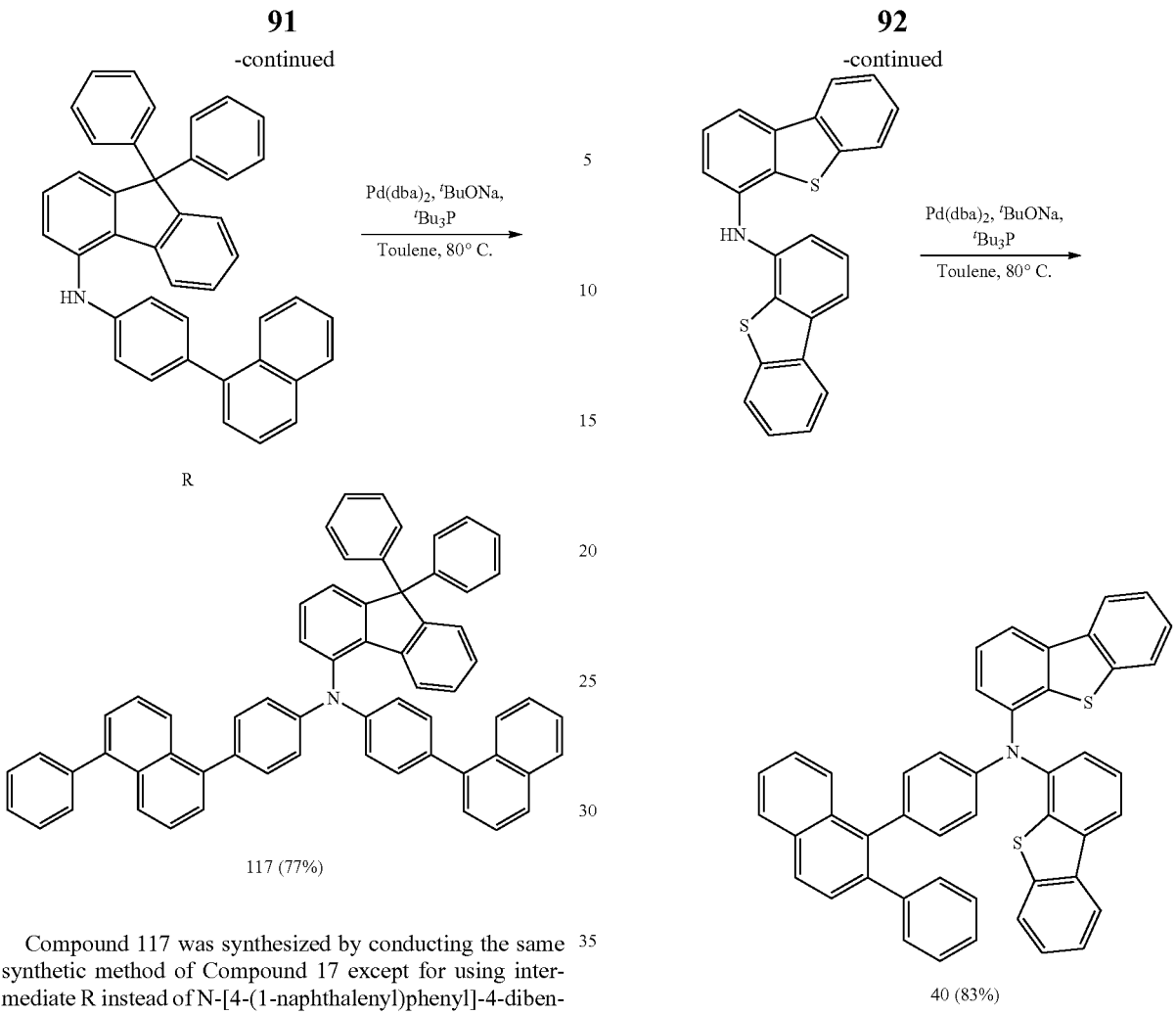

Compound 117 was synthesized by conducting the same synthetic method of Compound 17 except for using intermediate R instead of N-[4-(1-naphthalenyl)phenyl]-4-dibenzothiophenamine in the synthetic method of Compound 17 (yield 77%).

The molecular weight of Compound 117 measured by FAB-MS was 813.

[$^1$H NMR (CDCl$_3$, 25° C., 300 Hz) δ=8.99 (d, J-8.1 Hz, 1H), 8.90 (d, J=8.5 Hz, 1H), 8.87 (d, J=8.4 Hz, 1H), 8.54 (d, J=8.1 Hz, 1H), 8.38-8.37 (m, 2H), 8.24 (d, J=7.9 Hz, 1H), 8.11 (d, J=8.0 Hz, 1H), 7.99 (d, J=8.6 Hz, 1H), 7.81 (d, J=8.2 Hz, 2H), 7.80-7.69 (m, 3H), 7.60-7.54 (m, 5H), 4.48-4.40 (m, 4H), 7.38-7.35 (m, 6H). 7.29-7.21 (7H), 7.18-7.09 (m, 7H)]

8. Synthesis of Compound 40

(Synthesis of Compound 40)

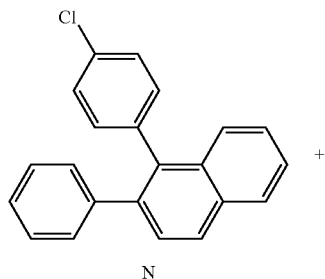

N

Compound 40 was synthesized by conducting the same synthetic method of Compound 17 except for using Intermediate N instead of Intermediate F and using N-4-dibenzofuranyl-4-dibenzofuranamine instead of N-[4-(1-naphthalenyl)phenyl]-4-dibenzothiophenamine in the synthetic method of Compound 17. The molecular weight of Compound 40 measured by FAB-MS was 659.

[$^1$H NMR (CDCl$_3$, 25° C., 300 Hz) δ=8.87 (d, J=7.5 Hz, 1H), 8.50 (d, J=7.7 Hz, 2H), 8.37-8.30 (m, 2H), 8.15 (m, 2H), 8.01 (d, J=7.5 Hz, 2H), 7.85 (d, J=8.2 Hz, 2H), 7.76 (d, J=8.1 Hz, 1H), 7.60 (m, 2H), 7.53-7.49 (m, 7H), 7.46 (d, J=8.3 Hz, 2H), 7.42-7.39 (m, 4H), 7.37 (d, J=8.3 Hz, 2H)]

9. Synthesis of Compound 189

(Synthesis of Compound 189)

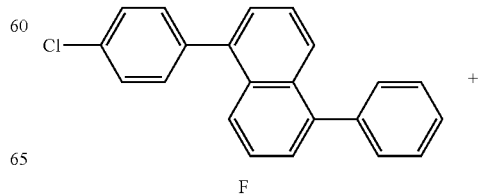

F

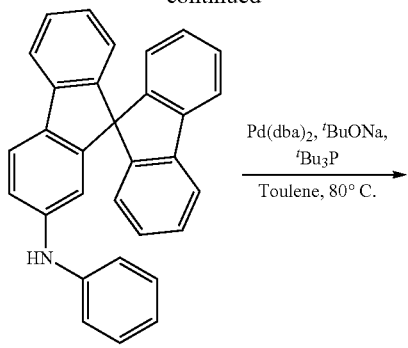

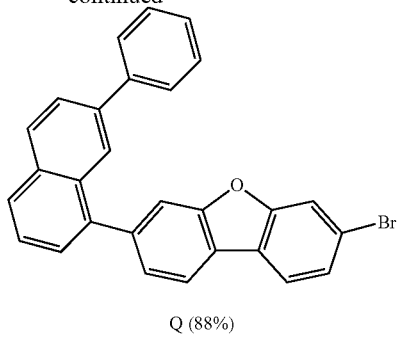

Q (88%)

Intermediate Q was synthesized by conducting the same synthetic method of Intermediate L except for using 2-(7-bromodibenzofuran-3-yl)-4,4,5,5-tetramethyl-1,3,2-dioxaborolane instead of 3-bromophenylboronic acid in the synthetic method of Intermediate L. The molecular weight of Intermediate Q measured by FAB-MS was 449.

(Synthesis of Compound 203)

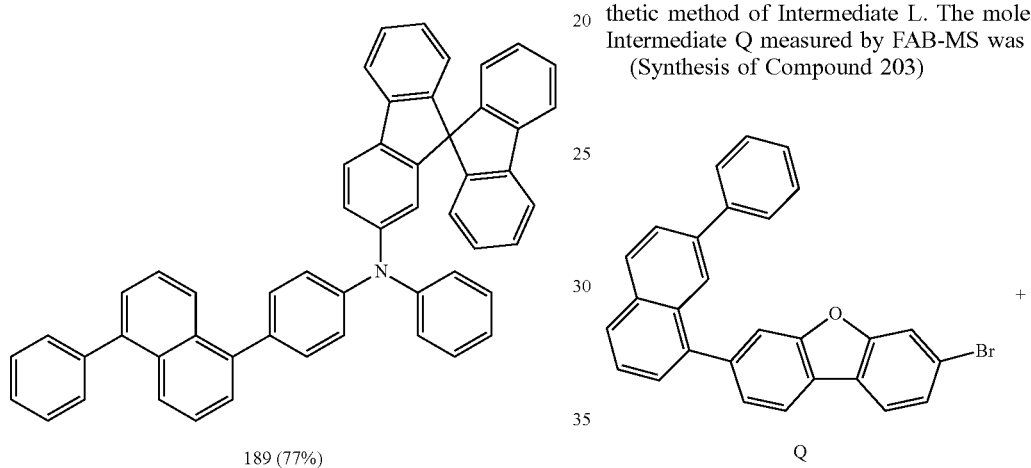

189 (77%)

Compound 189 was synthesized by conducting the same synthetic method of Compound 17 except for using N-phenyl-9,9'-spirobisfluoren-2-amine instead of N-[4-(1-naphthalenyl)phenyl]-4-dibenzothiophenamine in the synthetic method of Compound 17. The molecular weight of Compound 189 measured by FAB-MS was 685.

[$^1$H NMR (CDCl$_3$, 25° C., 300 Hz) δ=8.79 (m, 2H), 8.44 (m, 2H), 7.92-7.82 (m, 4H), 7.79 (d, J=8.2 Hz, 2H), 7.68 (m, 2H), 7.60 (d, J=8.1 Hz, 2H), 7.50-7.41 (m, 7H), 7.39-7.33 (m, 4H), 7.29-7.23 (m, 9H), 7.12 (t, J=8.2 Hz, 1H)]

10. Synthesis of Compound 203

(Synthesis of intermediate Q)

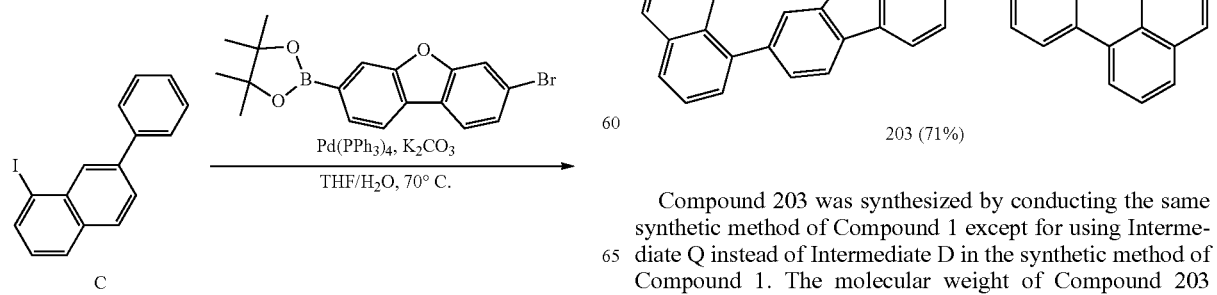

203 (71%)

Compound 203 was synthesized by conducting the same synthetic method of Compound 1 except for using Intermediate Q instead of Intermediate D in the synthetic method of Compound 1. The molecular weight of Compound 203 measured by FAB-MS was 769.

[¹H NMR (CDCl₃, 25° C., 300 Hz) δ=8.90 (d, J=7.9 Hz, 1H), 8.61 (d, J=8.2 Hz, 1H), 8.56 (d, J=8.1 Hz, 1H), 8.45-8.41 (m, 2H), 8.25-8.21 (m, 2H), 8.14-8.07 (m, 2H), 8.01-7.98 (m, 3H), 7.91-7.75 (m, 7H), 7.60-7.51 (m, 10H), 7.42-7.35 (m, 5H), 6.99 (d, J=7.9 Hz, 1H)]

11. Synthesis of Compound 206

(Synthesis of Intermediate R)

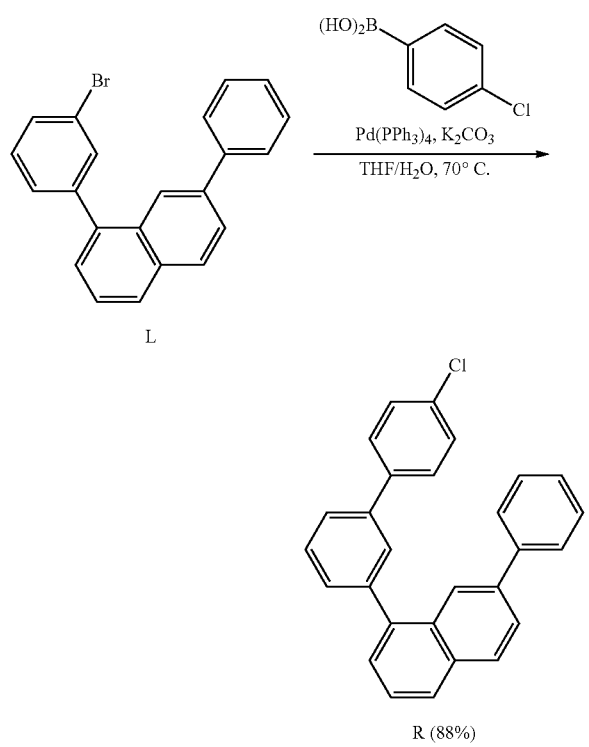

R (88%)

Intermediate R was synthesized by conducting the same synthetic method of Intermediate F except for using Intermediate L instead of Intermediate E in the synthetic method of Intermediate F. The molecular weight of Intermediate R measured by FAB-MS was 390.

(Synthesis of Compound 206)

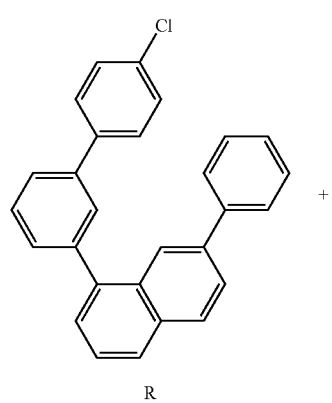

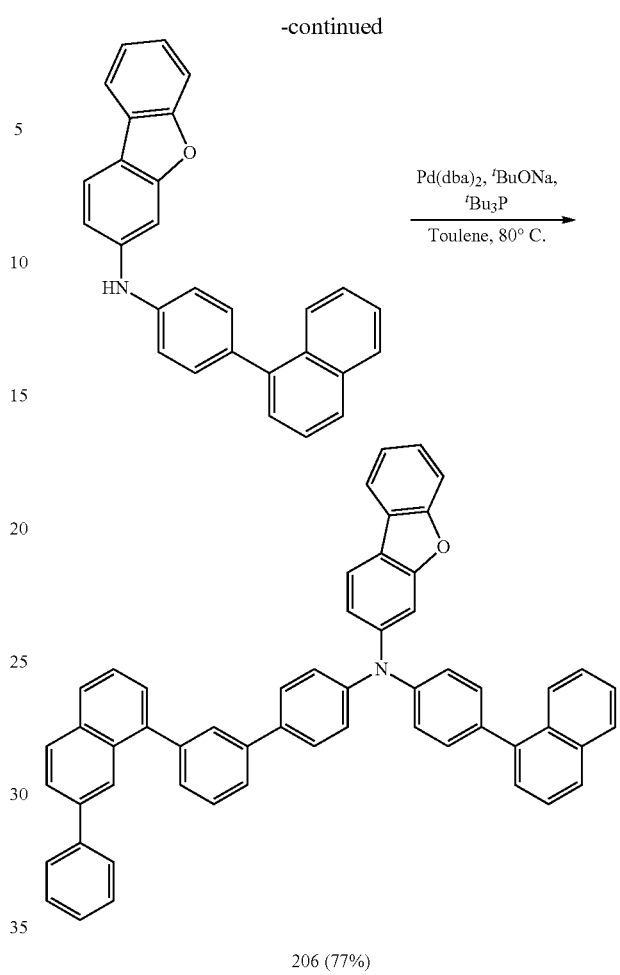

206 (77%)

Compound 206 was synthesized by conducting the same synthetic method of Compound 80 except for using intermediate R instead of Intermediate N in the synthetic method of Compound 80. The molecular weight of Compound 206 measured by FAB-MS was 739.

[¹H NMR (CDCl₃, 25° C., 300 Hz) 5=8.81 (d, J=7.9 Hz, 1H), 8.66 (d, J=8.1 Hz, 1H), 8.54 (d, J=8.1 Hz, 1H), 8.46 (m, 1H), 8.31 (m, 1H), 8.21 (m, 1H). 8.10-8.01 (m, 3H), 7.98-7.95 (m, 2H), 7.84 (m, 1H), 7.79-7.74 (4H), 6.69-7.61 (m, 3H), 7.55-7.41 (m, 12H), 7.38-7.35 (m, 6H), 7.01 (d, J=8.0 Hz, 1H)]

The above-described synthesis examples are illustrated for assisting the understanding of those skilled in the art, and the reaction conditions may be modified if desired. Furthermore, the compound according to an example embodiment may be synthesized to have a variety of substituents by using various methods and materials. The compound may have features suitable for an organic electroluminescence device by introducing a variety of substituents to the core structure represented by Formula 1.

Device Manufacturing Example

Organic electroluminescence devices of Examples 1 to 11 were manufactured by using the above Compounds 1, 17, 71, 94, 80, 105, 117, 40, 189, 203, and 206 as an electron blocking material.

Example Compounds
1
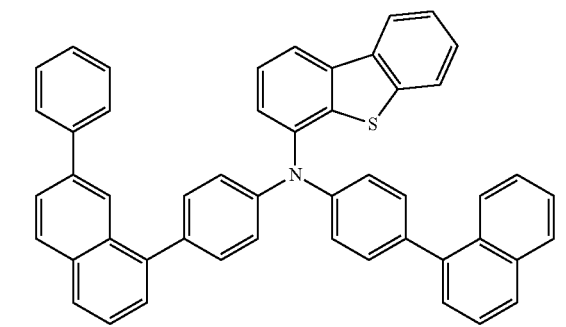
17
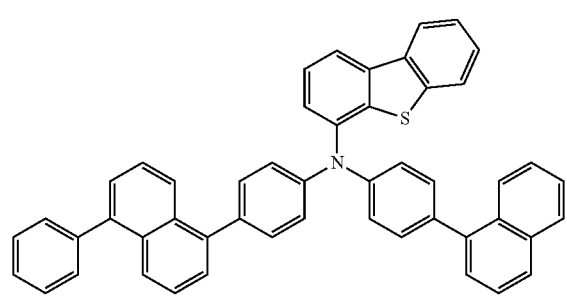
71
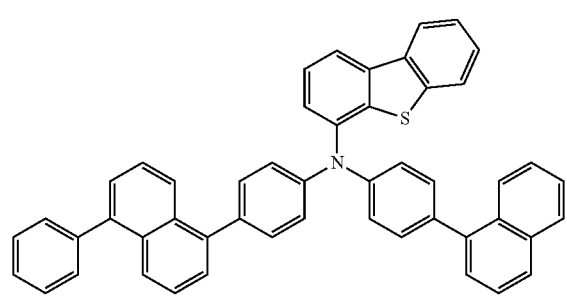
94
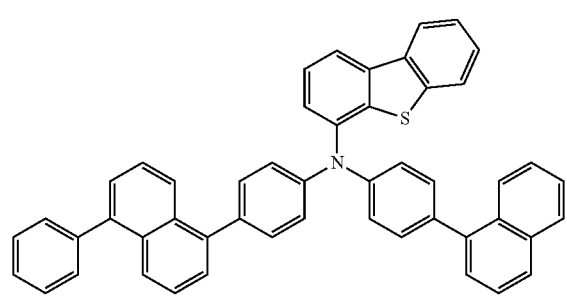
80
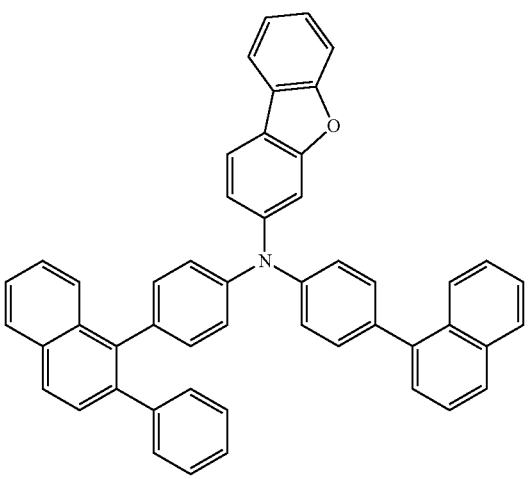
105
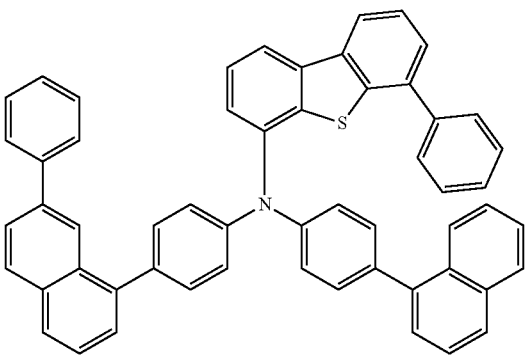
117
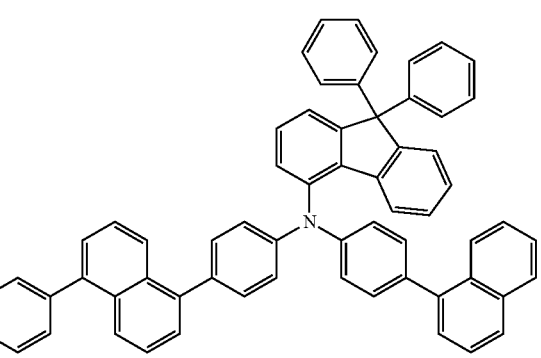
40
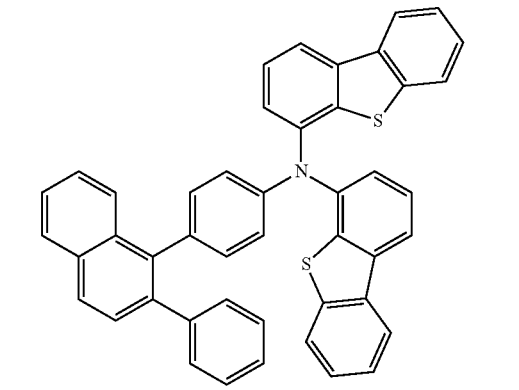

-continued
189
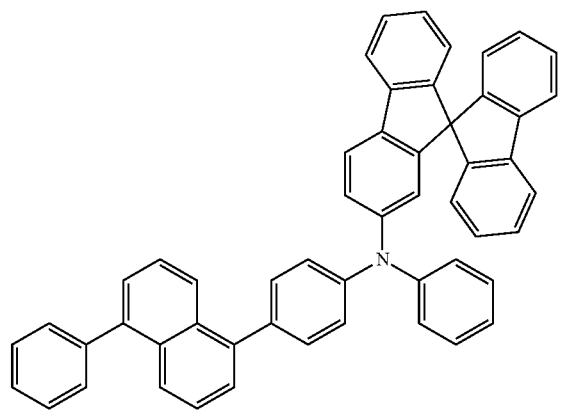
203
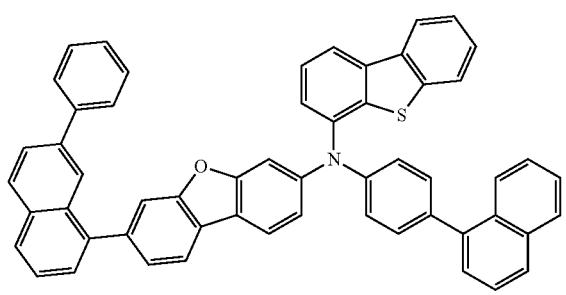
206
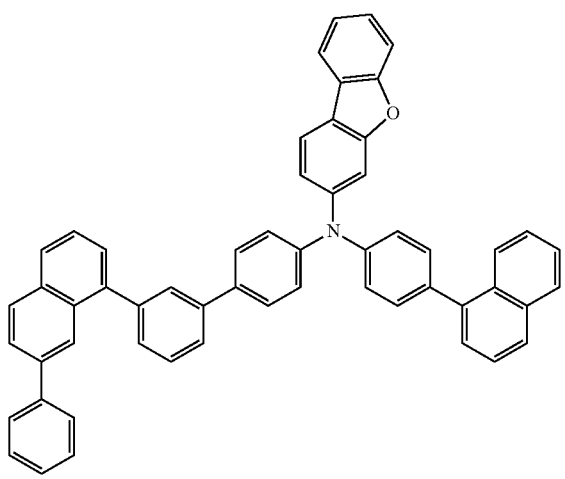
Comparative Compounds
A-1
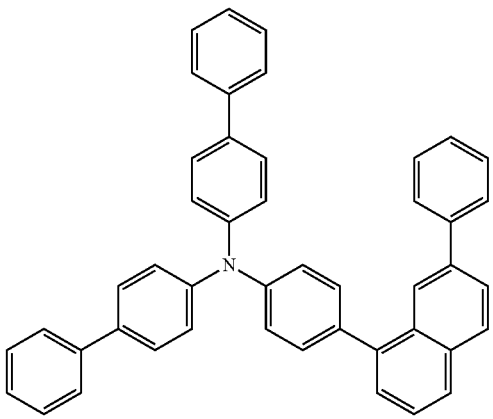
A-2
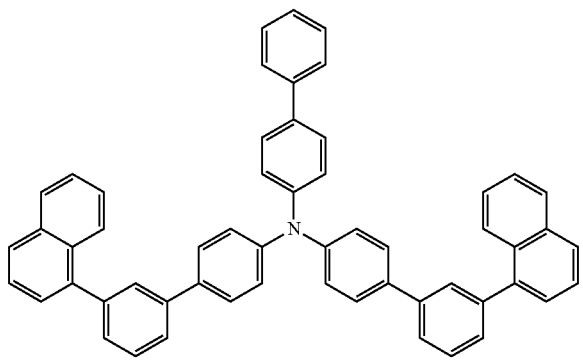
A-3
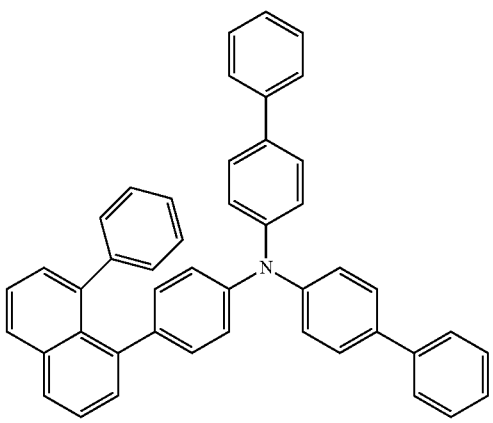
Organic electroluminescent devices of Comparative Examples 1 to 9 were manufactured by using the following Comparative Compounds A-1 to A-9.

-continued

A-4
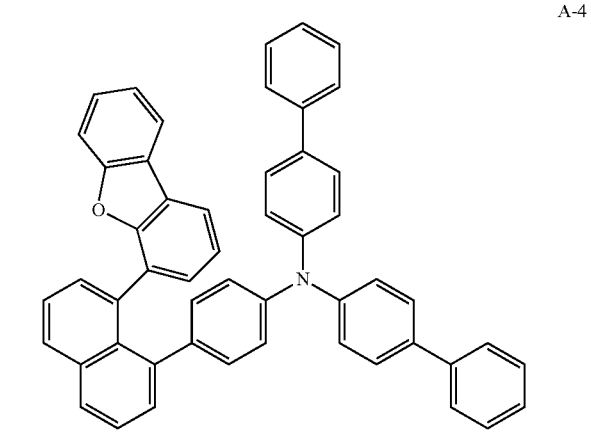

A-5
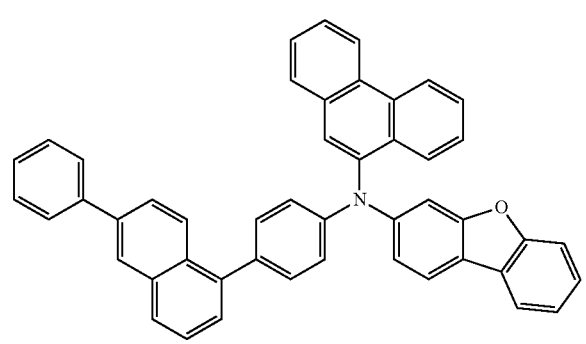

A-6
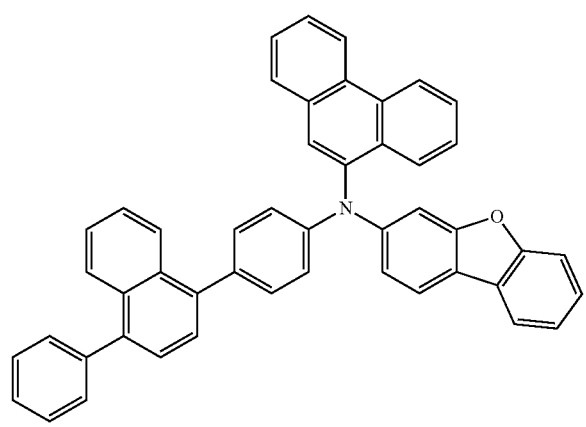

A-7
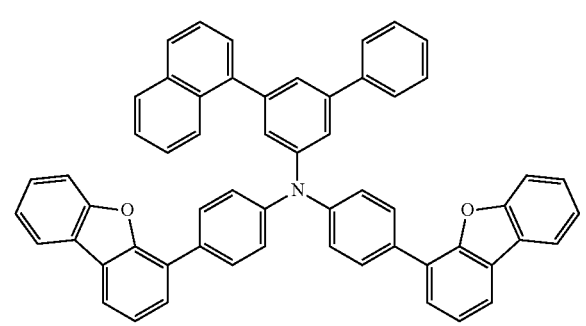

-continued

A-8
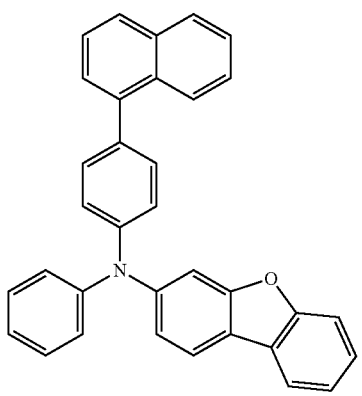

A-9
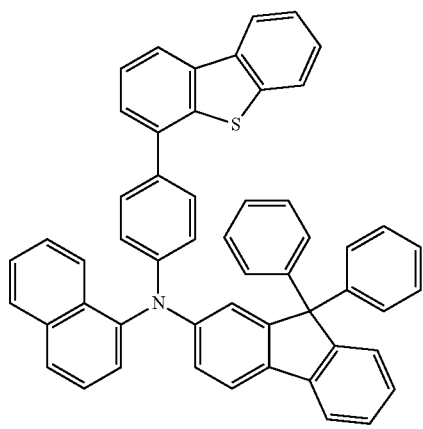

The organic electroluminescence devices according to Examples 1 to 11 and Comparative Examples 1 to 9 were manufactured by forming a first electrode using ITO to a thickness of about 150 nm, a hole injection layer using HT1 doped with 2% HIL to a thickness of about 10 nm, a hole transport layer using HT1 to a thickness of about 120 nm, an electron blocking layer using the example compounds or the comparative compounds to a thickness of about 10 nm, an emission layer using BH doped with 2% BD to a thickness of about 30 nm, a hole blocking layer using ET1 to a thickness of about 10 nm, an electron transport layer using ET2 to a thickness of about 20 nm, an electron injection layer using LiF to a thickness of about 1 nm, and a second electrode using a Mg/Ag alloy co-deposited at a volumetric ratio of 9:1 to a thickness of about 120 nm. Each layer was formed by a vacuum deposition method.

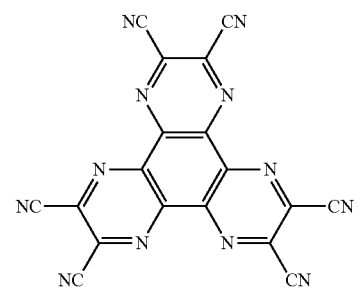
HIL

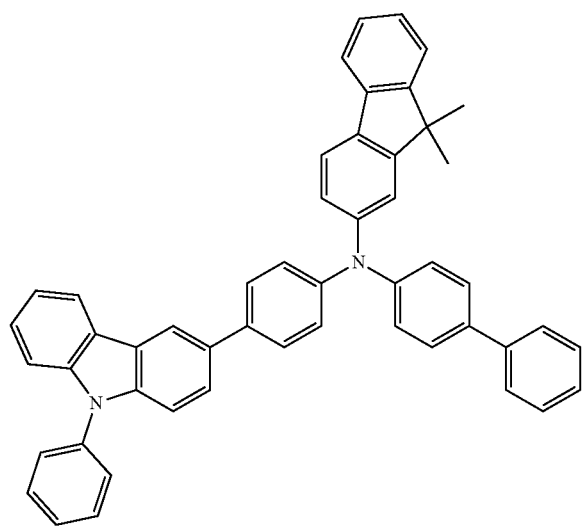

HT1

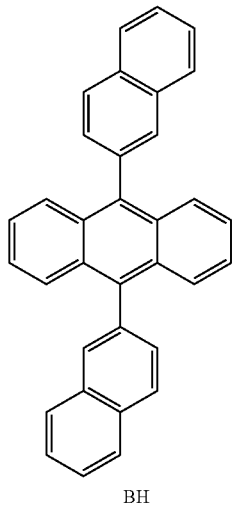

BH

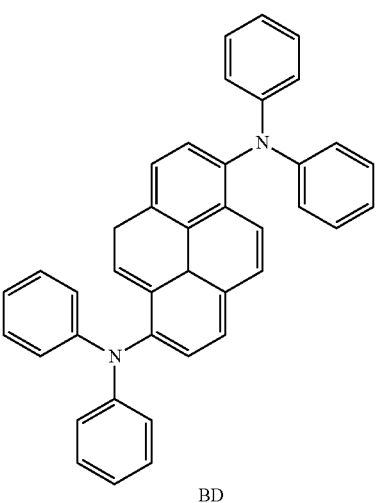

BD

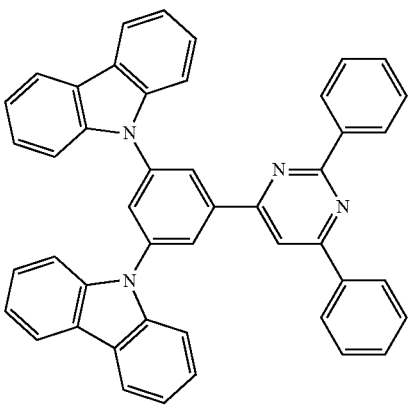

ET1

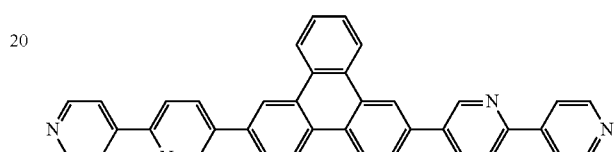

ET2

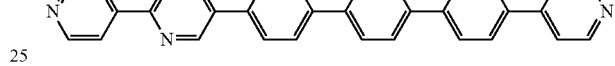

The voltage, half-life, emission efficiency, and color coordinate of the organic electroluminescence devices manufactured in Examples 1 to 11 and Comparative Examples 1 to 9 are shown in Table 1 below.

TABLE 1

| | Electron blocking layer | Voltage (V) | Life LT50 (h) | Emission efficiency (cd/A) | Color coordinate CIE (x, y) |
|---|---|---|---|---|---|
| Example 1 | Example Compound 1 | 4.5 | 182 | 5.3 | 0.141, 0.052 |
| Example 2 | Example Compound 17 | 4.7 | 189 | 5.1 | 0.142, 0.052 |
| Example 3 | Example Compound 71 | 4.7 | 200 | 4.9 | 0.141, 0.051 |
| Example 4 | Example Compound 94 | 4.7 | 183 | 5.4 | 0.141, 0.051 |
| Example 5 | Example Compound 80 | 4.6 | 193 | 5.4 | 0.141, 0.052 |
| Example 6 | Example Compound 105 | 4.7 | 182 | 5.4 | 0.141, 0.052 |
| Example 7 | Example Compound 117 | 4.7 | 178 | 5.1 | 0.141, 0.051 |
| Example 8 | Example Compound 40 | 4.6 | 184 | 5.5 | 0.142, 0.052 |
| Example 9 | Example Compound 189 | 4.5 | 188 | 5.2 | 0.142, 0.051 |
| Example 10 | Example Compound 203 | 4.7 | 187 | 5.0 | 0.141, 0.051 |
| Example 11 | Example Compound 206 | 4.6 | 186 | 5.4 | 0.140, 0.052 |
| Comparative Example 1 | Comparative Compound A-1 | 4.8 | 167 | 4.1 | 0.141, 0.052 |
| Comparative Example 2 | Comparative Compound A-2 | 4.9 | 160 | 3.8 | 0.140, 0.051 |
| Comparative Example 3 | Comparative Compound A-3 | 4.8 | 164 | 3.9 | 0.140, 0.052 |
| Comparative Example 4 | Comparative Compound A-4 | 5.1 | 160 | 4.0 | 0.140, 0.051 |
| Comparative Example 5 | Comparative Compound A-5 | 4.8 | 163 | 4.1 | 0.141, 0.053 |
| Comparative Example 6 | Comparative Compound A-6 | 5.1 | 160 | 4.1 | 0.141, 0.050 |
| Comparative Example 7 | Comparative Compound A-7 | 5.1 | 160 | 4.0 | 0.140, 0.051 |
| Comparative Example 8 | Comparative Compound A-8 | 4.9 | 160 | 4.1 | 0.141, 0.052 |

TABLE 1-continued

| Electron blocking layer | | Voltage (V) | Life LT50 (h) | Emission efficiency (cd/A) | Color coordinate CIE (x, y) |
|---|---|---|---|---|---|
| Comparative Example 9 | Comparative Compound A-9 | 5.0 | 163 | 4.1 | 0.141, 0.052 |

In the above table, the emission efficiency was a measured value at a current density of about 10 mA/cm$^2$, and the half-life was a value at about 1.0 mA/cm$^2$.

Referring to the results in Table 1, it may be found that the organic electroluminescence devices of Examples 1 to 11 had decreased driving voltage, extended life and enhanced efficiency when compared with those of Comparative Examples 1 to 9. The monoamine compound according to an example embodiment includes a phenylnaphthyl group with a high thermal resistance and electric charge resistance, which may help provide an extended device life. Furthermore, the monoamine compound has a bulky naphthyl group substituted with a phenyl group, which decreases symmetry of molecule and may inhibit crystallization, and may thus enhance the quality of layers and help provide high efficiency of the device.

The organic electroluminescence devices of Examples 1 to 11 use the example compounds including a naphthyl group connected to the nitrogen atom at position 1 via a linker, which may inhibit crystallization due to the bulky molecular structure, to thereby enhance quality of layers and attain improved emission efficiency.

The organic electroluminescence device of Comparative Example 1 uses an amine compound including a phenylnaphthyl group but not a condensed ring connected to the nitrogen atom, which results in low electric charge resistance, thereby decreasing device life. The organic electroluminescence device of Comparative Example 2 uses an amine compound including a naphthyl group but not a phenylnaphthyl group, which results in low electric charge resistance, thereby decreasing device life and emission efficiency due to the insufficient quality of layers.

The organic electroluminescence devices of Comparative Examples 3 and 4 use Comparative Compounds A-3 and A-4 including a substituted naphthyl group but not a condensed ring connected directly to the nitrogen atom, which results in low electric charge resistance, thereby decreasing device life. Furthermore, Comparative Compounds A-3 and A-4 have a bulky naphthyl group with substituents at both positions 1 and 8, which results in easy decomposition and long intermolecular distance, thereby delaying hole transport and decreasing device life and efficiency when compared with those of Examples.

The organic electroluminescence devices of Comparative Examples 5 and 6 use Comparative Compounds A-5 and A-6 including a phenanthrene ring having more than 12 ring carbon atoms, which causes a strong molecular stacking and increased deposition temperature, thereby resulting in easy thermal decomposition and decreasing efficiency and device life.

The organic electroluminescence device of Comparative Example 7 uses Comparative Compound A-7 including fused heterocycles connected to the nitrogen atom via p-phenylene group, which results in weak stabilizing effect of amine, thereby decreasing device life. The organic electroluminescence device of Comparative Example 8 uses Comparative Compound A-8 including a fused heterocycle connected directly to the nitrogen atom but not including a phenylnaphthyl group, which results in weak stabilizing effect of amine, thereby decreasing device life.

The organic electroluminescence device of Comparative Example 9 uses Comparative Compound A-9 including a naphthyl group connected directly to the amine group, which results in easy decomposition due to the bulky amine group, thereby decreasing device life. Furthermore, Comparative Compound A-9 includes both a fluorenyl group and a fused heterocycle, which weakens the electric charge balance in the device due to excessive introduction of substituents with strong electric charge transport property, thereby decreasing device life and efficiency.

By way of summation and review, in an application of an organic electroluminescence device to a display, decrease of a driving voltage, increase of emission efficiency and extension of life for the organic electroluminescence device are desired, and development of a material which may stably implement these requirements in the organic electroluminescence device is also desired.

Embodiments may provide an organic electroluminescence device and a monoamine compound for an organic electroluminescence device. Embodiments may provide an organic electroluminescence device with high efficiency and a monoamine compound included in a hole transport region of an organic electroluminescence device.

The monoamine compound according to an example embodiment may be used as a material for a hole transport region of an organic electroluminescence device, which may contribute to a decrease of a driving voltage, increase of emission efficiency, and extension of life for the organic electroluminescence device.

The organic electroluminescence device according to an example embodiment may have high efficiency.

The monoamine compound according to an example embodiment may be used as a material for a hole transport region of an organic electroluminescence device, and may enhance efficiency and life of the organic electroluminescence device.

The monoamine compound according to an example embodiment may be used as a material for a hole transport region of an organic electroluminescence device, and may decrease a driving voltage of the organic electroluminescence device.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A monoamine compound represented by Formula 1:

[Formula 1]

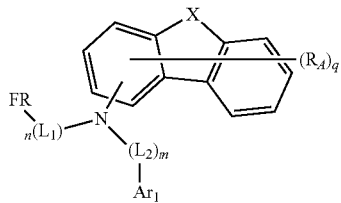

wherein in Formula 1,

X is S, O or CRR',

R and R' are each independently a substituted or unsubstituted alkyl group having 1 to 10 carbon atoms, a substituted or unsubstituted aryl group having 6 to 20 ring carbon atoms, or a substituted or unsubstituted heteroaryl group having 2 to 10 ring carbon atoms, and are separate or form a ring by combining adjacent groups with each other, $L_1$ is an unsubstituted phenylene group, an unsubstituted biphenylene group, or an unsubstituted heteroarylene group having 2 to 12 carbon atoms for forming a ring, $L_2$ is a direct linkage, a substituted or unsubstituted arylene group having 6 to 12 ring carbon atoms, or a substituted or unsubstituted heteroarylene group having 2 to 12 ring carbon atoms, m is an integer of 0 to 2, n is 1 or 2, $R_A$ is a hydrogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, q is an integer of 0 to 7, $Ar_1$ is a substituted or unsubstituted aryl group having 6 to 12 ring carbon atoms, or a substituted or unsubstituted heteroaryl group selected from thiophenyl, furanyl, pyrrolyl, imidazolyl, thiazolyl, oxazolyl, oxadiazolyl, triazolyl, pyridinyl, bipyridinyl, pyrimidinyl, triazinyl, triazolyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, N-aryl carbazolyl, N-heteroaryl carbazolyl, N-alkyl carbazolyl, benzoxazolyl, benzimidazoyl, benzothiazolyl, dibenzothiophenyl, thienothiophenyl, phenanthrolinyl, thiazolyl, isoxazolyl, oxadiazolyl, thiadiazolyl, and phenothiazinyl, provided that when X is CRR', $Ar_1$ does not comprise a heteroaryl group, and FR is represented by one of the following:

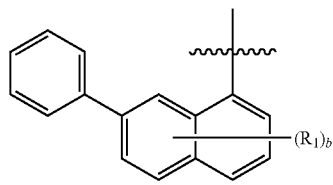

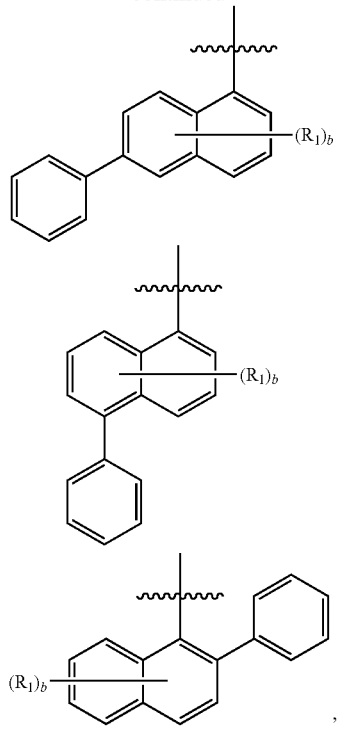

wherein $R_1$ is a hydrogen atom, a deuterium atom, or a halogen atom, and b is an integer of 0 to 6.

2. The monoamine compound as claimed in claim 1, wherein n is 1, and $L_1$ is an unsubstituted phenylene group, an unsubstituted biphenylene group.

3. The monoamine compound as claimed in claim 2, wherein $L_1$ is an unsubstituted phenylene group.

4. The monoamine compound as claimed in claim 3, wherein FR is substituted on the phenylene group at a para position to the amine nitrogen atom.

5. The monoamine compound as claimed in claim 3, wherein FR is substituted on the phenylene group at a meta position to the amine nitrogen atom.

6. The monoamine compound as claimed in claim 3, wherein FR is substituted on the phenylene group at an ortho position to the amine nitrogen atom.

7. The monoamine compound as claimed in claim 1, wherein m is 1, $L_2$ is a substituted or unsubstituted arylene group having 6 to 12 ring carbon atoms, and $Ar_1$ is a substituted or unsubstituted aryl group having 6 to 12 ring carbon atoms.

8. The monoamine compound as claimed in claim 7, wherein $L_2$ is a substituted or unsubstituted phenylene group, and $Ar_1$ is a substituted or unsubstituted phenyl group, a substituted or unsubstituted biphenyl group, or a substituted or unsubstituted naphthyl group.

9. The monoamine compound as claimed in claim 1, wherein m is 0, and $Ar_1$ is a substituted or unsubstituted heteroaryl group selected from pyridinyl, bipyridinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, N-aryl carbazolyl, N-heteroaryl carbazolyl, N-alkyl carbazolyl, benzoxazolyl, benzimidazoyl, benzothiazolyl, dibenzothiophenyl, thienothiophenyl, phenanthrolinyl, and phenothiazinyl.

10. The monoamine compound as claimed in claim 9, wherein Ar₁ is a substituted or unsubstituted dibenzothiophene group.
11. The monoamine compound as claimed in claim 1, wherein the monoamine compound represented by Formula 1 is selected from Compound Group 1:
[Compound Group 1]
1
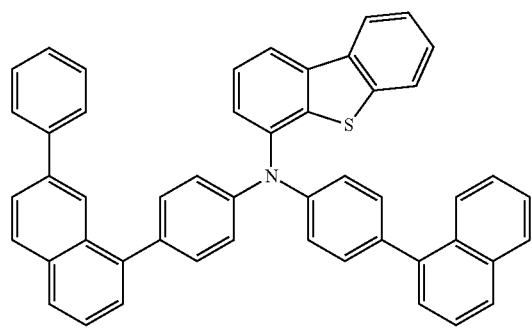
2
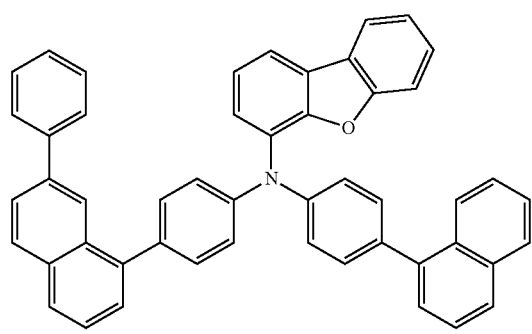
3
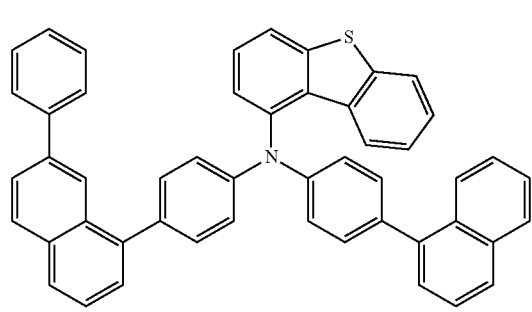
4
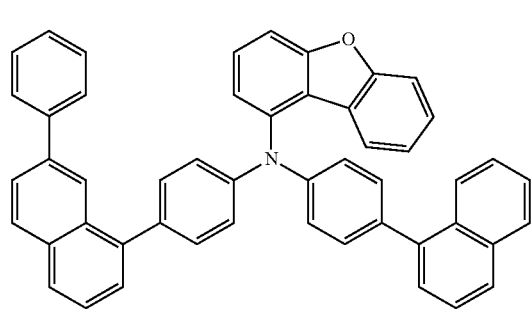
5
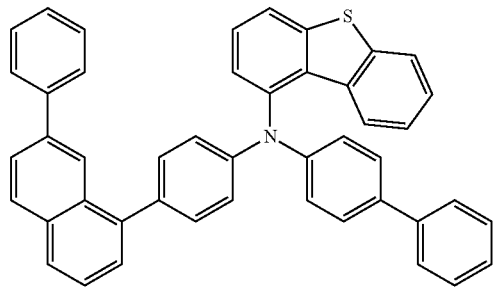
6
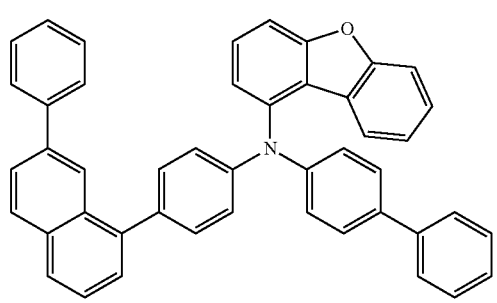
8
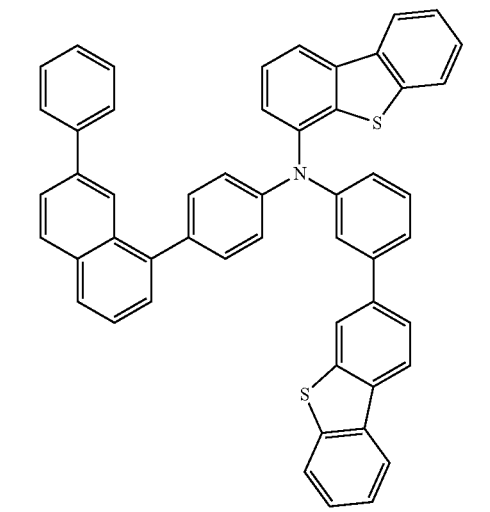
9
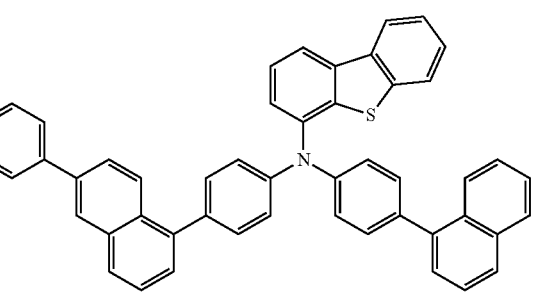

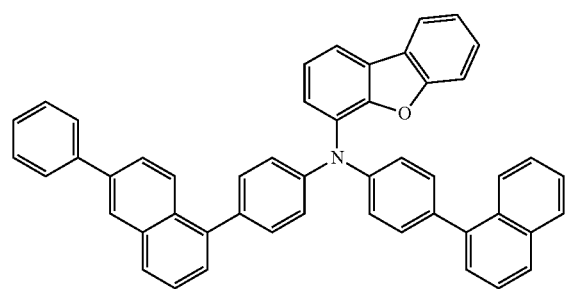
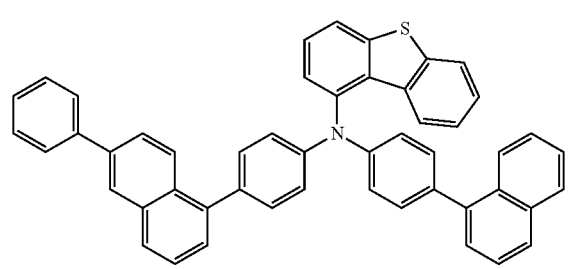
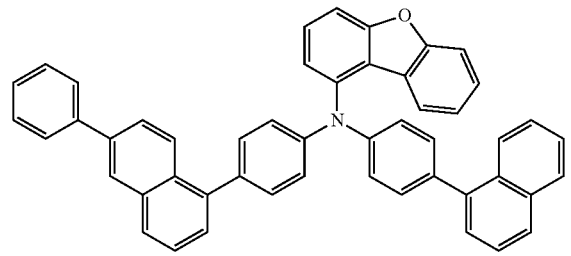
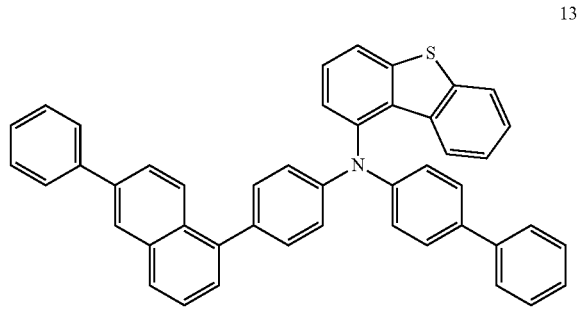
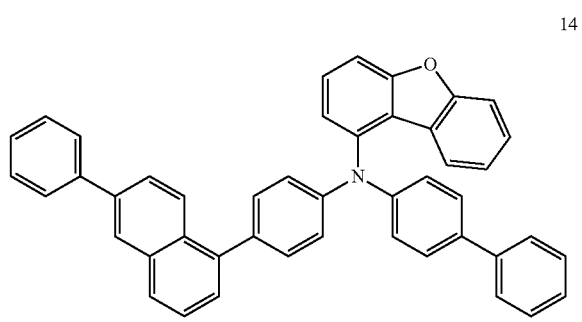
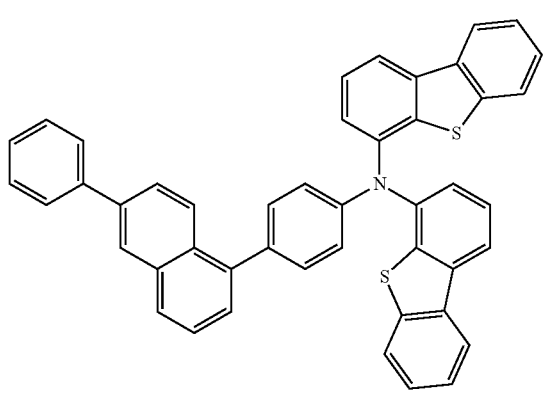
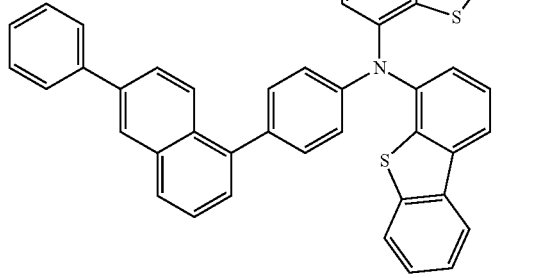
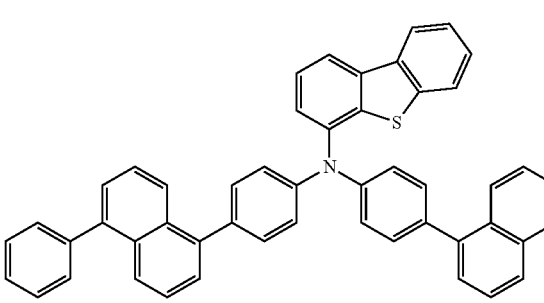
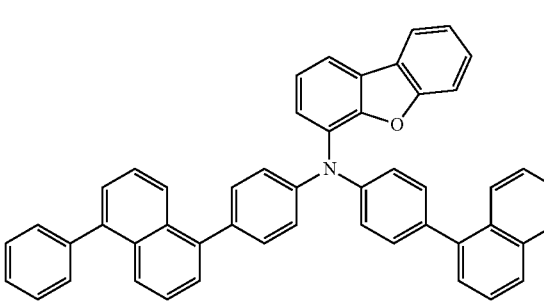
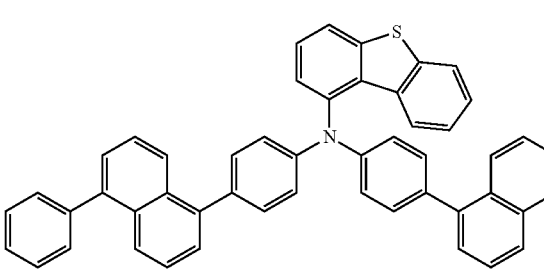
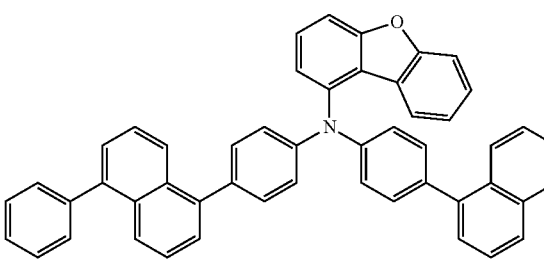

21
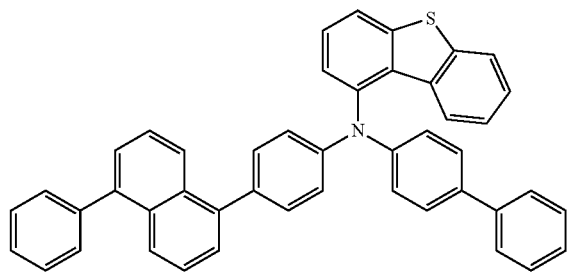
22
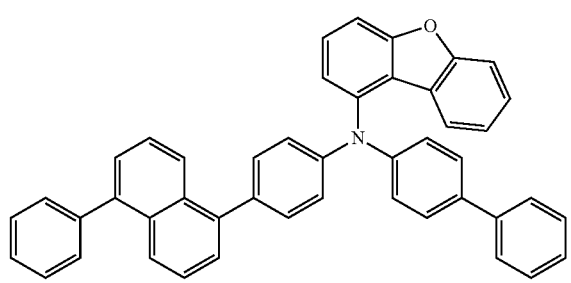
24
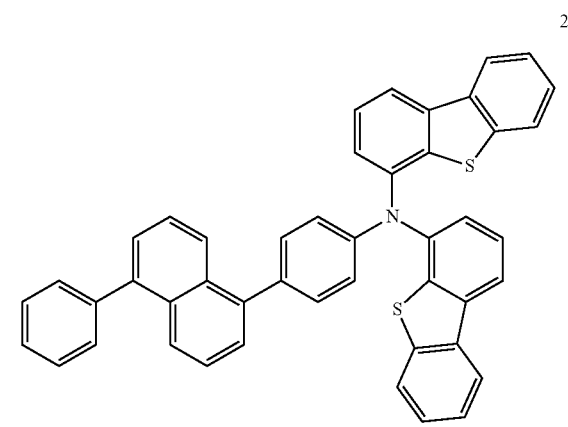
33
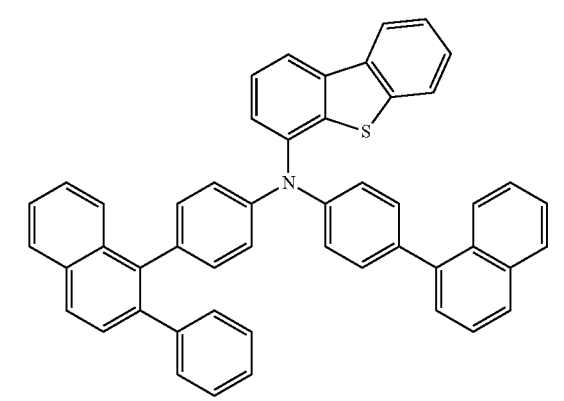
34
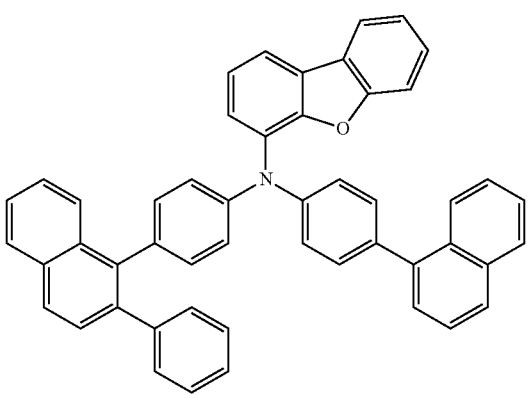
35
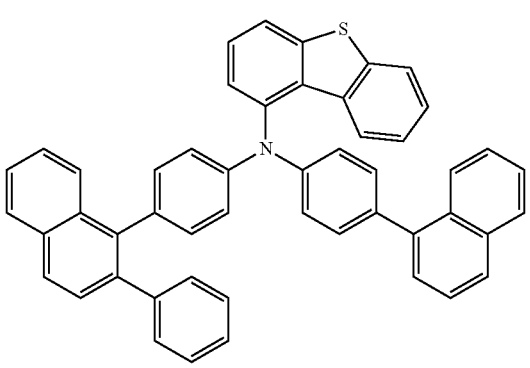
36
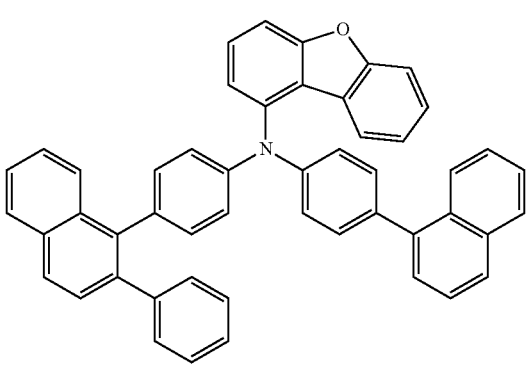
37
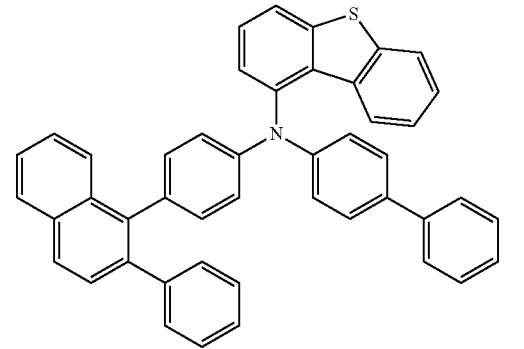

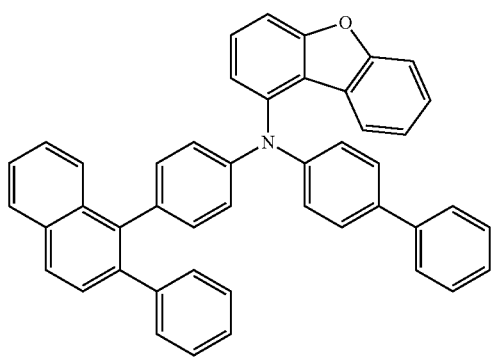
38
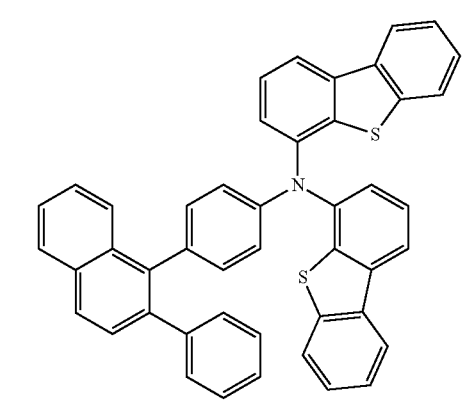
40
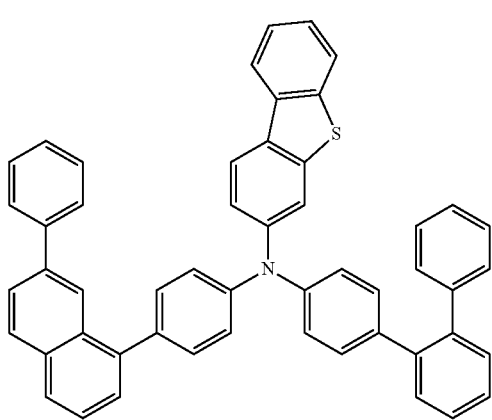
49
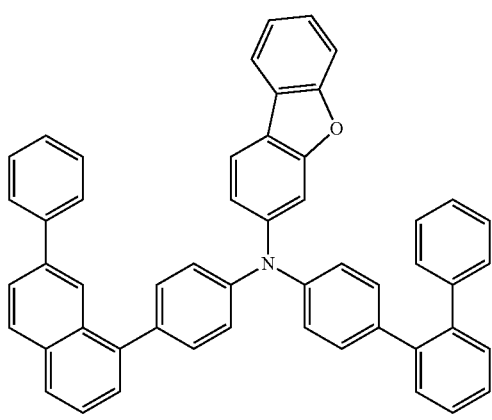
50
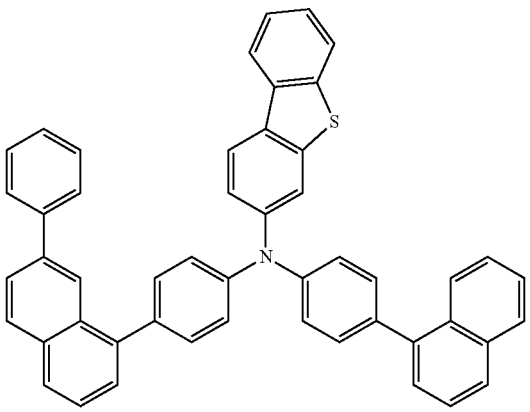
51
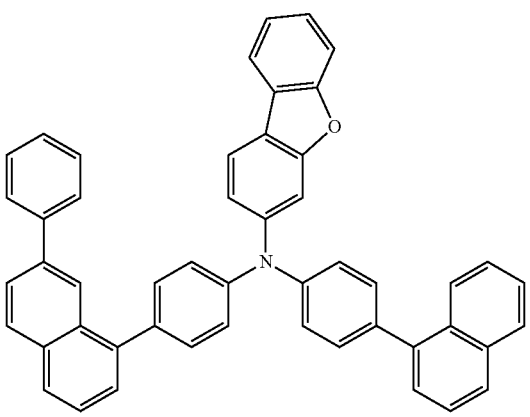
52
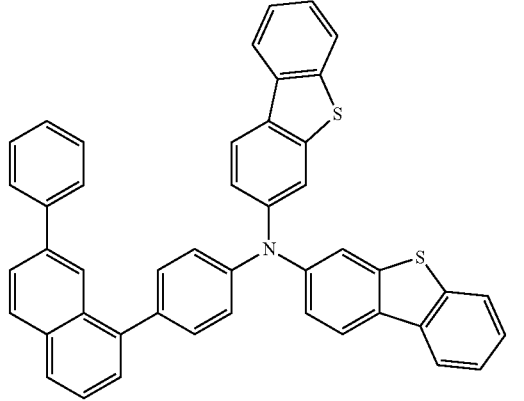
54
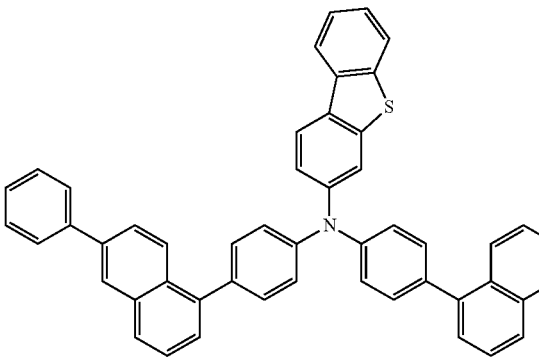
55

56
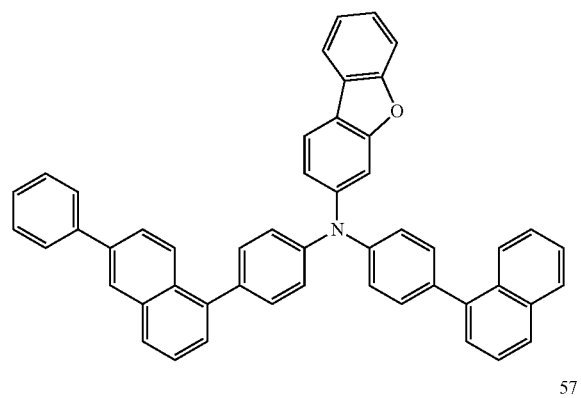
57
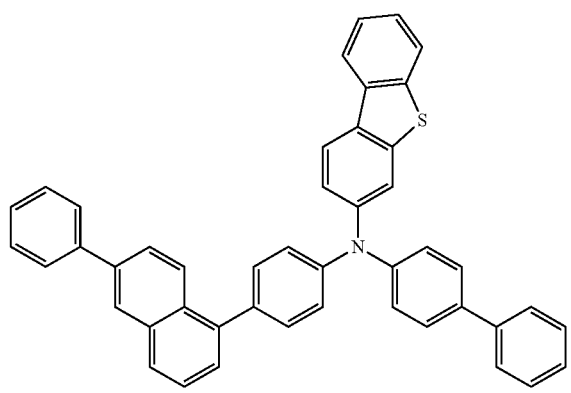
58
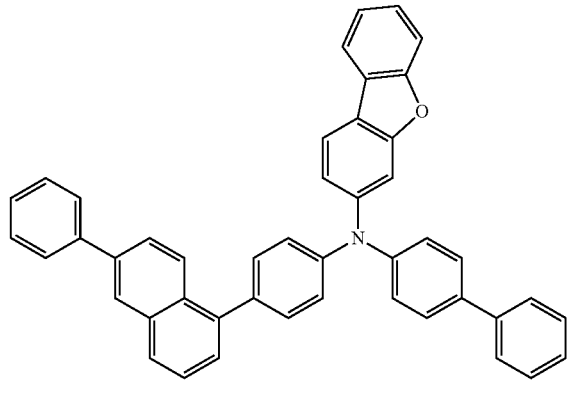
60
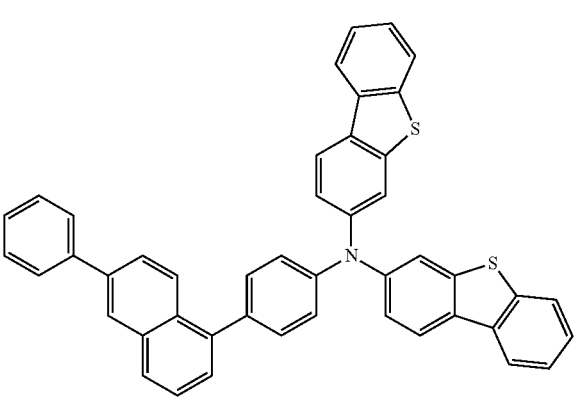
61
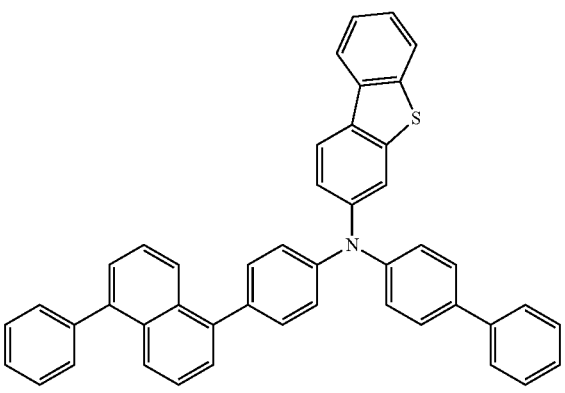
62
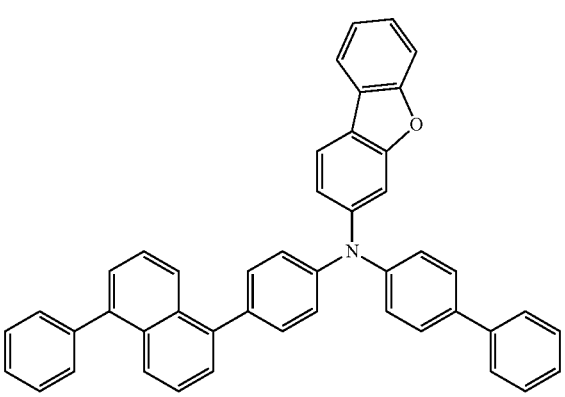
63
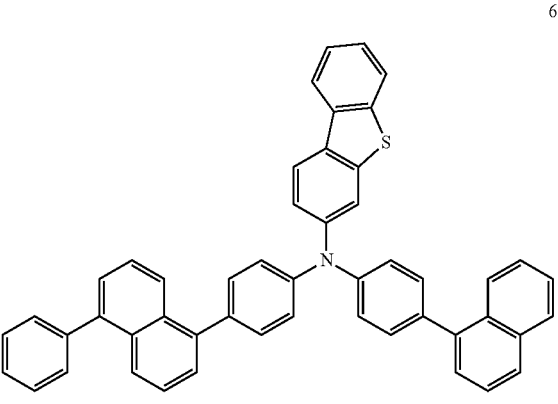
64
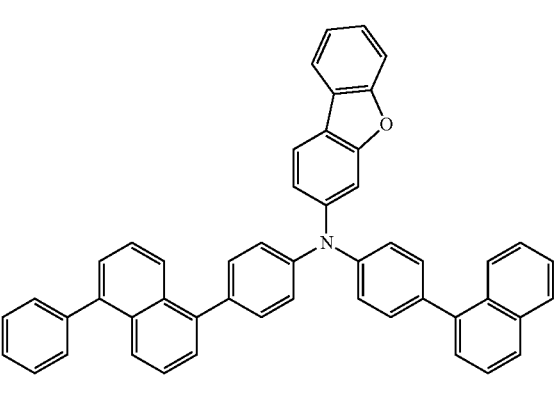

-continued
66
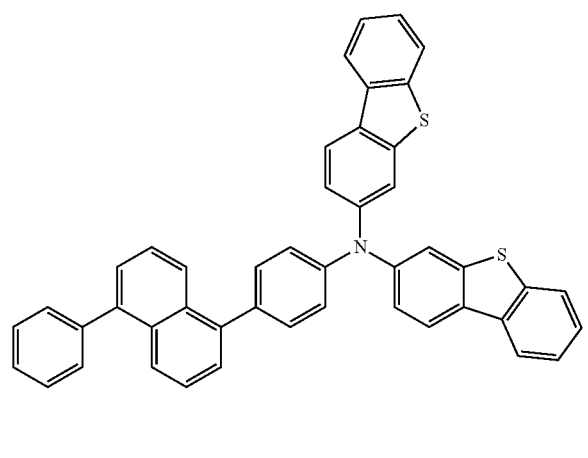
79
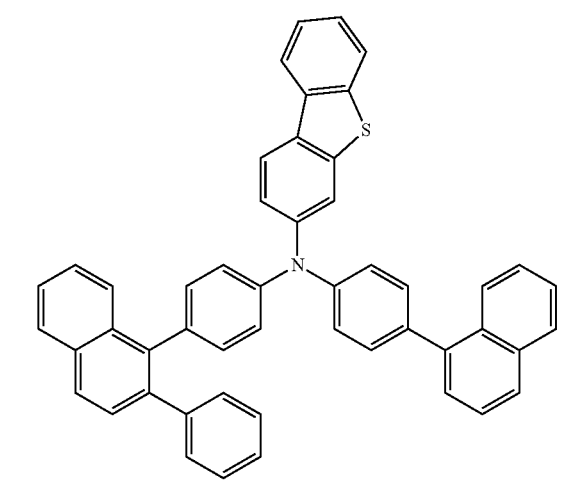
80
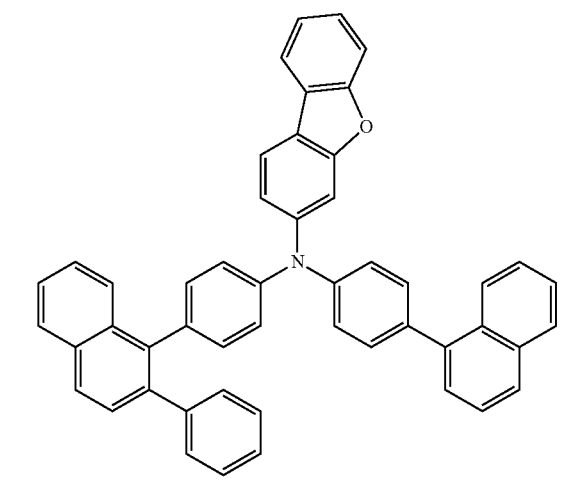
-continued
81
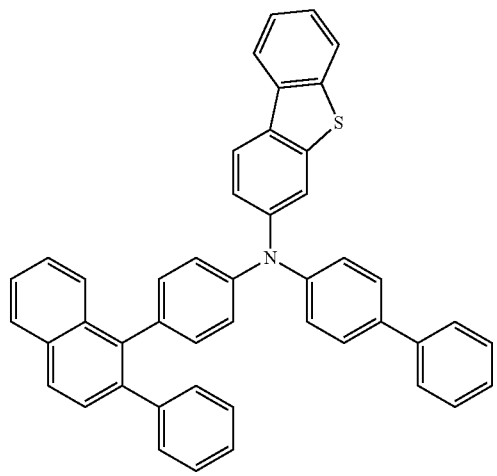
82
84
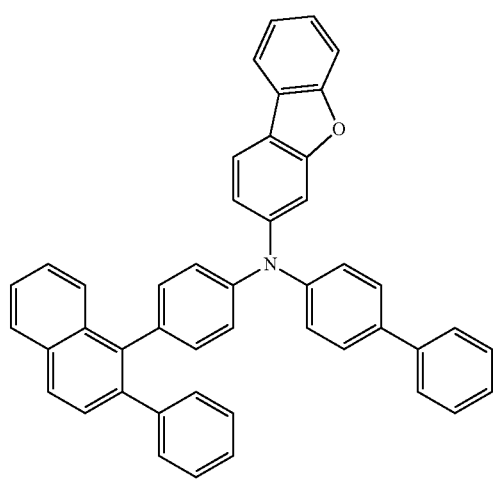

85
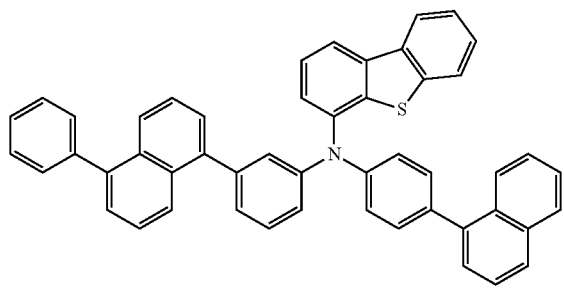
86
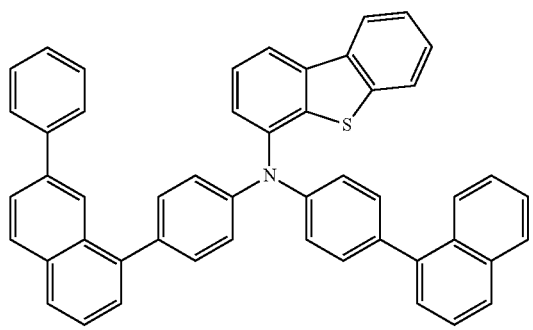
88
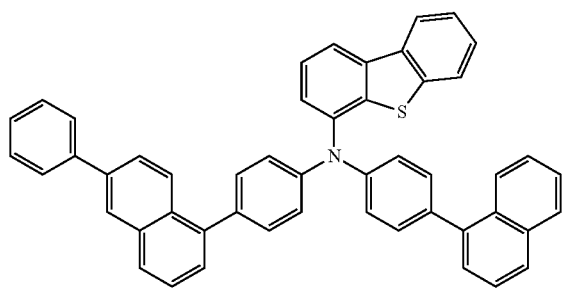
89
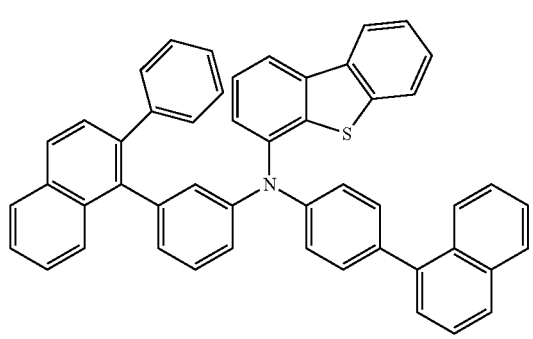
90
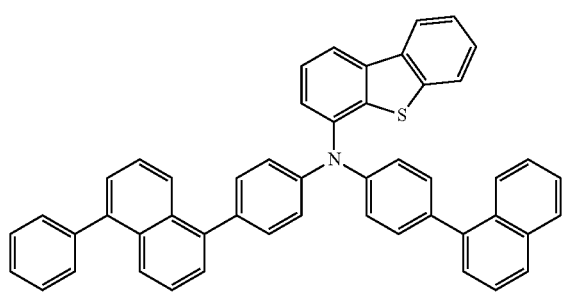
92
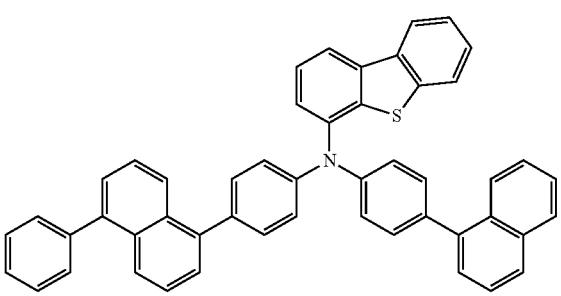
94
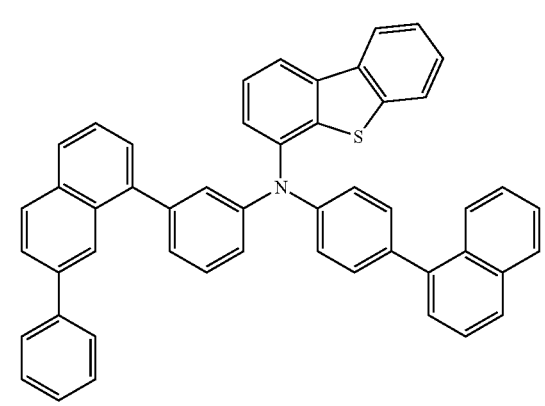
95
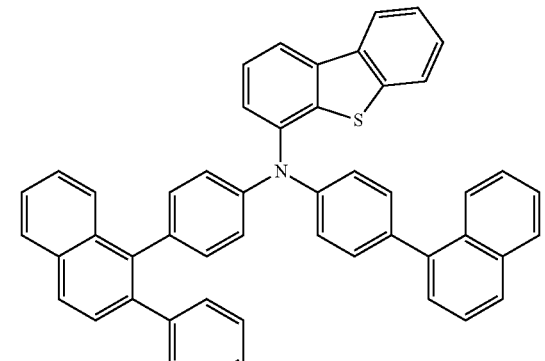
96
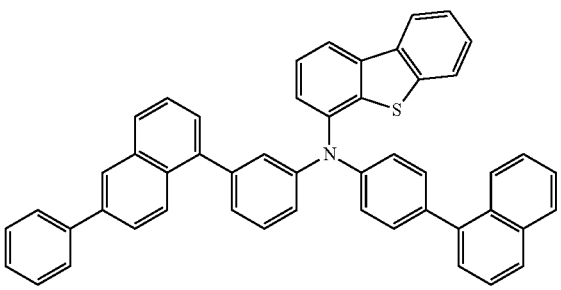

97
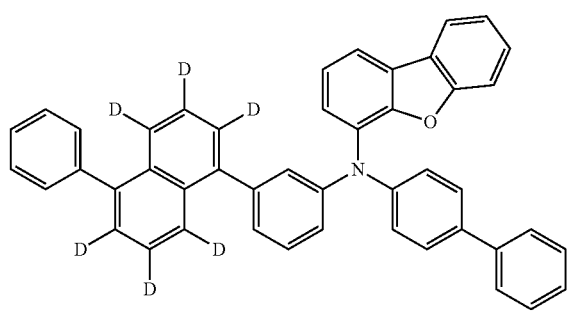
98
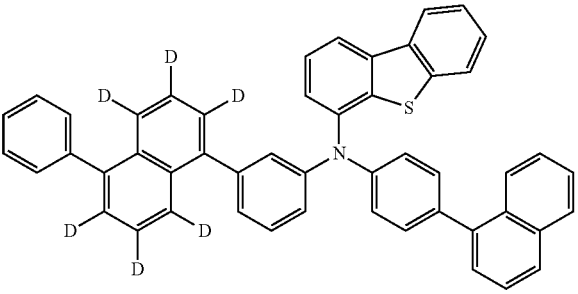
99
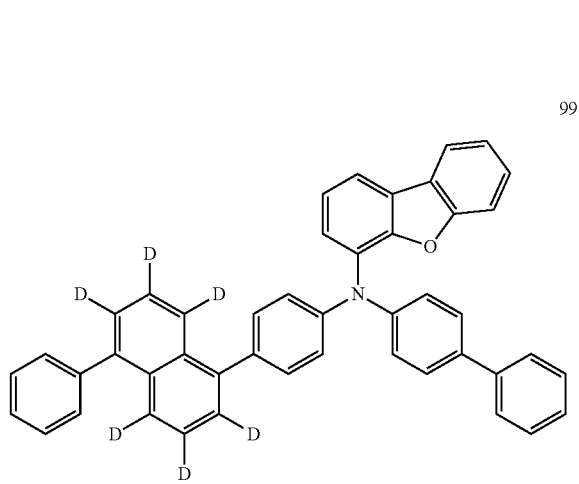
100
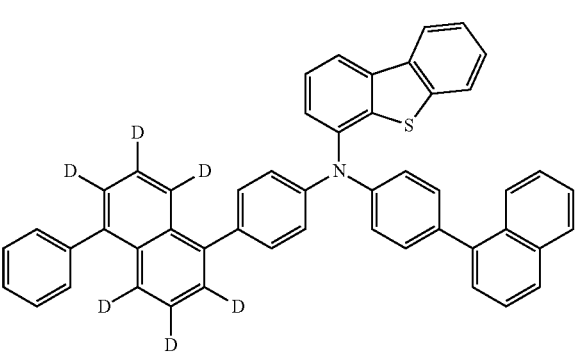
101
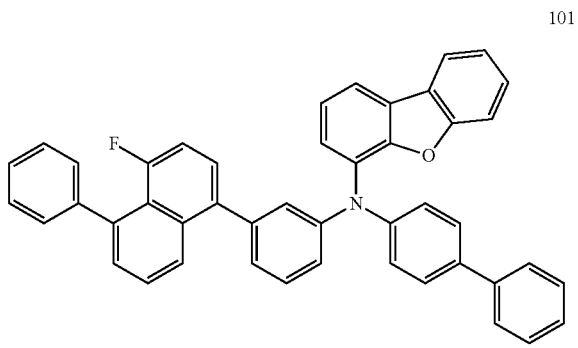
102
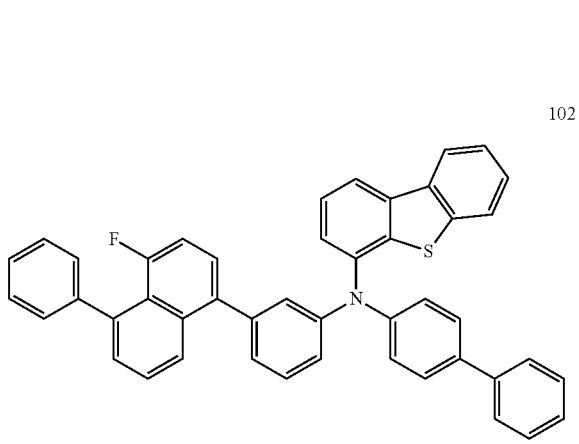
103
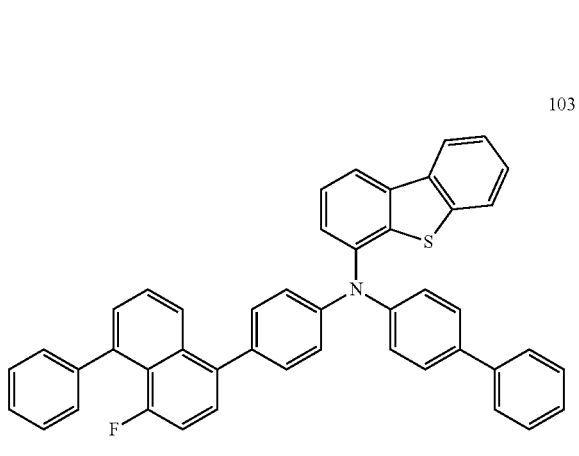
104
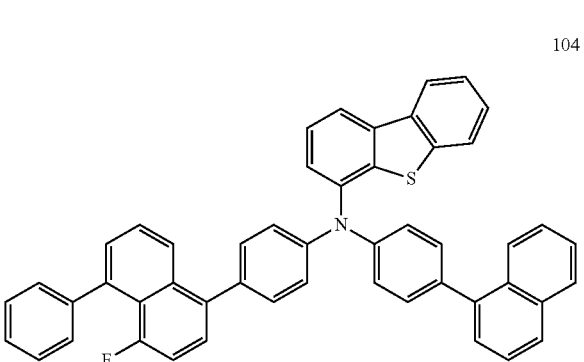

-continued
105
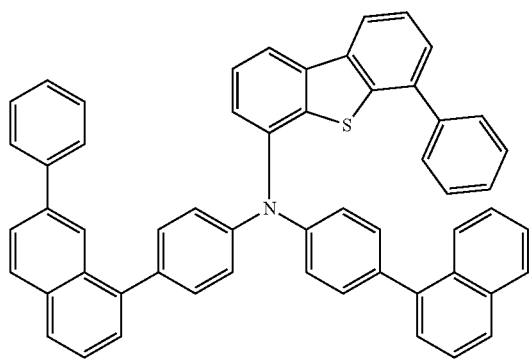
106
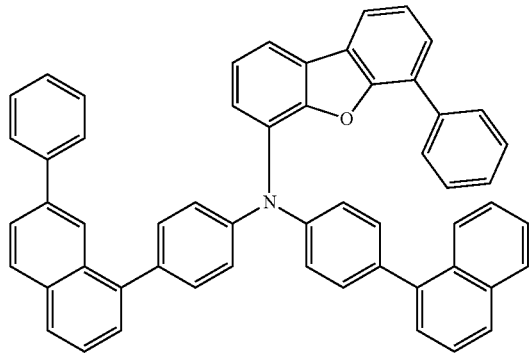
108
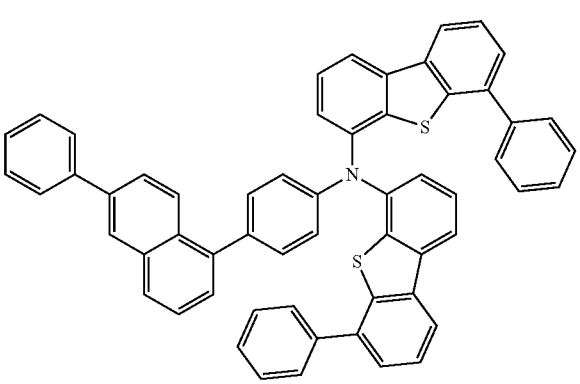
109
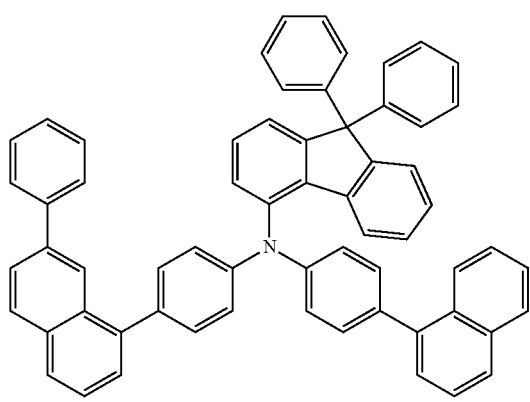
-continued
110
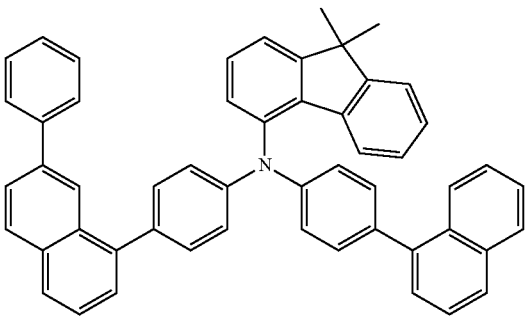
111
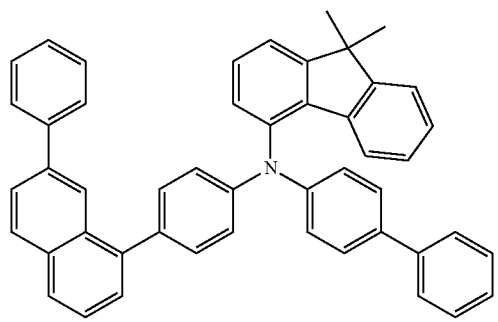
112
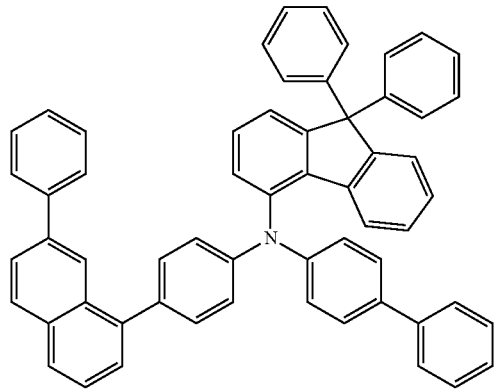
113
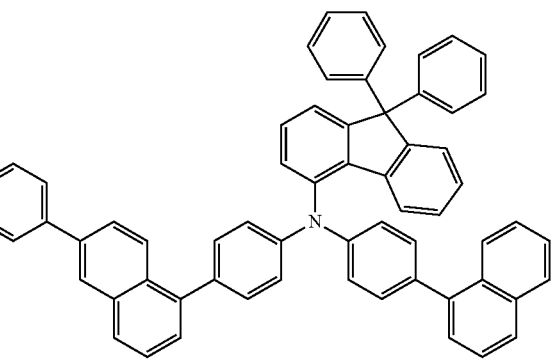

114
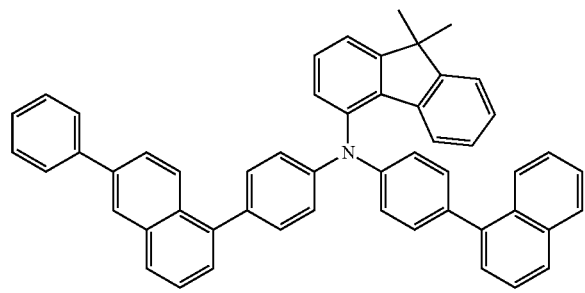
115
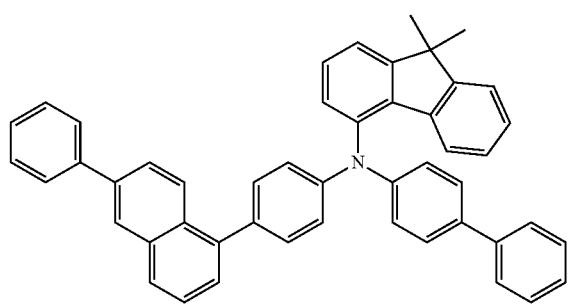
116
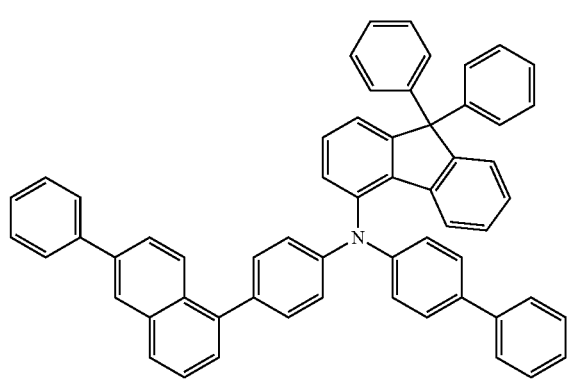
117
118
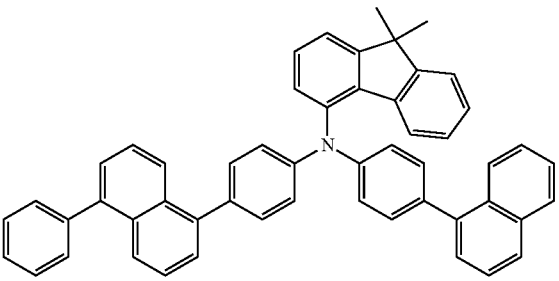
119
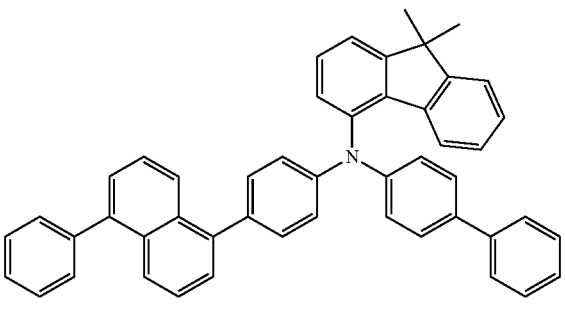
120
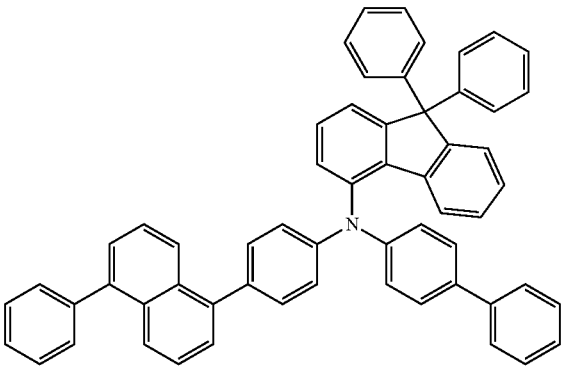
125
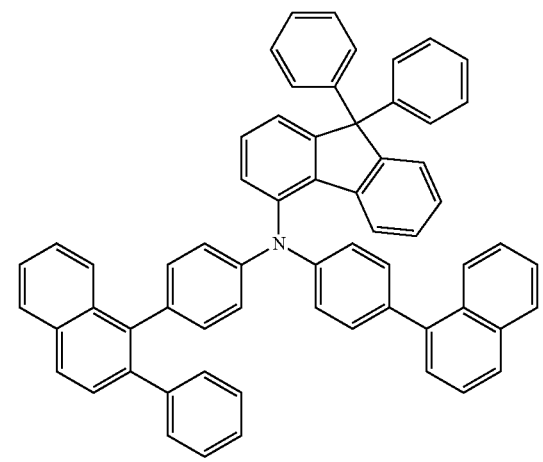

129
-continued
126
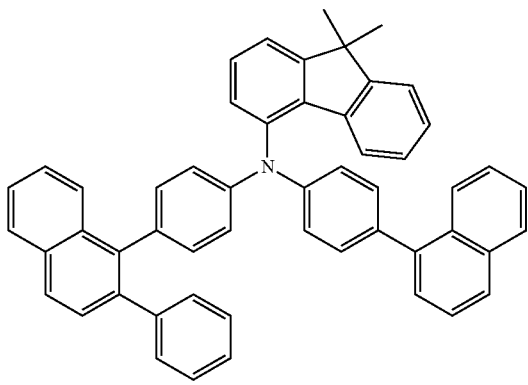
127
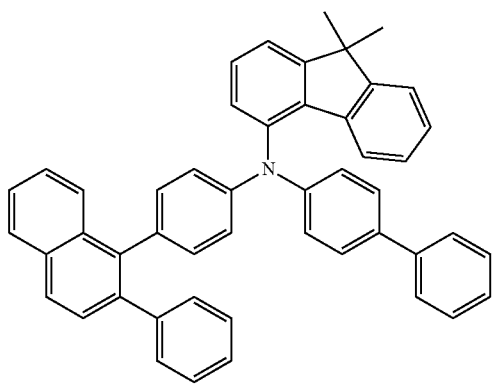
128
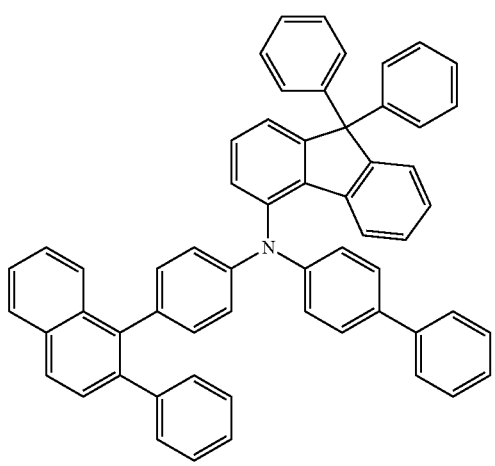
130
-continued
133
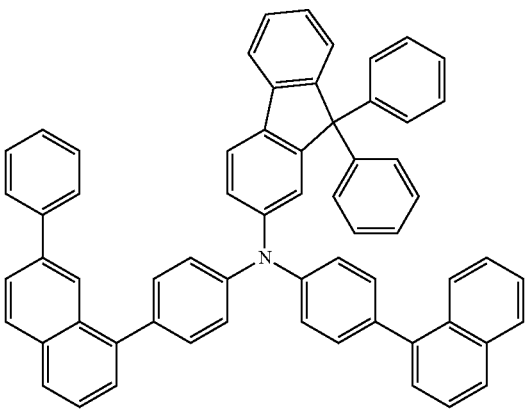
134
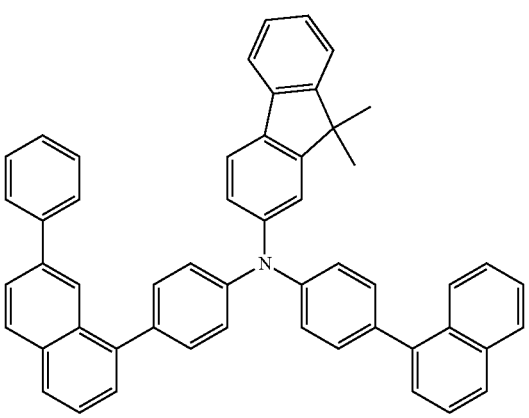
135
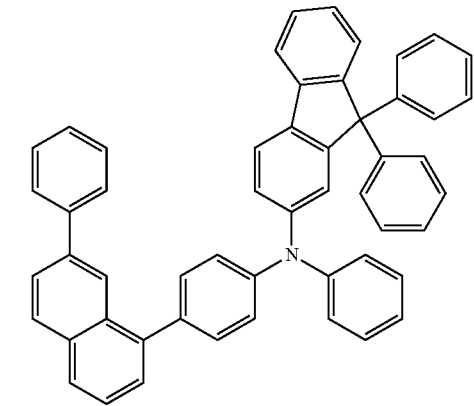

136
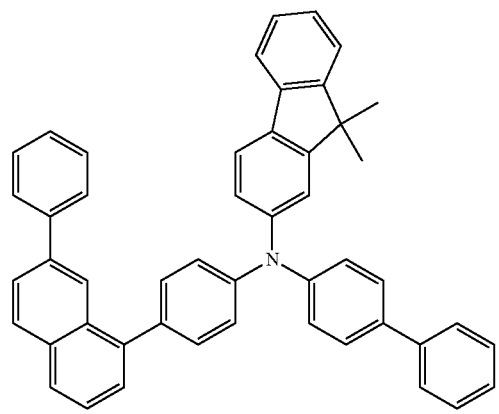
140
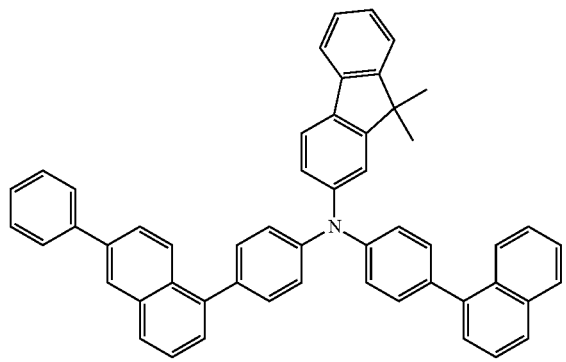
137
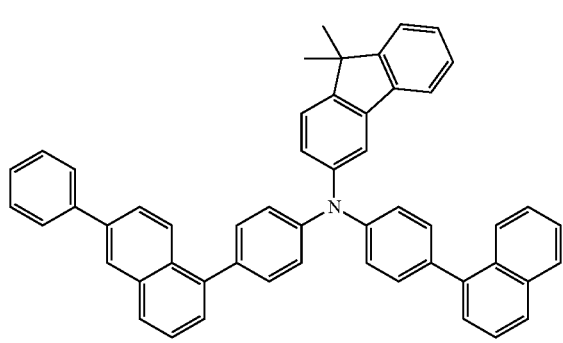
141
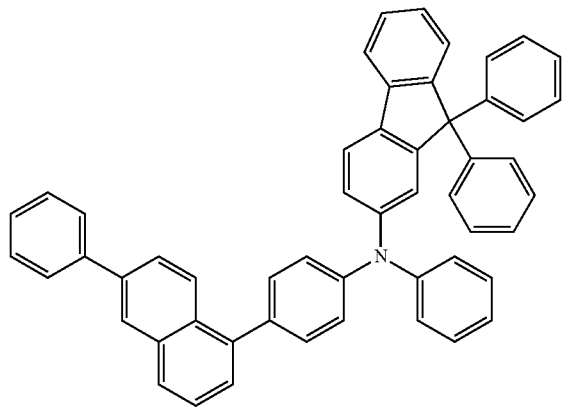
138
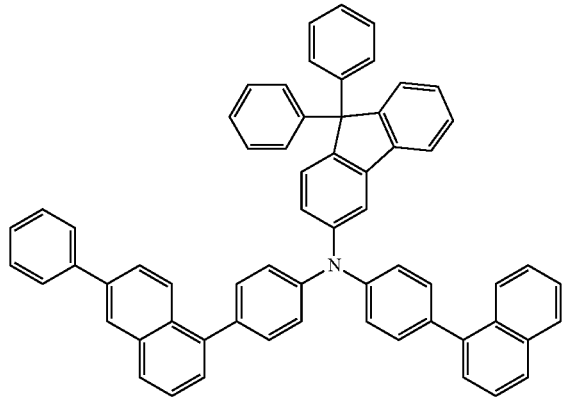
142
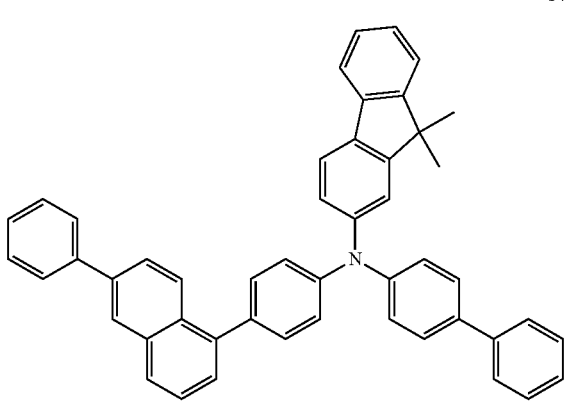
139
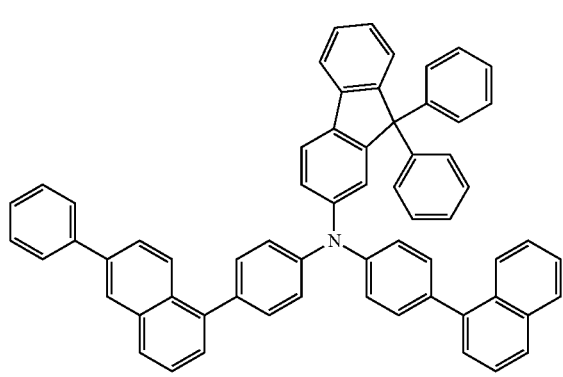
143
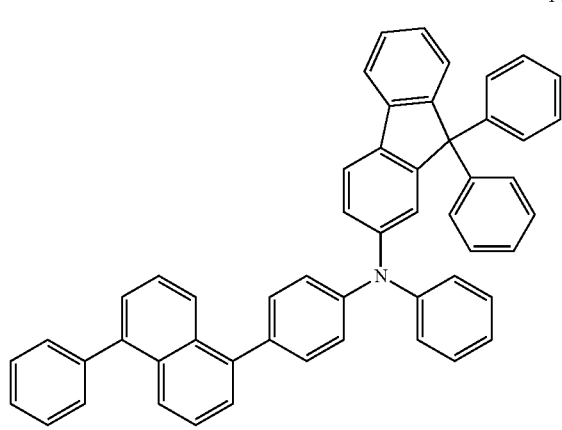

144
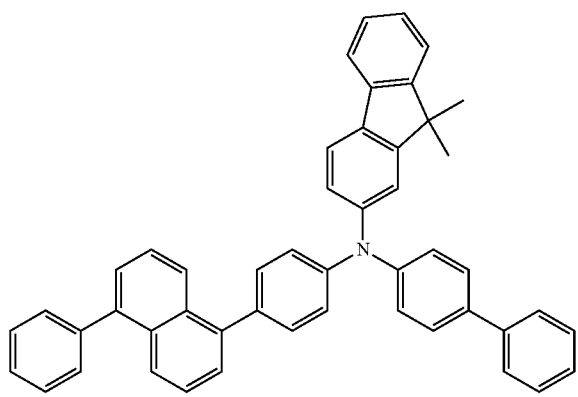
145
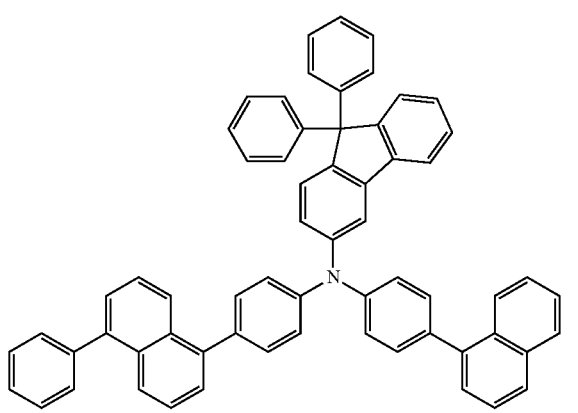
146
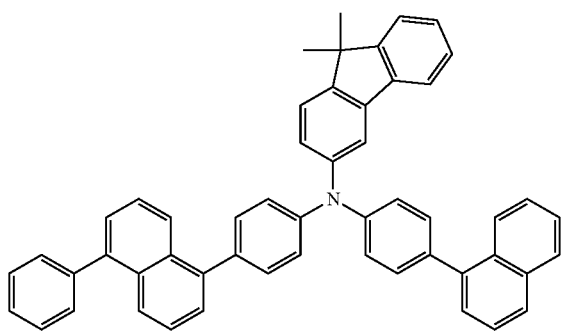
147
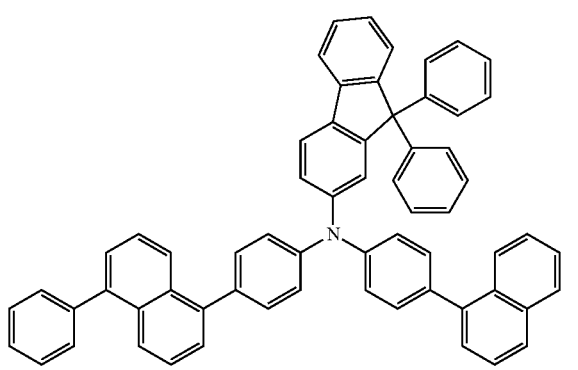
148
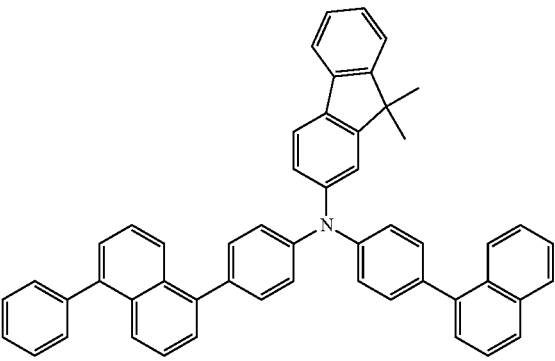
161
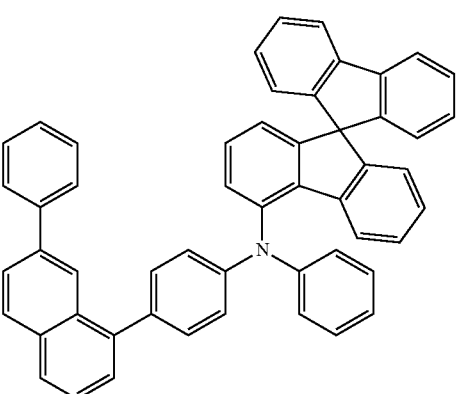
162
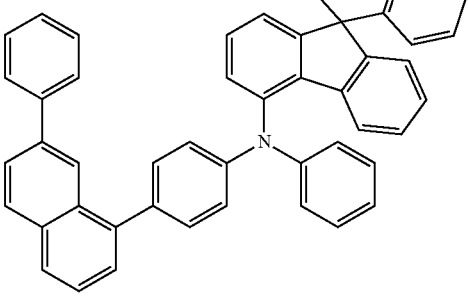
163
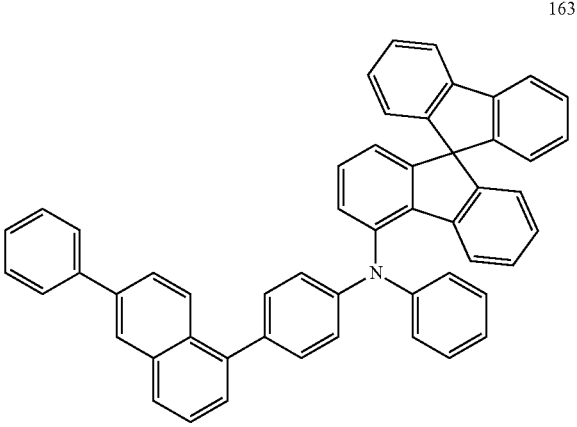

-continued
164
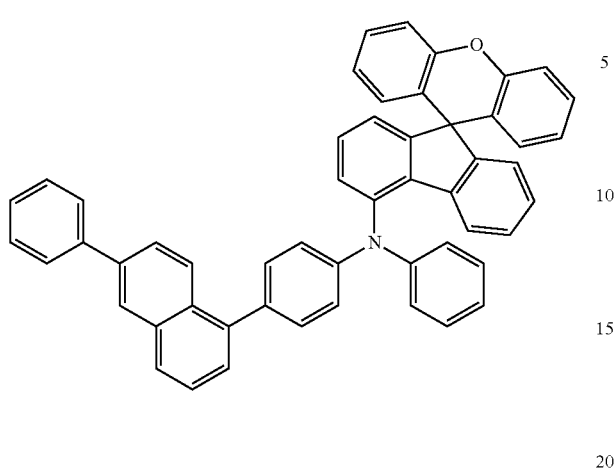
171
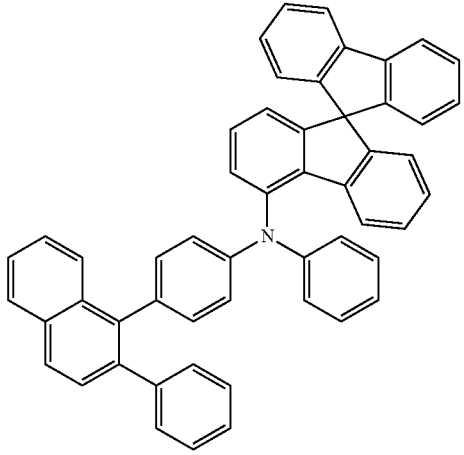
165
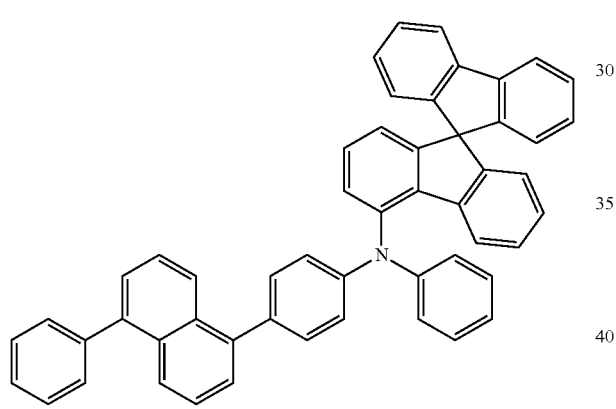
172
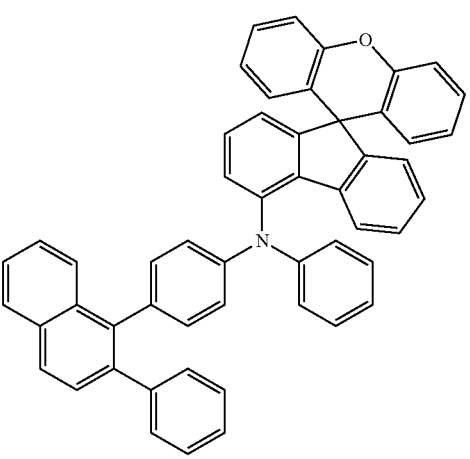
166
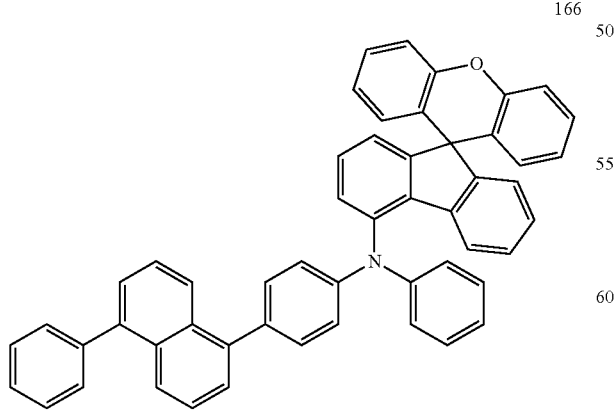
173
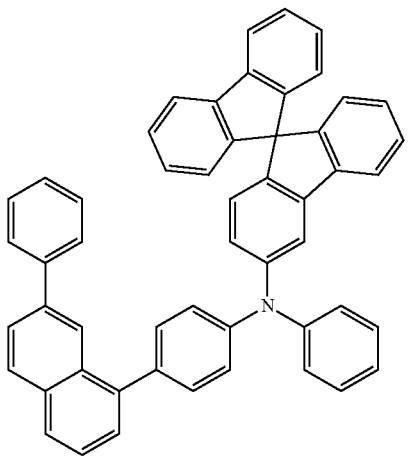

174
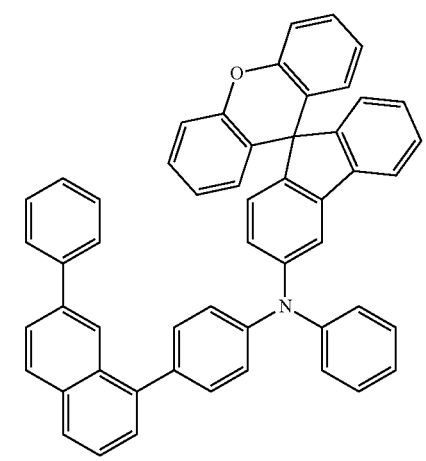
175
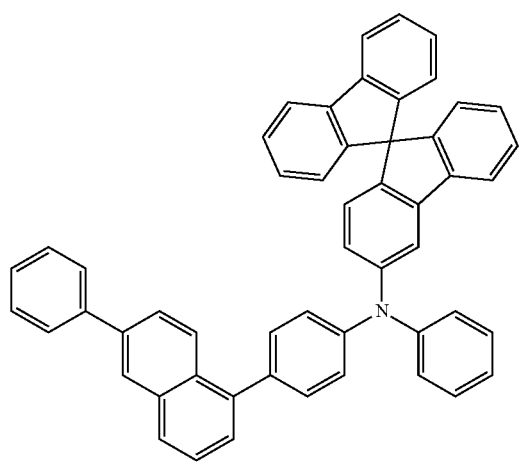
176
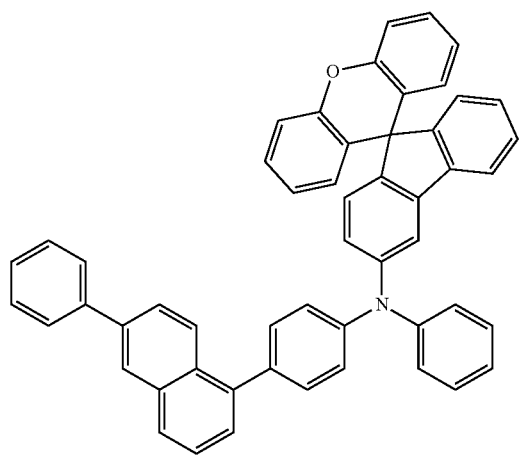
177
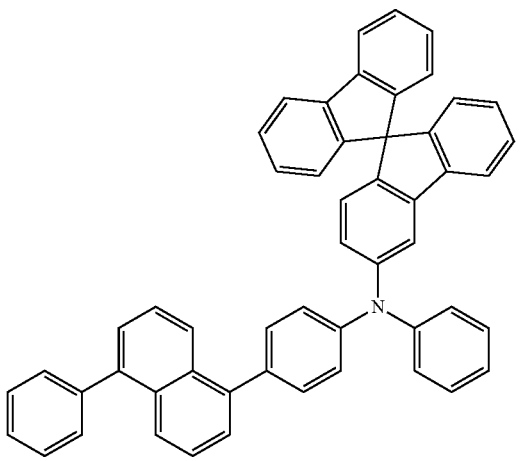
178
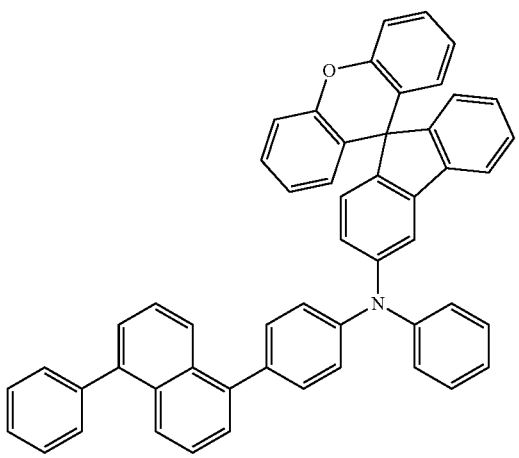
183
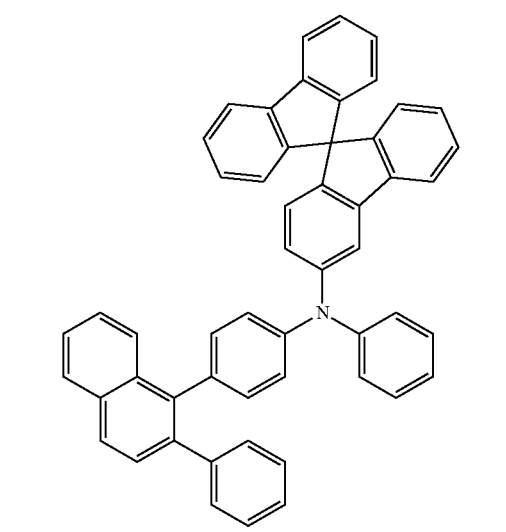

184
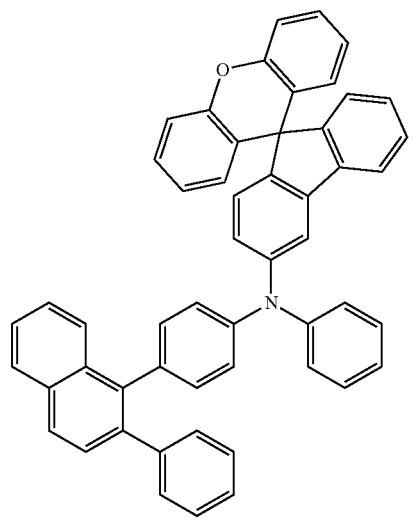
185
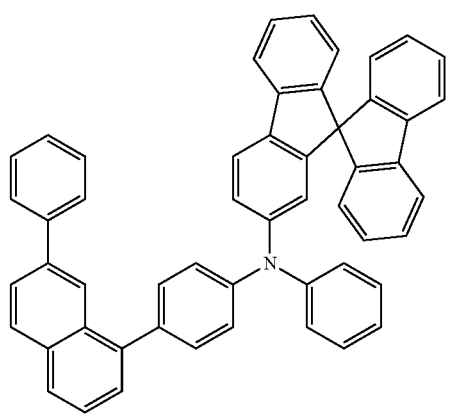
186
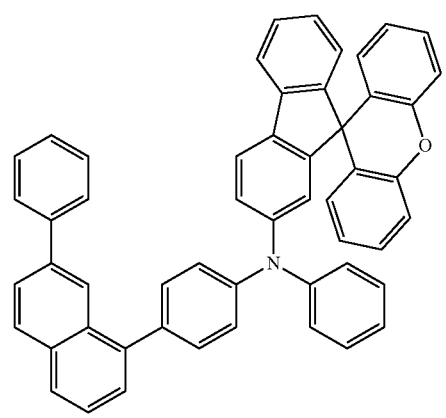
187
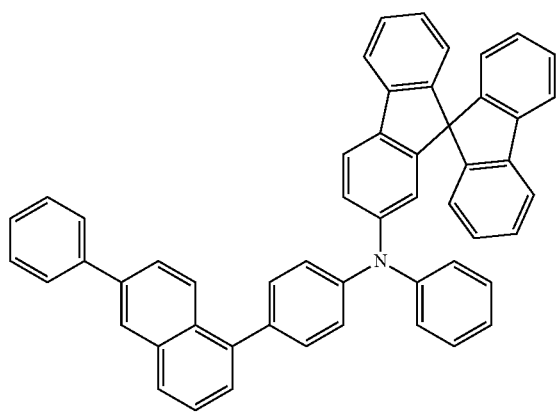
188
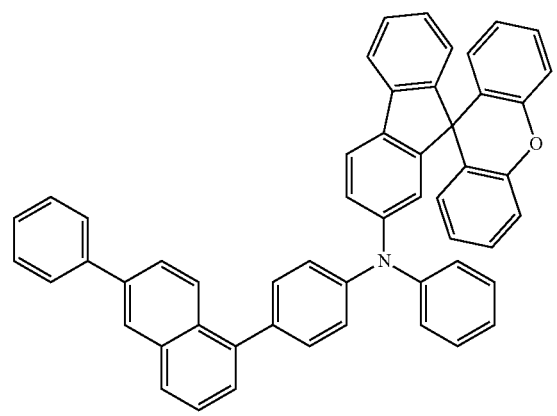
189
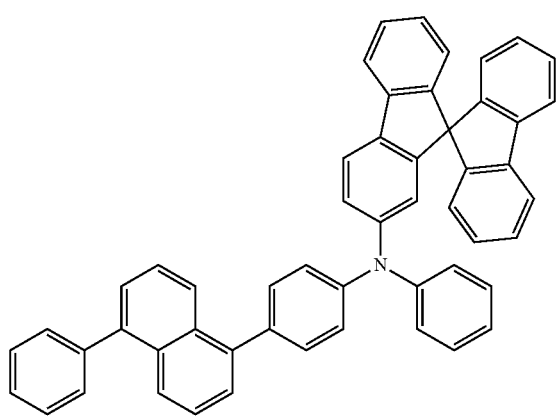

-continued
190
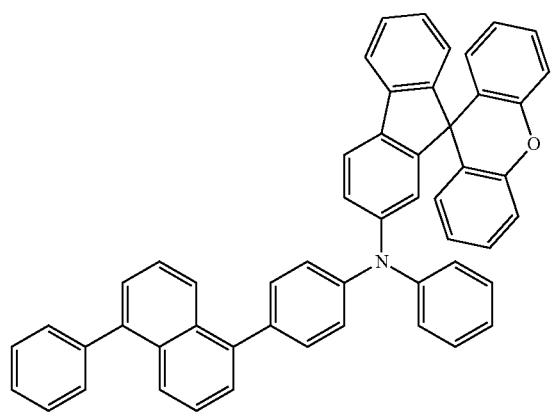
195
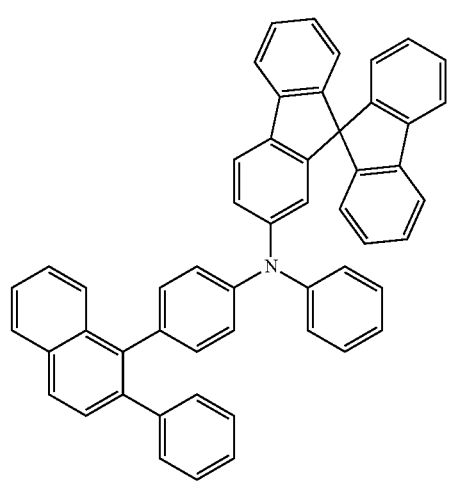
196
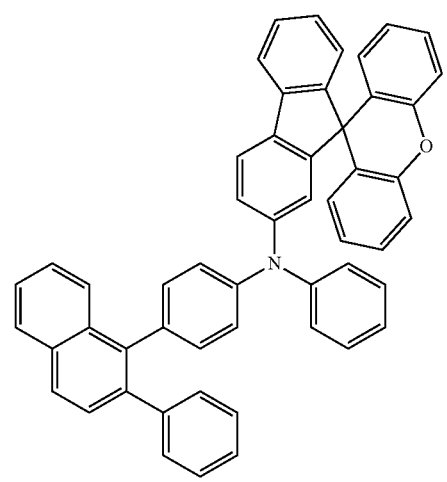
-continued
197
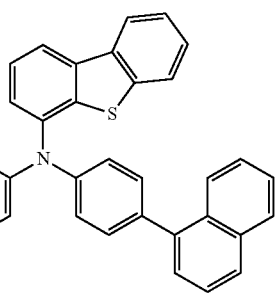
198
199
200

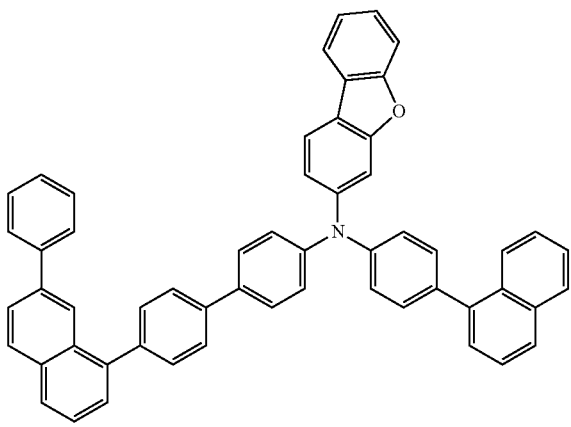

205

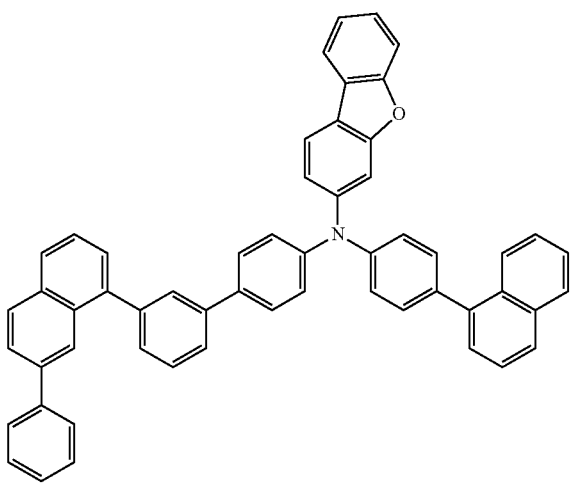

206

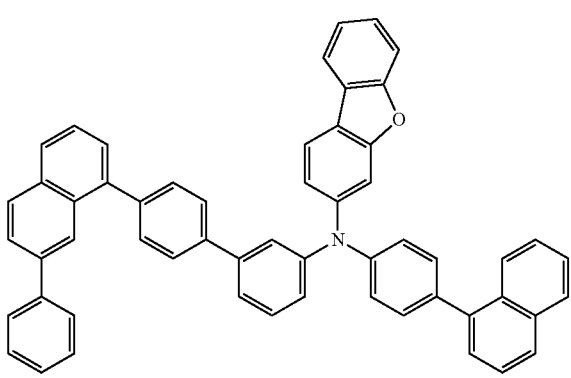

207

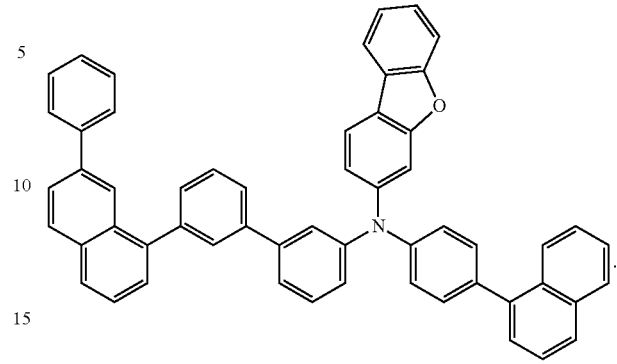

208

12. An organic electroluminescence device, comprising:
a first electrode;
a hole transport region on the first electrode;
an emission layer on the hole transport region;
an electron transport region on the emission layer; and
a second electrode on the electron transport region,
wherein the hole transport region comprises a monoamine compound represented by Formula 1:

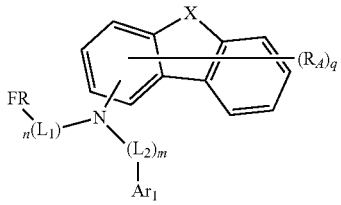

[Formula 1]

wherein in Formula 1,

X is CRR',

R and R' are each independently a substituted or unsubstituted aryl group having 6 to 20 ring carbon atoms, or a substituted or unsubstituted heteroaryl group having 2 to 10 ring carbon atoms, and are separate or form a ring by combining adjacent groups with each other, $L_1$ is an unsubstituted arylene group having 6 to 12 carbon atoms for forming a ring, or an unsubstituted heteroarylene group having 2 to 12 carbon atoms for forming a ring, $L_2$ is a direct linkage, a substituted or unsubstituted arylene group having 6 to 12 ring carbon atoms, or a substituted or unsubstituted heteroarylene group having 2 to 12 ring carbon atoms, m is an integer of 0 to 2, n is 1 or 2, $R_A$ is a hydrogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, q is an integer of 0 to 7, $Ar_1$ is a substituted or unsubstituted aryl group having 6 to 12 ring carbon atoms, and FR is represented by Formula 2:

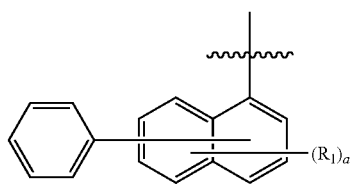

[Formula 2]

wherein in Formula 2,
$R_1$ is a hydrogen atom, a deuterium atom, or a halogen atom, and
a is an integer of 0 to 6.

13. The organic electroluminescence device as claimed in claim 12, wherein FR is represented by Formula 2-1:

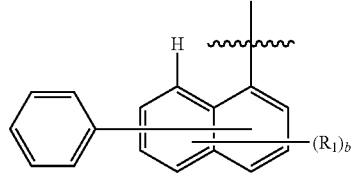

[Formula 2-1]

wherein in Formula 2-1,
b is an integer of 0 to 5, and $R_1$ is the same as defined in Formula 2.

14. The organic electroluminescence device as claimed in claim 12, wherein n is 1, and $L_1$ is a substituted or unsubstituted arylene group having 6 to 12 ring carbon atoms.

15. The organic electroluminescence device as claimed in claim 12, wherein $L_1$ is a substituted or unsubstituted phenylene group.

16. The organic electroluminescence device as claimed in claim 12, wherein m is 1, $L_2$ is a substituted or unsubstituted arylene group having 6 to 12 ring carbon atoms, and $Ar_1$ is a substituted or unsubstituted aryl group having 6 to 12 ring carbon atoms.

17. The organic electroluminescence device as claimed in claim 12, wherein the monoamine compound represented by Formula 1 is selected from Compound Group 1:

[Compound Group 1]

108

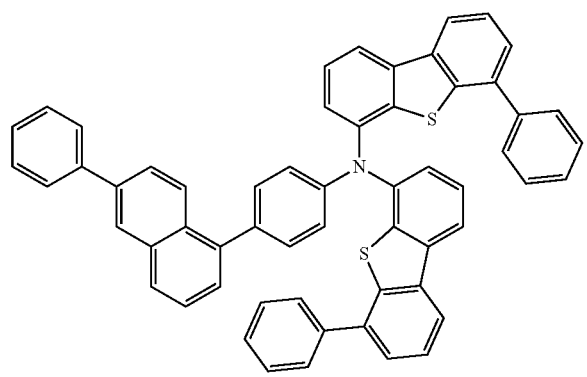

109

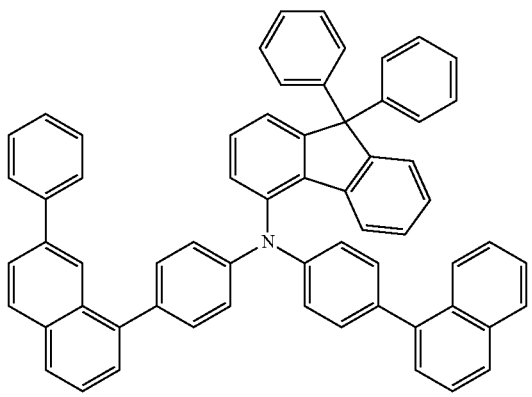

110

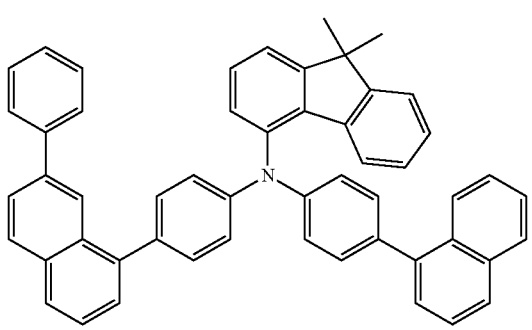

111

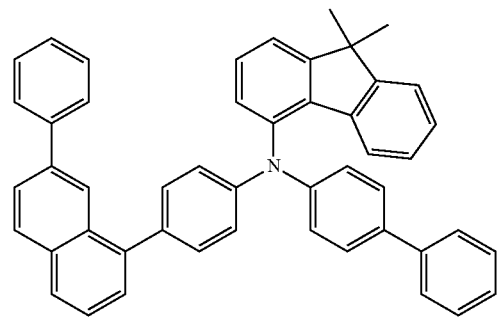

112

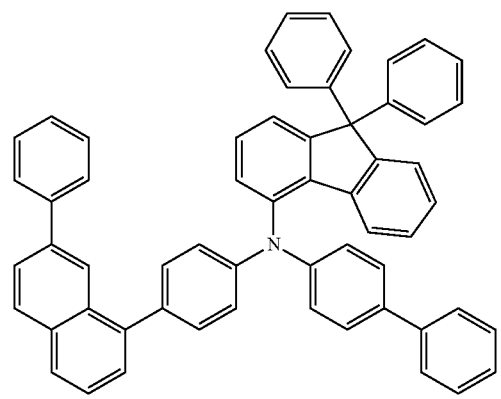

113
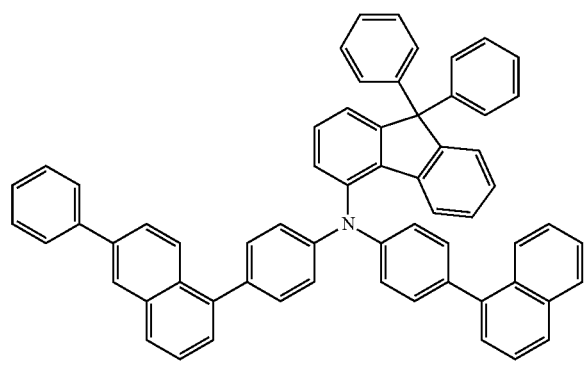
114
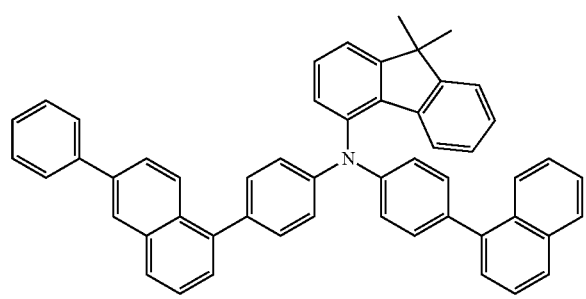
115
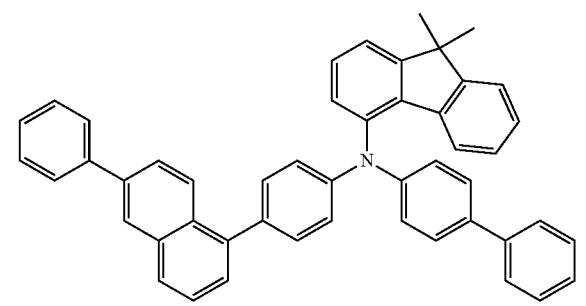
116
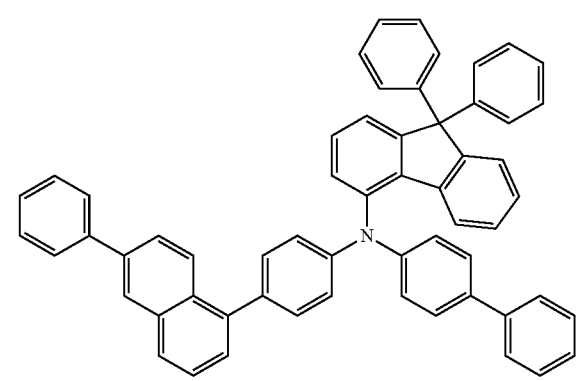
117
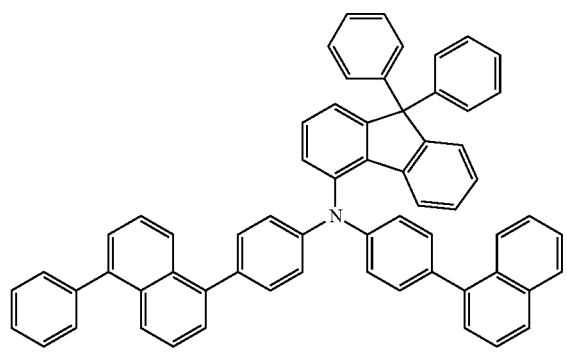
118
119
120
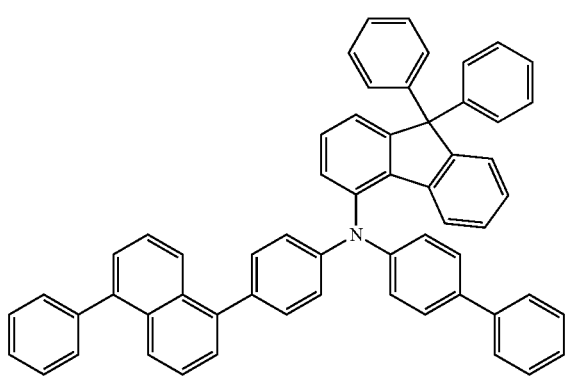

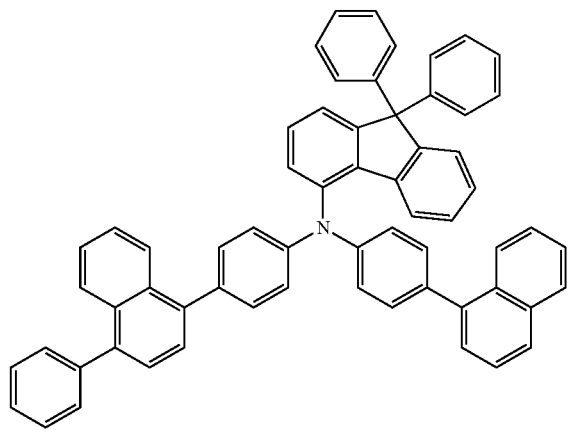
121
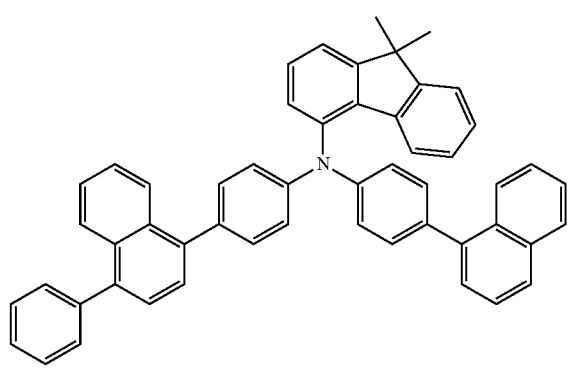
122
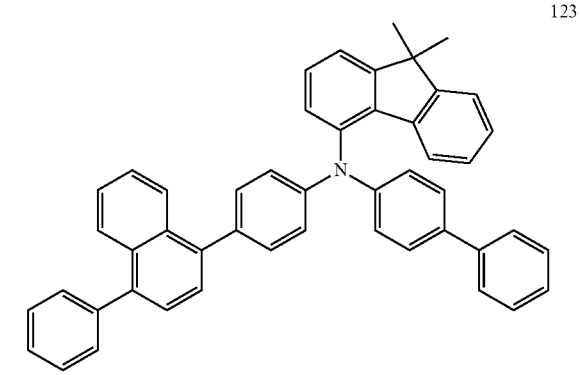
123
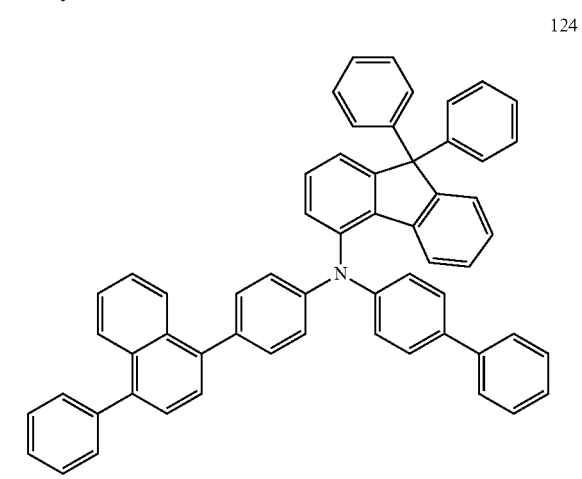
124
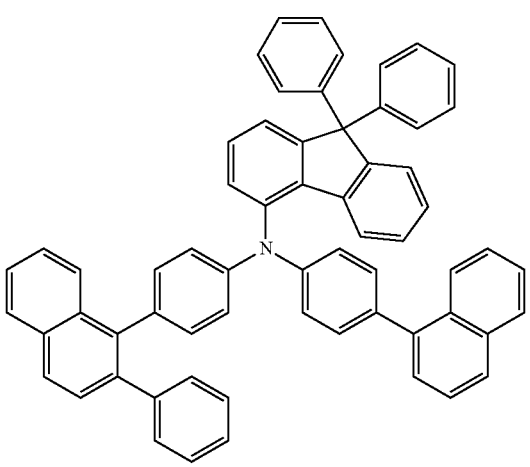
125
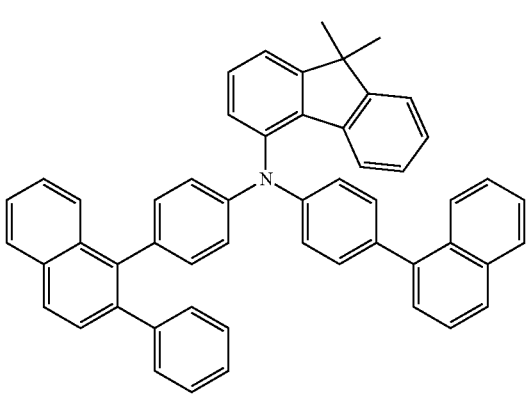
126
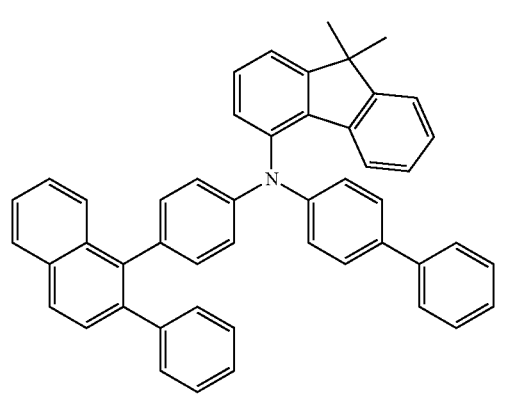
127

-continued
128
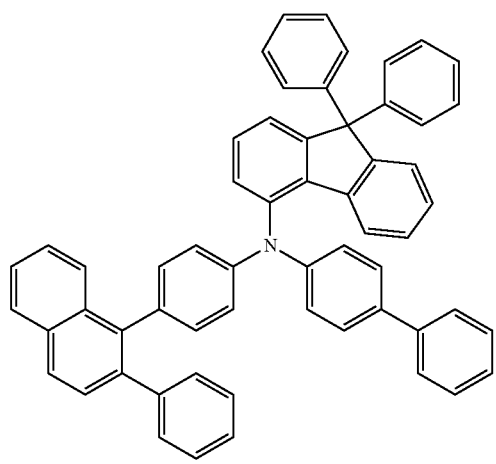
129
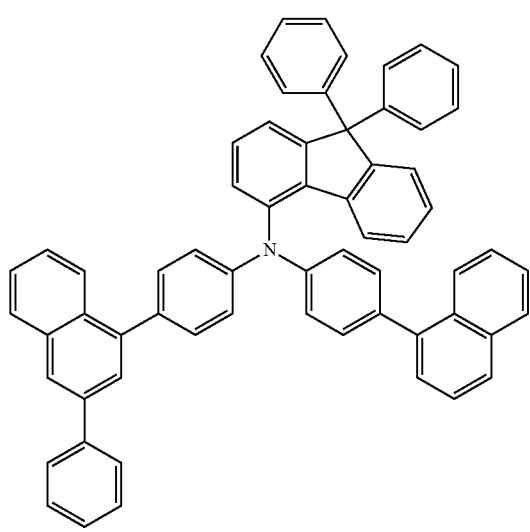
130
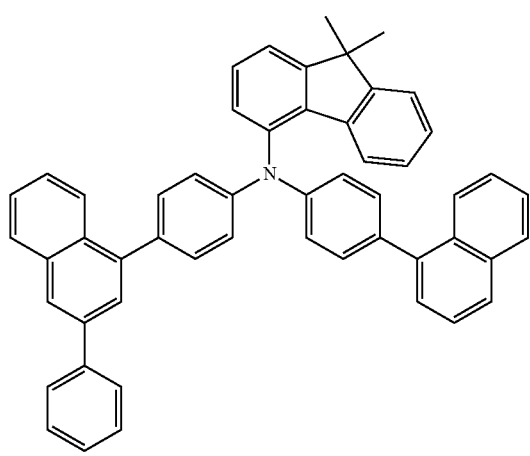
-continued
131
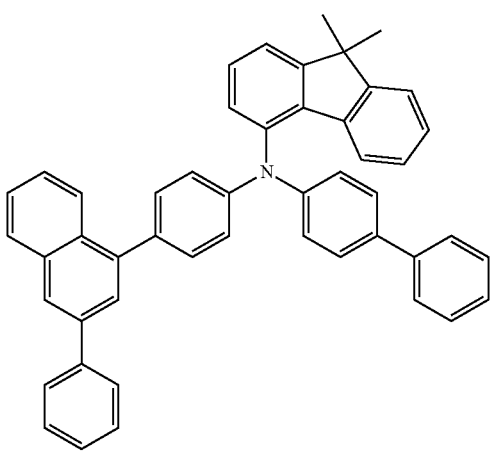
132
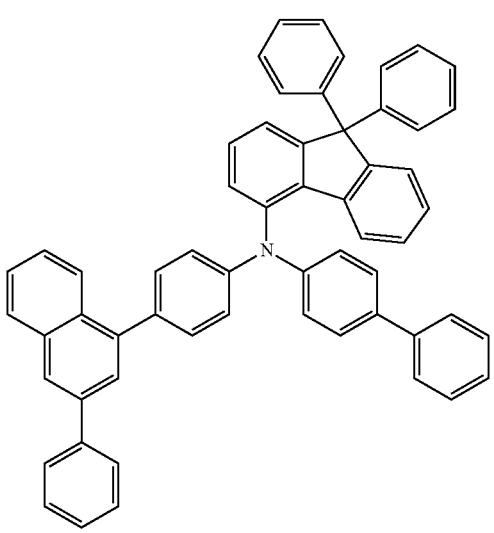
133
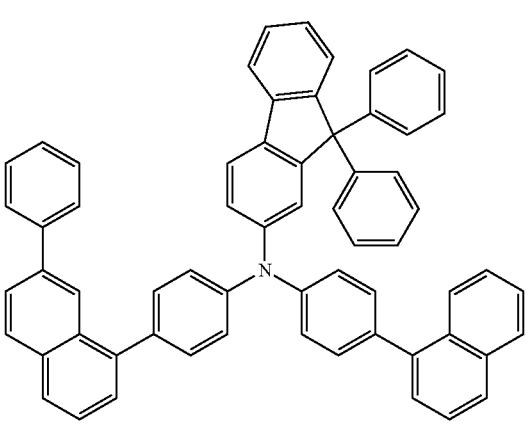

134
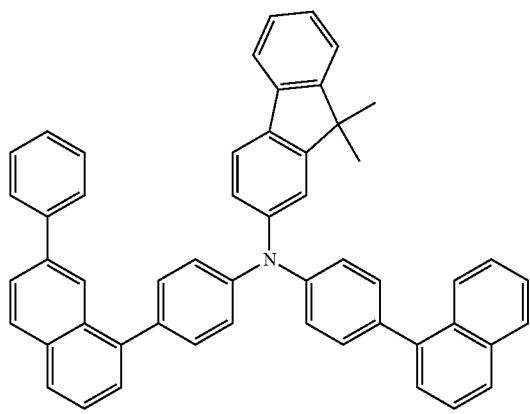
135
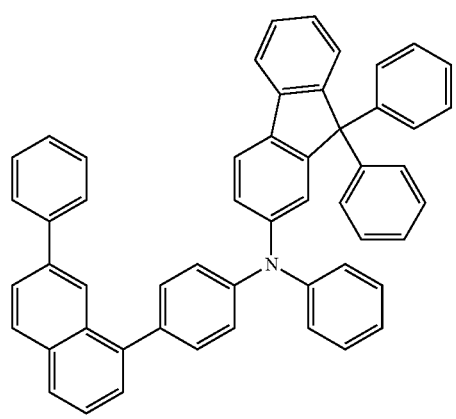
136
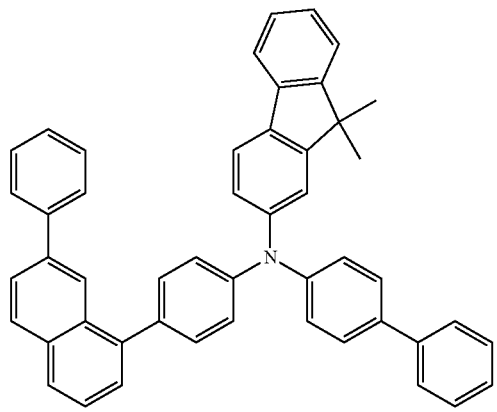
137
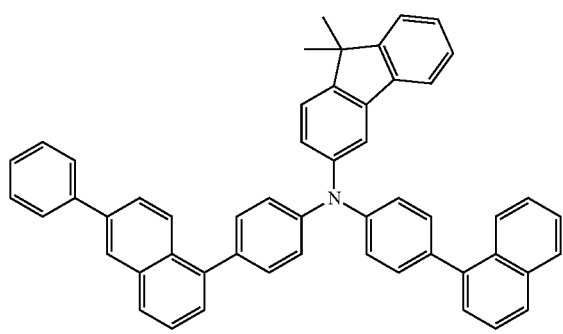
138
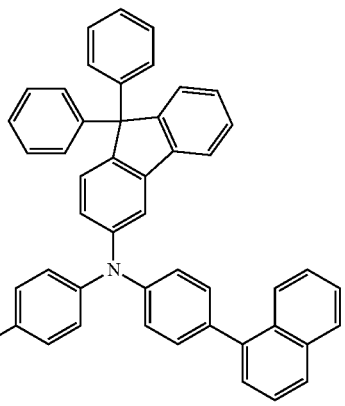
139
140
141
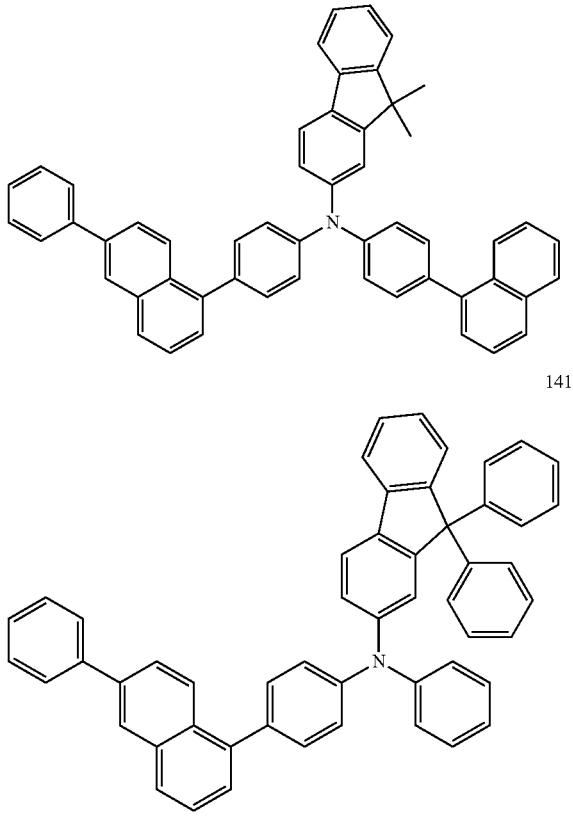

142
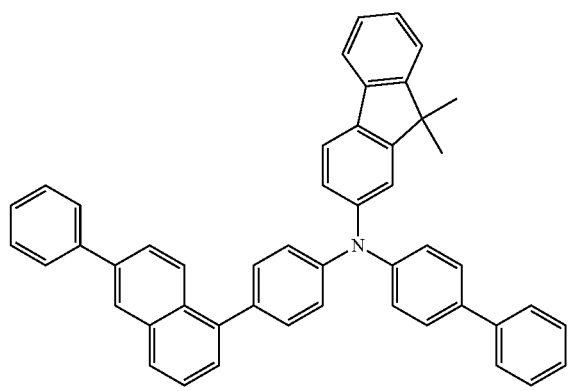
143
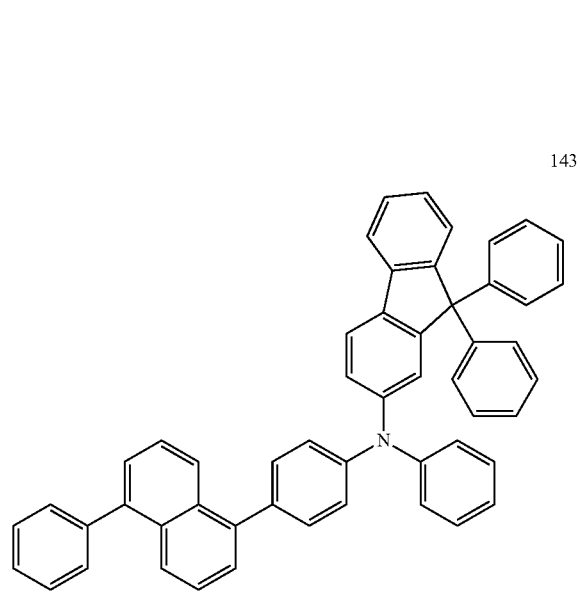
144
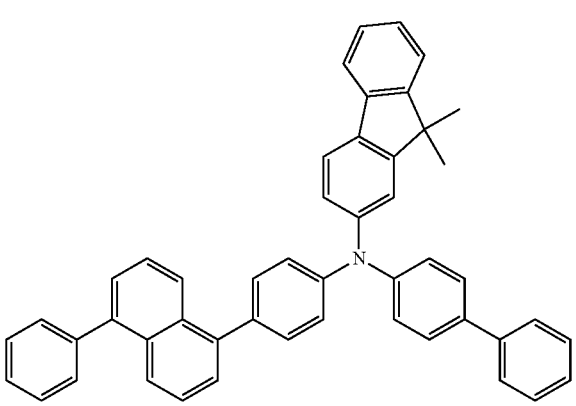
145
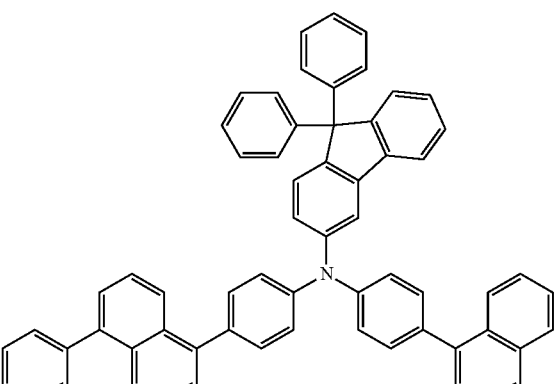
146
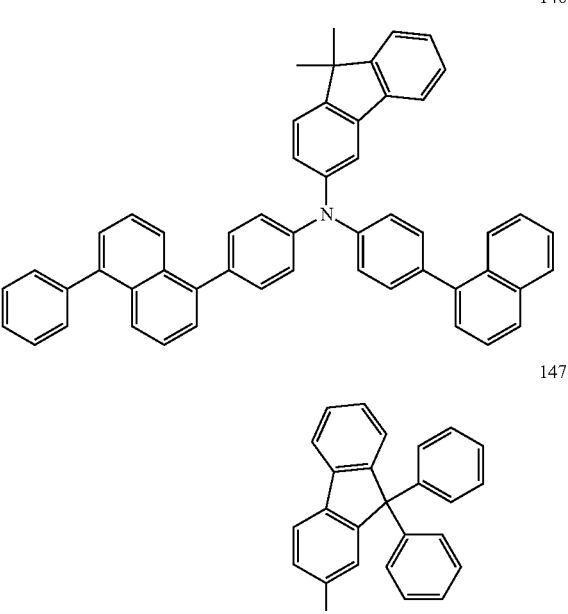
147
148
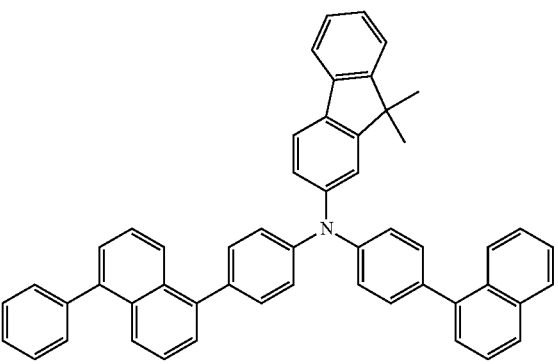

-continued
149
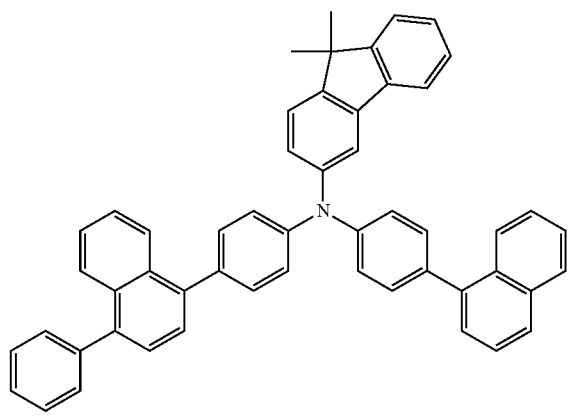
150
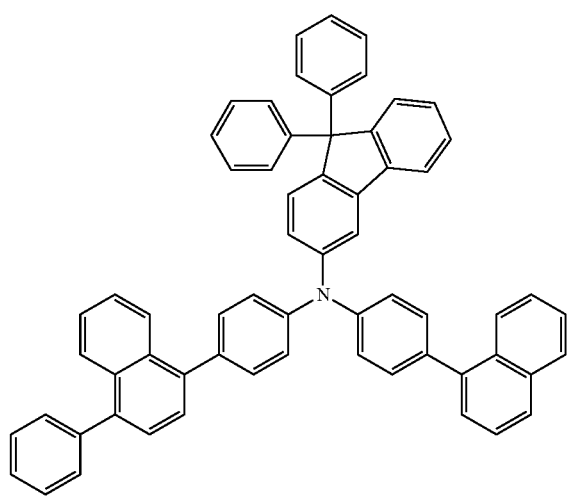
151
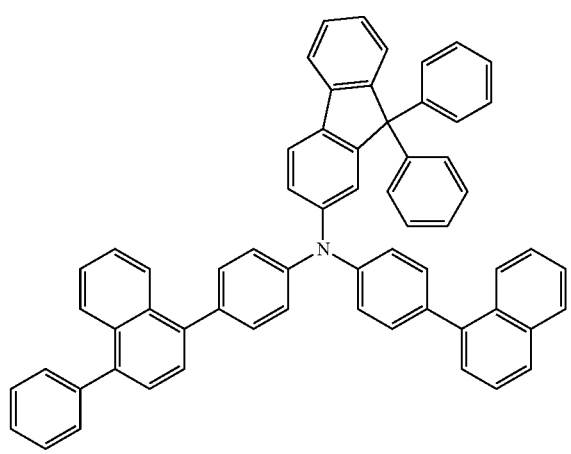
-continued
152
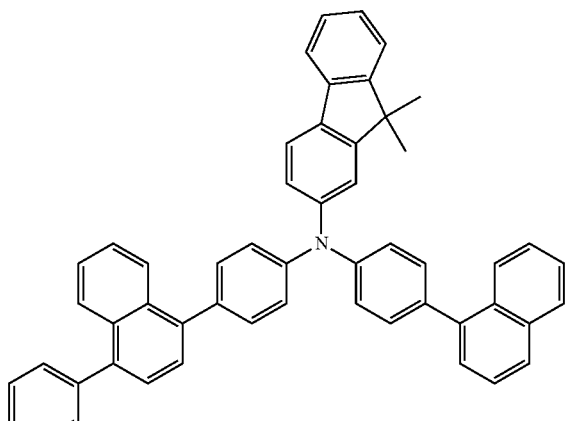
153
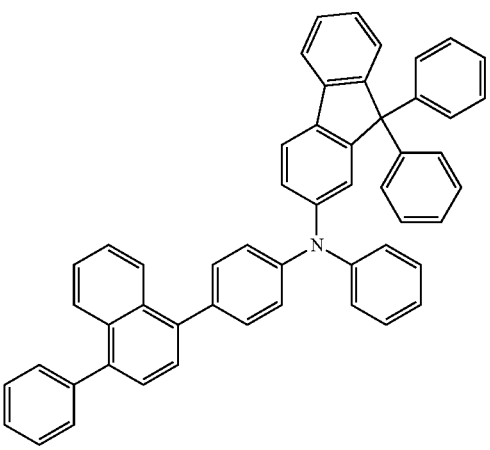
154
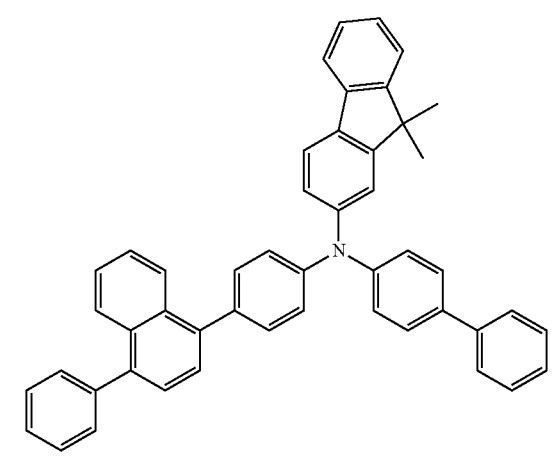

155
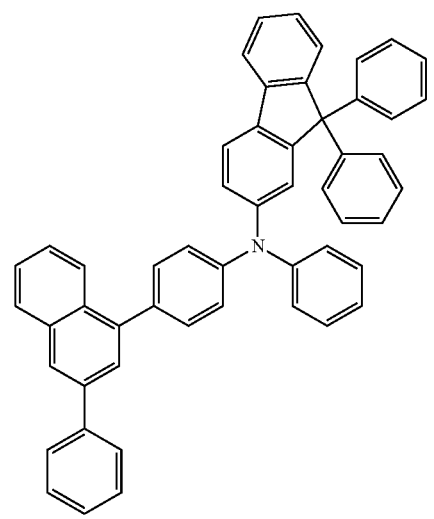
156
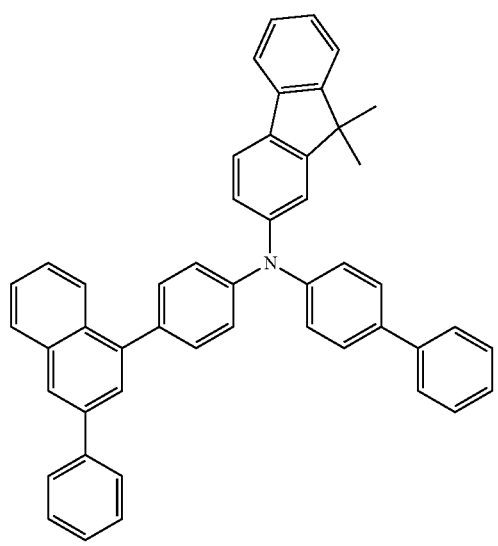
157
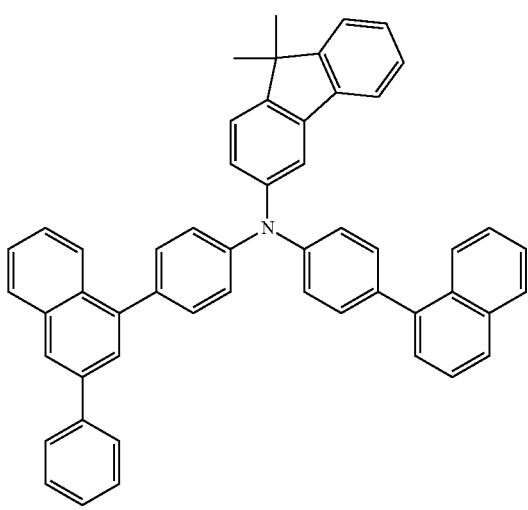
158
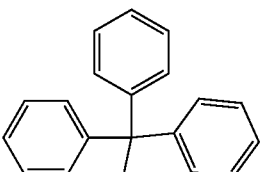
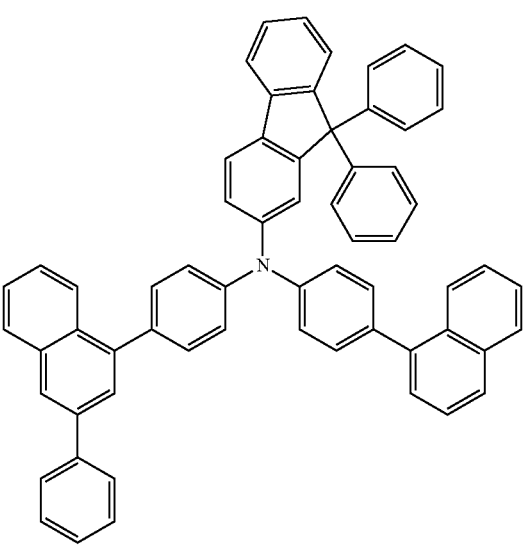
159

-continued
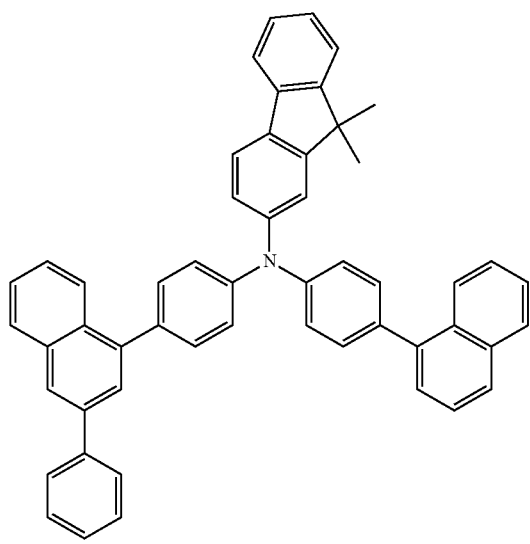
160
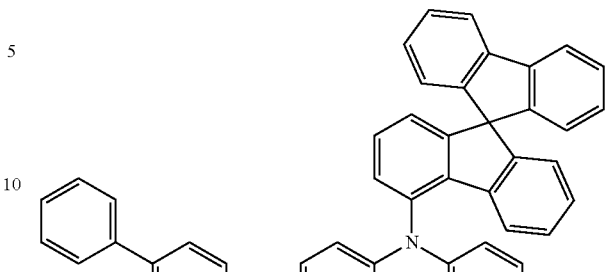
163
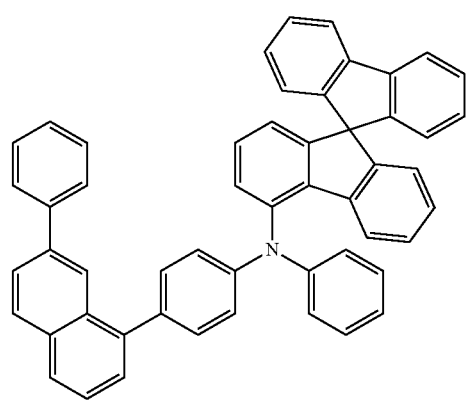
161
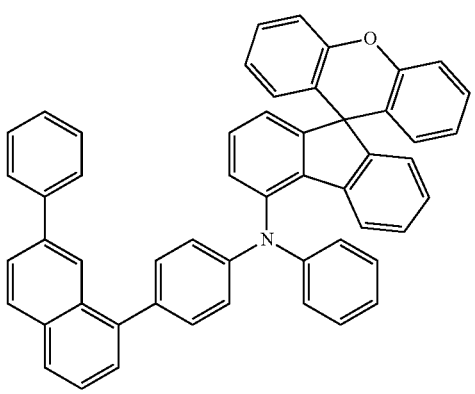
162
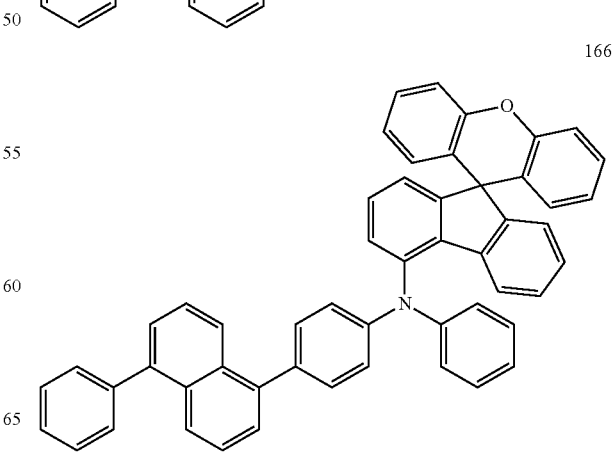

167
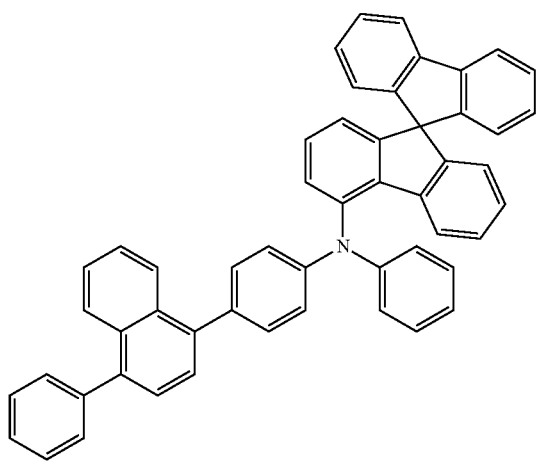
168
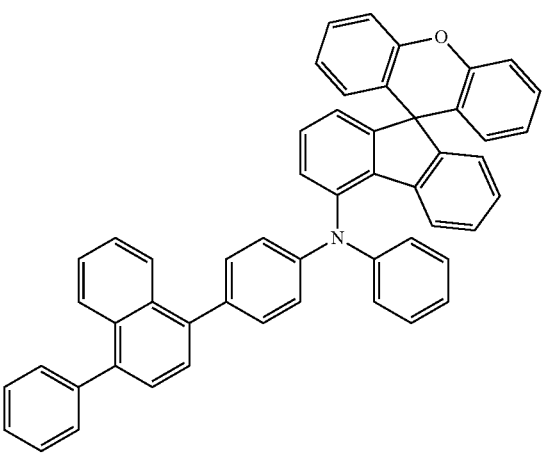
169
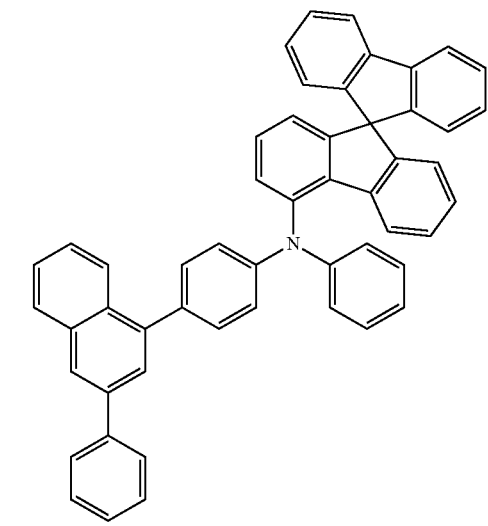
170
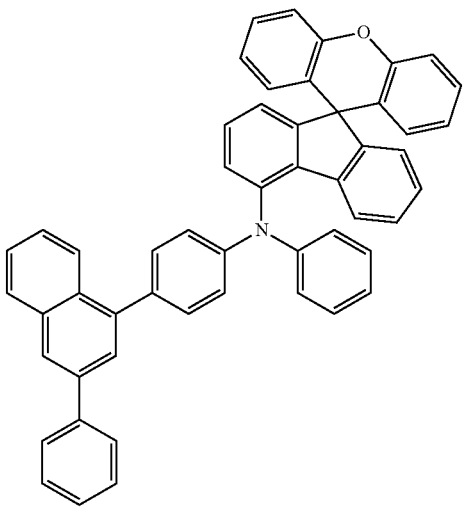
171
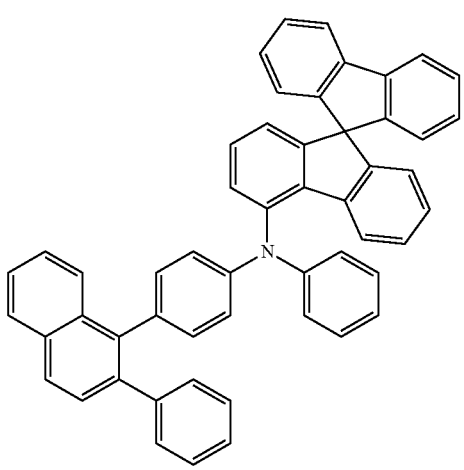
172
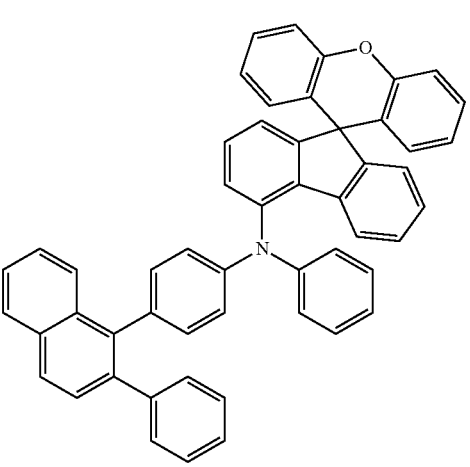

-continued
173
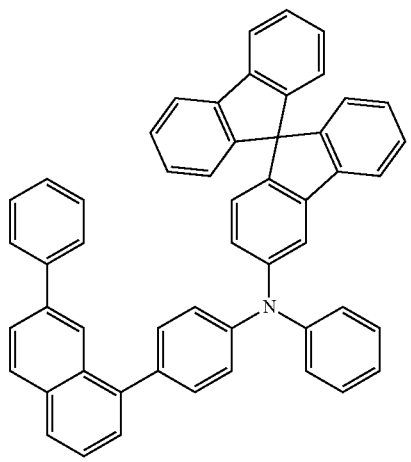
174
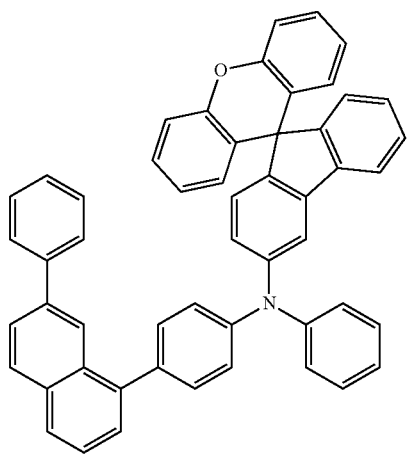
175
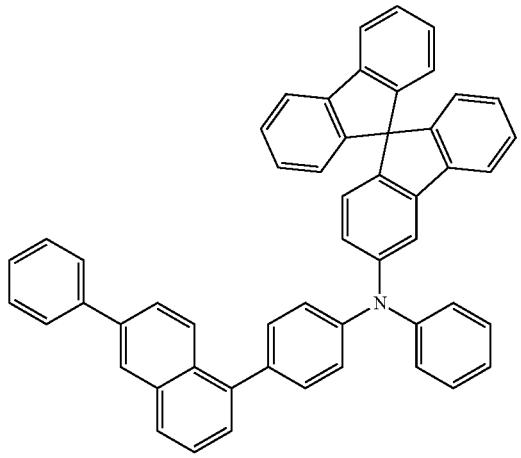
-continued
176
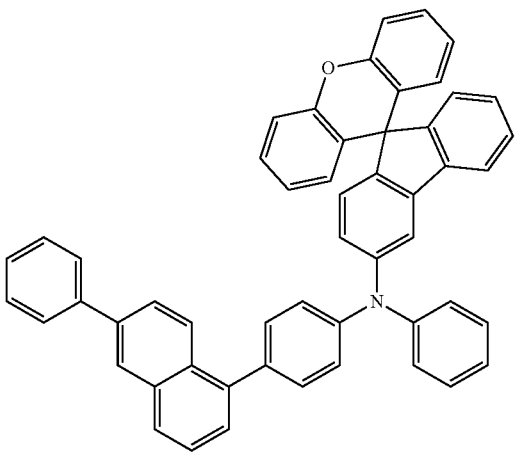
177
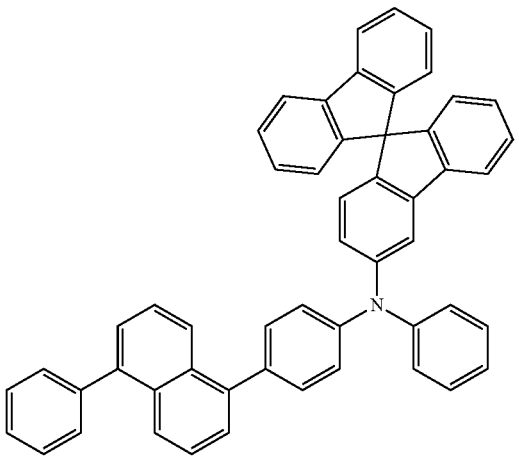
178
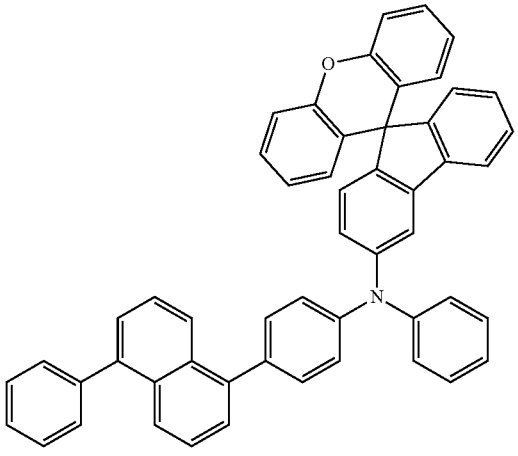

-continued
179
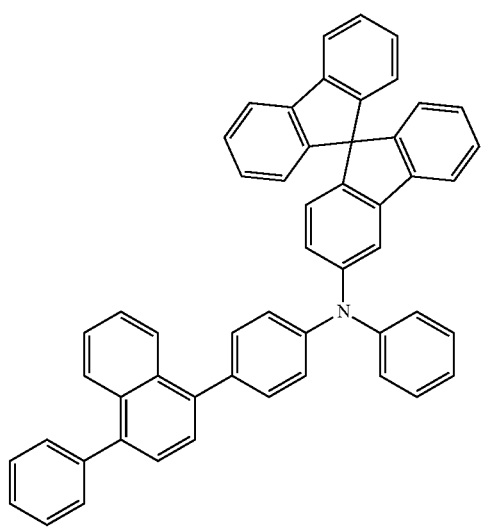
180
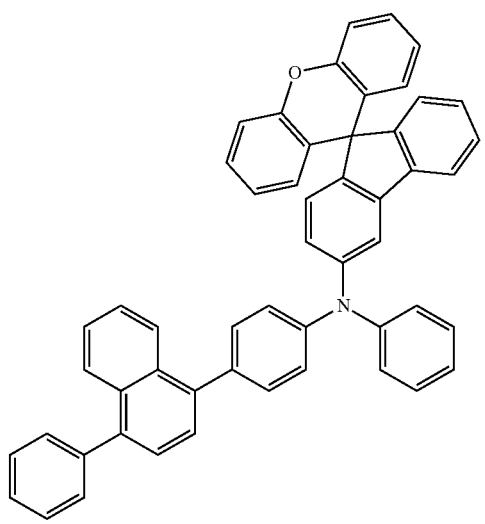
180
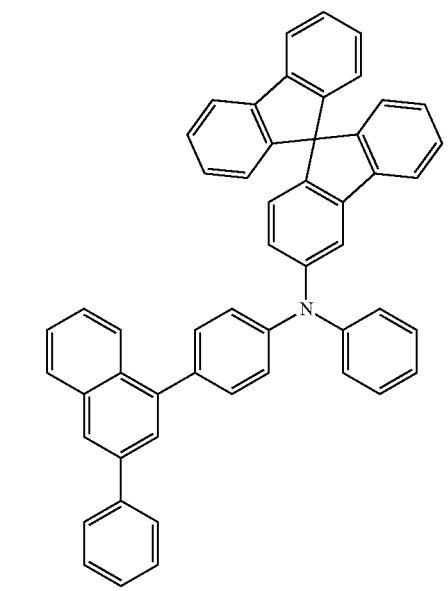
-continued
182
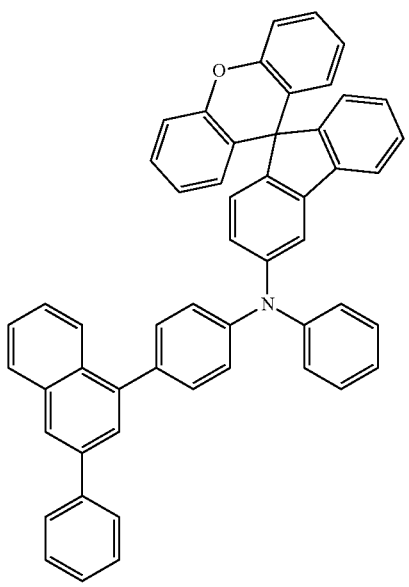
183
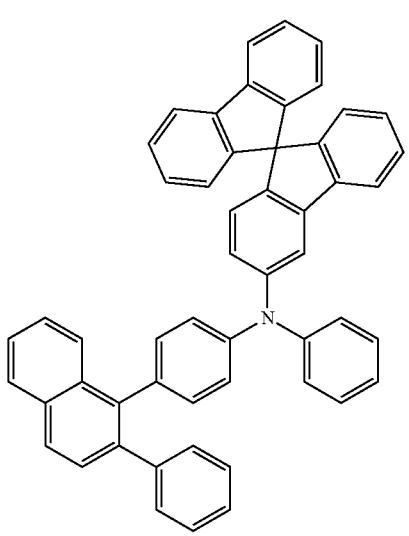
184
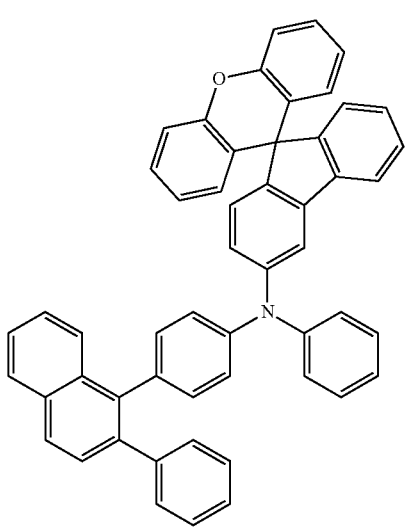

169
-continued
185
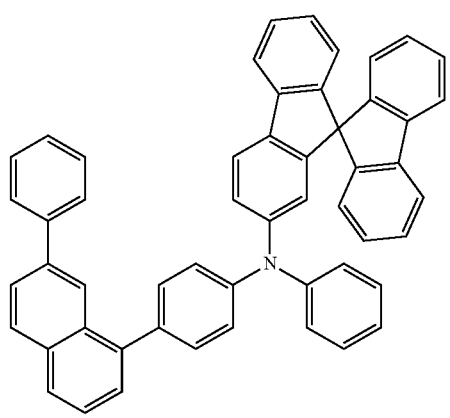
186
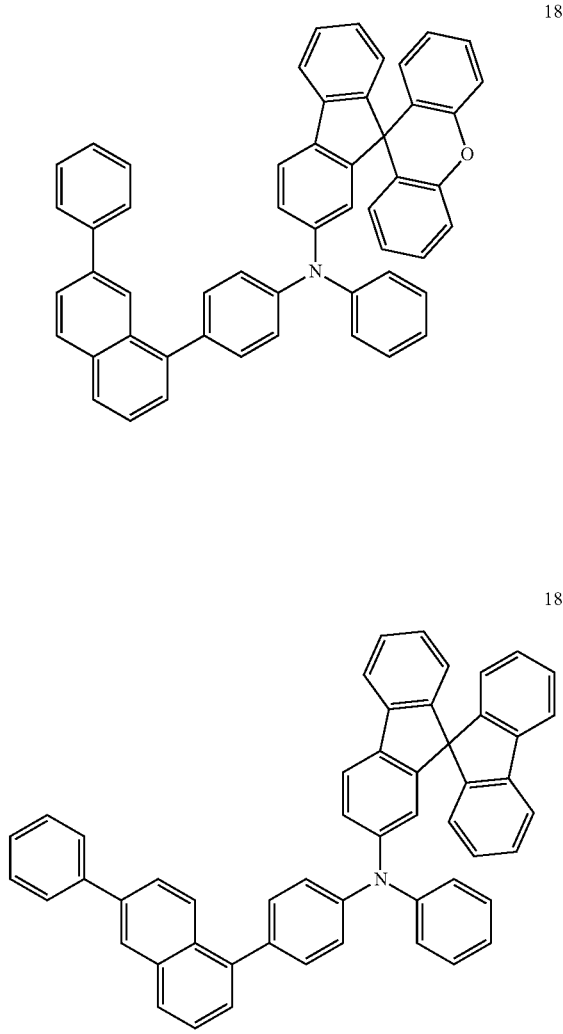
187
170
-continued
188
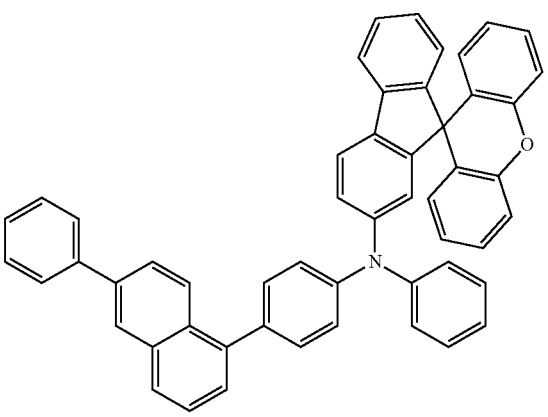
189
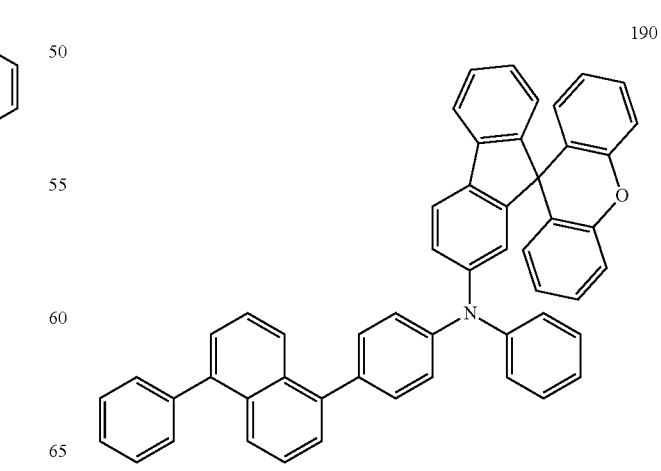
190

191 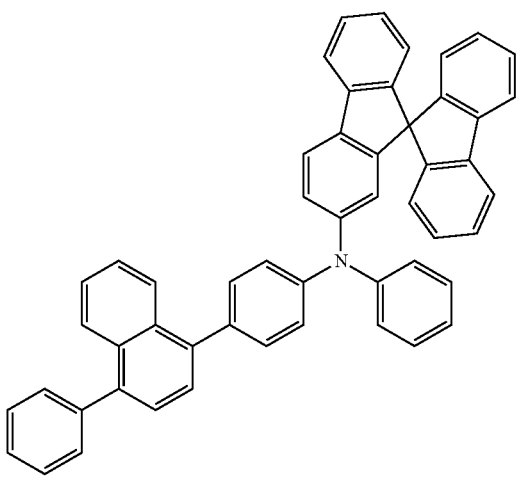
192 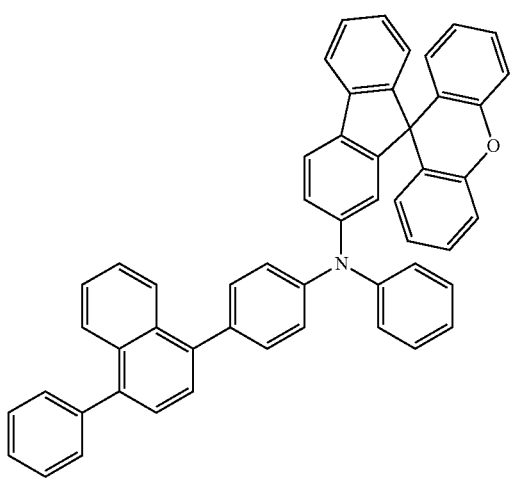
193 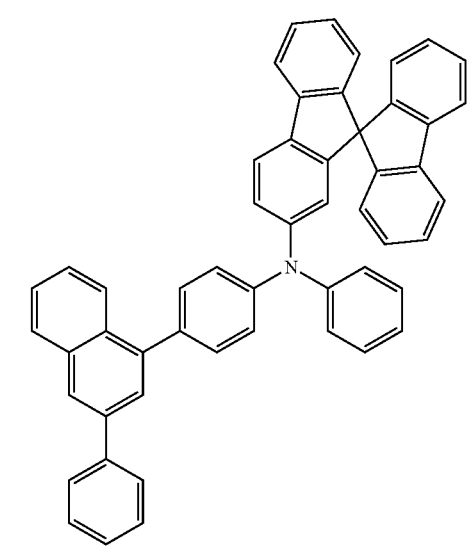
194 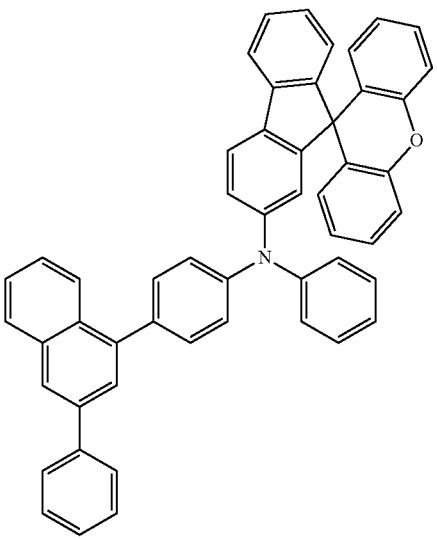
195 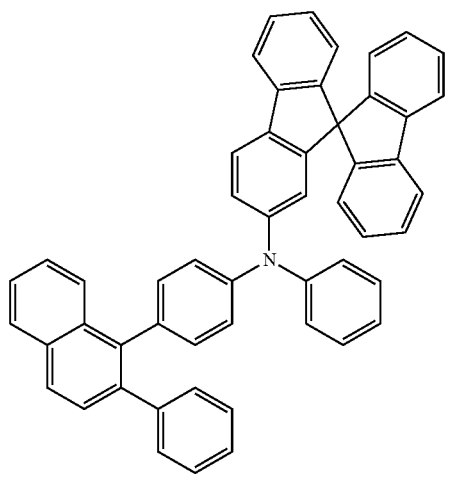
196 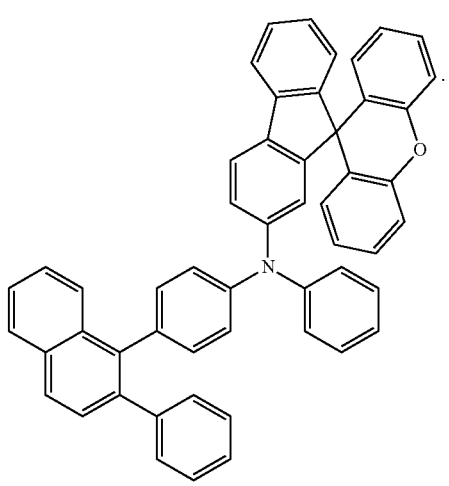
* * * * *

UNITED STATES PATENT AND TRADEMARK OFFICE
CERTIFICATE OF CORRECTION

PATENT NO. : 11,805,697 B2
APPLICATION NO. : 17/947056
DATED : October 31, 2023
INVENTOR(S) : Hideo Miyake et al.

Page 1 of 3

It is certified that error appears in the above-identified patent and that said Letters Patent is hereby corrected as shown below:

In the Claims

In Column 110, Lines 30-50, in Claim 11, in Formula 8, delete " 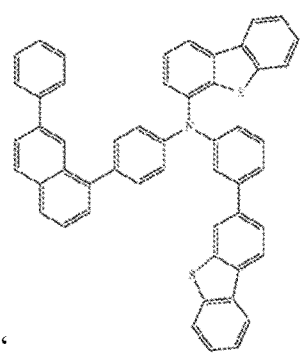 " and insert -- 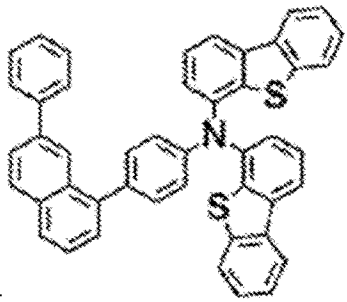 --.

Signed and Sealed this
Tenth Day of September, 2024

Katherine Kelly Vidal
*Director of the United States Patent and Trademark Office*

In Column 124, Lines 20-30, in Claim 11, in Formula 102, delete
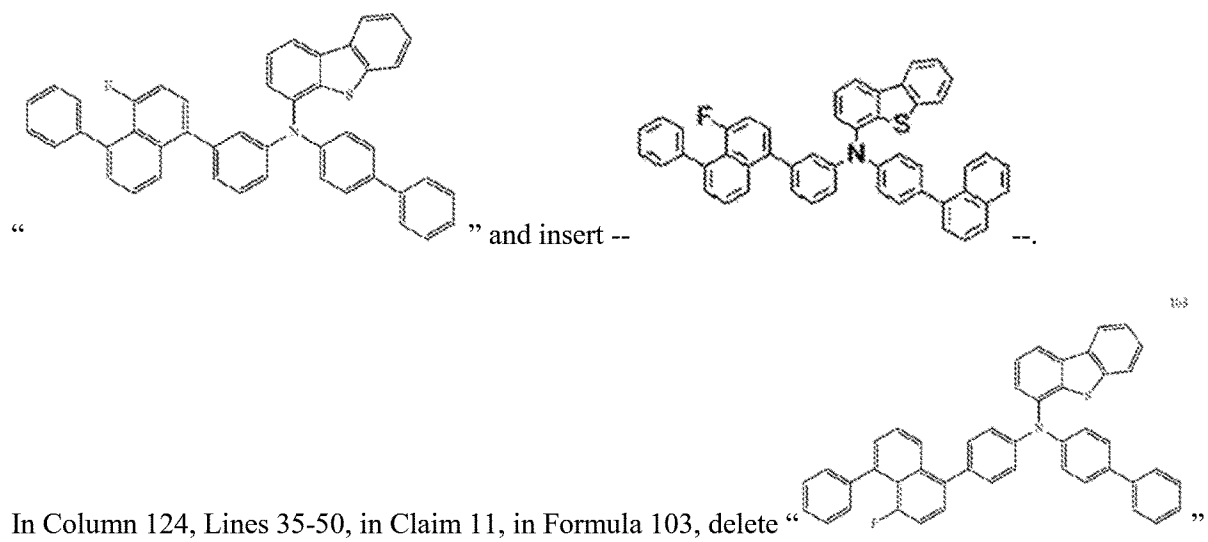
In Column 124, Lines 35-50, in Claim 11, in Formula 103, delete "
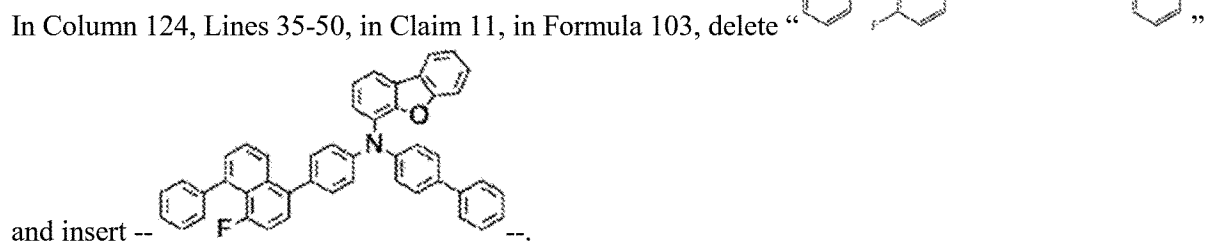
 --.

CERTIFICATE OF CORRECTION (continued)
U.S. Pat. No. 11,805,697 B2

In Column 167, Lines 45-65, in Claim 17, in Formula 180, delete " 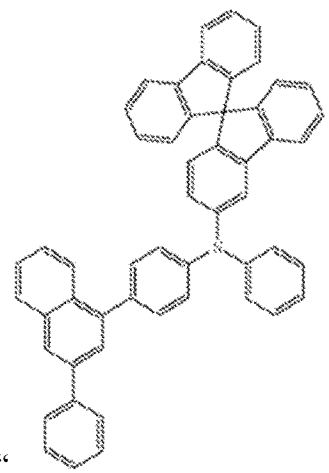 "

and insert -- 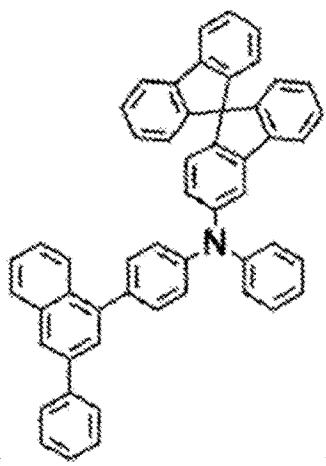 --.